United States Patent
Pizza et al.

(10) Patent No.: US 9,579,372 B2
(45) Date of Patent: Feb. 28, 2017

(54) MENINGOCOCCAL FHBP POLYPEPTIDES

(75) Inventors: Mariagrazia Pizza, Siena (IT); Maria Scarselli, Siena (IT); Marzia Monica Giuliani, Siena (IT); Maria Arico, Poggibonsi (IT); Rino Rappuoli, Castelnuovo Berardenga (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 147 days.

(21) Appl. No.: 12/918,729

(22) PCT Filed: Feb. 20, 2009

(86) PCT No.: PCT/IB2009/005038
§ 371 (c)(1),
(2), (4) Date: Sep. 30, 2010

(87) PCT Pub. No.: WO2009/104097
PCT Pub. Date: Aug. 27, 2009

(65) Prior Publication Data
US 2011/0020390 A1 Jan. 27, 2011

Related U.S. Application Data

(60) Provisional application No. 61/066,711, filed on Feb. 21, 2008.

(51) Int. Cl.
| A61K 39/095 | (2006.01) |
| A61K 39/02 | (2006.01) |
| A61K 39/38 | (2006.01) |
| A61K 38/00 | (2006.01) |
| C07K 1/00 | (2006.01) |
| C07H 21/04 | (2006.01) |
| C12N 15/00 | (2006.01) |
| C07K 14/22 | (2006.01) |
| A61K 39/00 | (2006.01) |

(52) U.S. Cl.
CPC ............ *A61K 39/095* (2013.01); *C07K 14/22* (2013.01); *A61K 39/00* (2013.01)

(58) Field of Classification Search
None
See application file for complete search history.

(56) References Cited

U.S. PATENT DOCUMENTS

| 7,348,006 | B2 | 3/2008 | Contorni et al. |
| 7,576,176 | B1 | 8/2009 | Fraser et al. |
| 7,785,608 | B2 | 8/2010 | Zlotnick et al. |
| 7,862,827 | B2 | 1/2011 | Giuliani et al. |
| 8,101,194 | B2* | 1/2012 | Zlotnick et al. ............ 424/250.1 |
| 8,226,960 | B2 | 7/2012 | Masignani et al. |
| 8,293,251 | B2 | 10/2012 | Scarlato et al. |
| 8,394,390 | B2 | 3/2013 | Galeotti et al. |
| 8,398,988 | B2 | 3/2013 | Contorni et al. |
| 8,398,999 | B2 | 3/2013 | Masignani et al. |
| 8,470,340 | B2 | 6/2013 | Beernink et al. |
| 8,524,251 | B2 | 9/2013 | Fraser et al. |
| 8,563,007 | B1 | 10/2013 | Zlotnick et al. |
| 8,574,597 | B2 | 11/2013 | Zlotnick |
| 8,663,656 | B2 | 3/2014 | Pizza |
| 8,734,812 | B1 | 5/2014 | Galeotti et al. |
| 8,834,888 | B2 | 9/2014 | Contorni et al. |
| 8,840,907 | B2 | 9/2014 | Pizza |
| 8,968,748 | B2 | 3/2015 | Granoff et al. |
| 8,980,286 | B2 | 3/2015 | Comanducci |
| 9,011,869 | B2 | 4/2015 | Pizza |
| 9,056,075 | B2 | 6/2015 | Pizza |
| 9,067,987 | B2 | 6/2015 | Galeotti et al. |
| 9,150,898 | B2 | 10/2015 | Arico |
| 9,156,894 | B2 | 10/2015 | Masignani et al. |
| 9,249,196 | B2 | 2/2016 | Fraser et al. |
| 2003/0134326 | A1 | 7/2003 | Hansen et al. |
| 2004/0092711 | A1 | 5/2004 | Arico |
| 2004/0110670 | A1 | 6/2004 | Arico et al. |
| 2004/0167068 | A1* | 8/2004 | Zlotnick et al. ............... 514/12 |
| 2004/0249125 | A1* | 12/2004 | Pizza et al. .................. 530/350 |
| 2005/0222385 | A1 | 10/2005 | Pizza |
| 2006/0051840 | A1 | 3/2006 | Arico et al. |
| 2006/0171957 | A1 | 8/2006 | Pizza |
| 2006/0240045 | A1 | 10/2006 | Berthet et al. |
| 2006/0251670 | A1 | 11/2006 | Comanducci et al. |
| 2007/0026021 | A1 | 2/2007 | Fraser et al. |
| 2007/0082014 | A1 | 4/2007 | Costantino |
| 2007/0253984 | A1 | 11/2007 | Khandke et al. |
| 2008/0241180 | A1 | 10/2008 | Contorni |
| 2009/0285845 | A1 | 11/2009 | Masignani et al. |

(Continued)

FOREIGN PATENT DOCUMENTS

| EP | 0467714 | 1/1992 |
| EP | 1645631 A2 | 4/2006 |

(Continued)

OTHER PUBLICATIONS

Brenda Collins. Discovery Medicine, Jul. 2011.*
Beernink, P. et al. "Rapid genetic grouping of factor H-binding protein (genome-derived neisserial antigen 1870), a promising group B meningoccocoal vaccine candidate," Clinical and Vaccine Immunology, vol. 13, No. 7, 2006, pp. 758-763.
Pillai, S. et al. "Outer membrane protein (OMP) based vaccine for Neisseria meningitidis serogroup B," Vaccine, vol. 23, No. 17-18, 2005, pp. 2206-2209.
Beernink, P. et al. "Batericidial antibody responses induced by meningocoocal recombinant chimeric factor H-binding protein vaccines," Infection and Immunity, vol. 76, No. 6, 2008, pp. 2568-2575.
Nov. 17, 1997-NM_shotgun.dbs and Dec. 15, 1997-NM.dbs, located at <ftp://ftp.sanger.ac.uk/pub/pathogens/nm/old data/>.
Aderson et al. (2010). "Effectiveness of a bivalent factor H binding protein vaccine across Neisseria meningitidis serogroups," 17th International Pathogenic Neisseria Conference 2010, p. 196.

(Continued)

*Primary Examiner* — S. Devi
(74) *Attorney, Agent, or Firm* — Morrison & Foerster LLP

(57) ABSTRACT fHBP is a protein in *Neisseria meningitidis*. Three families of fHBP are known. To increase the ability of a fHBP protein to elicit antibodies that are cross-reactive between the families, fHBP is selected or engineered to have a sequence which can elicit broad-spectrum bactericidal anti-meningococcal antibodies after administration to a host animal.

**12 Cla

(56) References Cited

U.S. PATENT DOCUMENTS

| | | |
|---|---|---|
| 2010/0267931 A1 | 10/2010 | Arico et al. |
| 2011/0020390 A1 | 1/2011 | Pizza et al. |
| 2012/0107339 A1* | 5/2012 | Granoff et al. ............ 424/190.1 |
| 2014/0037668 A1 | 2/2014 | Giuliani et al. |
| 2014/0363462 A1 | 12/2014 | Aric et al. |
| 2015/0079124 A1 | 3/2015 | Fraser et al. |
| 2015/0086582 A1 | 3/2015 | Fraser et al. |

FOREIGN PATENT DOCUMENTS

| | | |
|---|---|---|
| EP | 1790660 A2 | 5/2007 |
| EP | 2351767 A2 | 8/2011 |
| WO | WO-96/29412 A1 | 9/1996 |
| WO | WO-98/17805 | 4/1998 |
| WO | WO-98/18930 A2 | 5/1998 |
| WO | WO-99/57280 A | 11/1999 |
| WO | WO-00/22430 A2 | 4/2000 |
| WO | WO-00/66791 | 11/2000 |
| WO | WO-01/31019 | 5/2001 |
| WO | WO-01/52885 | 7/2001 |
| WO | WO-01/64920 A | 9/2001 |
| WO | WO-01/64922 A2 | 9/2001 |
| WO | WO-03/009869 A1 | 2/2003 |
| WO | WO-03/020756 A | 3/2003 |
| WO | WO-03/063766 | 8/2003 |
| WO | WO-2004/032958 A1 | 4/2004 |
| WO | WO-2004/048404 | 6/2004 |
| WO | WO-2004/065603 A2 | 8/2004 |
| WO | WO-2004/094596 A2 | 11/2004 |
| WO | 2006/024954 A2 | 3/2006 |
| WO | WO-2006/081259 | 8/2006 |
| WO | 2007/060548 A2 | 5/2007 |
| WO | WO-2007/127665 A2 | 11/2007 |
| WO | WO-2008/125985 A2 | 10/2008 |
| WO | WO-2008/149238 A2 | 12/2008 |
| WO | WO-2009/038889 A1 | 3/2009 |
| WO | WO-2009/104097 A2 | 8/2009 |
| WO | WO-2010/028859 A1 | 3/2010 |
| WO | WO-2010/046715 A1 | 4/2010 |
| WO | WO-2011/110634 A1 | 9/2011 |
| WO | WO-2011/12686 A1 | 10/2011 |
| WO | WO-2013/177397 A1 | 11/2013 |

OTHER PUBLICATIONS

Ala'Aldeen et al. (2010) "Human antibody response to the meningococcal factor H binding protein (LP2086) during invasive disease, colonization and carriage," Vaccine 28:7667-75.

Ambrose et al. (2006). "Characterization of LP2086 expression in Neisseria meningitidis," 15th International Pathogenic Neisseria Conference 2006, p. 103.

Anderson et al. (2008). "Functional cross-reactive antibodies are elicited by a group B Neisseria meningitidis bivalent recombinant lipidated LP2086 vaccine in cynomolgusmacaques," 16th International Pathogenic Neisseria Conference (IPNC) P100, pp. 170-171.

Anderson et al. (2009). "Epidemiology of the serogroup B Neisseria meningitidis (MnB) factor H binding protein and implications for vaccine development," European Society for Paediatric Infectious Disease Symposium 2009, p. 505.

Anderson et al. (2009). "Development of a factor H binding protein vaccine for borad protection against invasive Neisseria meningitidis serogroup B (MnB) disease," 10th European Meningococcal Disease Society Congress 2009, p. 39.

Anderson et al. (2012). "Potential impact of the bivalent rLP2086 vaccine on Neisseria meningitidis invasive disease and carriage isolates in two adolescent populations," European Society for Paediatric Infectious Disease Symposium 2012, p. 807.

Anderson et al. (2013) "Potential impact of the bivalent rLP2086 vaccine on Neisseria meningitidis carriage and invasive serogroup B disease," Hum Vacc Immunotherap 9:471-9.

Appendix I to Statement of Grounds of Appeal filed by df-mp on Sep. 28, 2012, in relation to EP1645631, 1 page.

Appendix II to Statement of Grounds of Appeal filed by df-mp on Sep. 28, 2012, in relation to EP1645631, 2 pages.

Beernick (Jul. 2010) "Impaired immunogenicity of a meningococcal factor H-binding protein vaccine engineered to eliminate factor h binding," Clin Vac Immunol 17(7):1074-1078.

Beernink et al. (Sep. 2008). "Fine antigenic specificity and cooperative bactericidal activity of monoclonal antibodies directed at the meningococcal vaccine candidate factor h-binding protein," Infection and Immunity 76(9):4232-4240.

Bentley et al. (2004). Identification of two immunologically distinct domains on the LP2086 outer membrane lipoprotein of Neisseria meningitidis, 14th International Pathogenic Neisseria Conference 2004, p. 144.

Bernfield L. et al. (Sep. 2002). "Identification of a novel vaccine candidate for group B Neisseria meningitidis," Thirteenth International Pathogenic Neisseria Conference, Norwegian Institute of Public Health, Oslo, Norway, pp. 116 and 124.

Boslego et al. (1991). "Gonorrhea Vaccines," Chapter 17 In Vaccines and Immunotherapy,.Cryz S. J. (Ed.), Pergamon Press: New York, NY, pp. 211-223.

Bouvier et al. (1991). "A gene for a new lipoprotein in the dapA-purC interval of the Escherichia coli chromosome," J Bacteriol 173(17):5523-5531.

Cannon (1989). "Conserved Lipoproteins of Pathogenic Neisseria Species Bearing the H.8 Epitope: Lipid-Modified Azurin and H.8 Outer Membrane Protein," Clinical Microbiology Reviews 2 (Suppl.):S1-S4.

Cantini et al. (Mar. 2006). "Solution Structure of the Immunodominant Domain of Protective Antigen GNA 1870 of Neisseria meningitidis,"Journal of Biological Chemistry 281(11): 7220-7227.

Chen, et al. (1994). "Determination of the optimal aligned spacing between the Shine-Dalgarno sequence and the translation initiation codon of Escherichia coli mRNAs," Nucleic Acids Res. 22(23):4953-4957.

Cohn et al. (2010). "Potential Impact of Serogroup B Vaccines: Prevalence of candidate vaccine antigens among invasive Neisseria meningitidis isolates in the United States," 17th International Pathogenic Neisseria Conference 2010, p. 77.

Cordis, "Preparation of meningococcal antigens," posted online on Feb. 2, 2005, 2 pages.

Cruse et al. (2003). Illustrated Dictionary of Immunology, $2^{nd}$ Ed. CRC Press, pp. 46, 166, and 382.

Database accession No. NMB1994 (cf. XP2231040) (Tettelin et al.), uploaded Oct. 1, 2000.

Declaration by Dr. Ellen Murphy, Ph.D., dated Sep. 14, 2011, submitted in opposition proceedings for EP1645631, 4 pages.

Declaration by Dr. Julian Parkhill dated Jun. 12, 2008, submitted in opposition proceedings for EP1645631, 2 pages.

Declaration by E. Richard Moxon dated Feb. 16, 2013, submitted in opposition proceedings for EP1645631, 5 pages.

Declaration by Emilio A. Emini, Ph.D., dated Nov. 2, 2011, submitted in opposition proceedings for EP1645631, 5 pages.

Declaration by Isabel Delany, dated Feb. 18, 2013, submitted in opposition proceedings for EP1645631, 5 pages.

Declaration by Prof. Paul Dunman, Ph.D., dated Sep. 25, 2012, submitted in opposition proceedings for EP1645631, 14 pages.

Declaration by Rino Rappuoli, dated Oct. 13, 2011, submitted in opposition proceedings for EP1645631, 5 pages.

Declaration by Vega Masignani dated Feb. 18, 2013, submitted in opposition proceedings for EP1645631, 4 pages.

Delgado et al. (2007). "Lipoprotein NMB0928 from Neisseria meningitidis serogroup B as a novel vaccine candidate," Vaccine 25:8420-8431.

Dinthilhac and Claverys (1997). "The adc locus, which affects competence for genetic transformation in Streptococcus pneumoniae, encodes an ABC transporter with a putative lipoprotein homologous to a family of streptococcal adhesins," Res Bicrobiol 148:119-131.

Dlawer et al. (2010). "Human antibody responses to the meningococcal factor H binding protein LP2086 during invasive disease," 17th International Pathogenic Neisseria Conference 2010, p. 130.

(56) References Cited

OTHER PUBLICATIONS

Facts and Submissions dated May 21, 2012, in relation to EP1645631, 30 pages.
Farley J. et al. (Sep. 2002). "Characterization, cloning and expression of different subfamilies of the ORF 2086 gene from Neisseria meningitidis," Thirteenth International Pathogenic Neisseria Conference, Norwegian Institute of Public Health, Oslo, Norway, p. 124.
Feavers et al. (2009). "Meningococcal protein antigens and vaccines," Vaccine 275:B42-B50.
Fleischmann et al. (1995). "Whole-Genome Random Sequencing and Assembly of Haemophilus influenzae Rd," Science 269:496-501.
Fletcher et al. (2004). "Vaccine Potential of the Neisseria meningitidis 2086 Lipoprotein,"*Infection and Immunity* 72(4): 2088-2100.
Fontana et al. (2002). A genomic approach Abstract from the 13th International Pathogenic Neisseria Conference, Oslo, Norway, Sep. 1-6, 2002. P. 248.
Fraser et al. (1997). "Genomic sequence of a lyme disease spirochaete, *Borrelia burgdorferi*," Nature 390:580-586.
Fraser et al. (1998). "Complete genome sequence of *Treponema pallidum*, the syphilis spirochete," Science 281:375-388.
GenPept accession No. AAF42204, "hypothetical protein NMB1870 [Neisseria meningitidis MC58]," retrieved on Sep. 26, 2012, 2 pages.
Giuliani et al. (2006). "A universal vaccine for serogroup B meningococcus," PNAS 103(29):10834-10839.
Giuliani et al. (2010). "Measuring antigen-specific bactericidal responses to a multicomponent vaccine against serogroup B meningococcus," Vaccine 28:5023-5030.
Giuliani et al. (Feb. 2005). "The Region Comprising Amino Acids 100 to 255 of Neisseria meningitidis Lipoprotein GNA 1870 Elicits Bactericidal Antibodies,"*Infection and Immunity* 73(2): 1151-1160.
Gold and Stormo (1987). "Translation Initiation", in *Escherichia con* and *Salmonella typhimurium*, Cellular and Molecular Biology, Ed. Neidhardt, pp. 1302-1307.
Gorringe et al. (2009). "16th International Pathogenic Neisseria Conference: recent progress towards effective meningococcal disease vaccines," Human Vaccines 5(2):53-56.
Grandi (2005). "Reverse vaccinology: a critical analysis," in Encyclopedia of Genetics, Genomics, Proteomics and Bioinformatics, pp. 1322-1326.
Granoff, DM. (2009). Relative importance of complement-mediated bactericidal and opsonic activity for protection against meningococcal disease. Vaccine 27 (Supplement 2): B117-B125.
Harris et al. (2008). "Development and qualification of serum bactericidal assays for Neisseria meningitidis serogroup B," 16th International Pathogenic Neisseria Conference 2008, p. 268-269.
Harris et al. (2010). "Robustness of the Serum Bactericidal Activity (SBA) Assay for Neisseria meningitidis serogroup B," 17th International Pathogenic Neisseria Conference 2010, p. 169.
Harris et al. (2011) "Preclinical evidence for the potential of a bivalent fHBP vaccine to prevent Neisseria meningitidis serogroup C disease," Human Vaccines 7:1 (suppl) 1-7.
Hayashi and Wu, "Identification and characterization of lipid-modified proteins in bacteria," Chapter 10 in Lipid Modifications of Proteins: A Practical Approach, Hooper and Turner (eds.), published in 1992, 27 pages.
Hem et al. (1995). "Structure and properties of aluminum-containing adjuvants," Vaccine Design. Subunit and Adjuvant Approach, pp. 249-276.
Hodge et al. (2006). "Development of a luminex-based meningococcal rLP2086-specific human IgG assay," 15th International Pathogenic Neisseria Conference 2006, p. 113.
Hoiseth et al. (2008). "LP2086 and MLST distribution in epidemiologically relevant strains of serogroup B Neisseria meningitidis," 16th International Pathogenic Neisseria Conference 2008, p. 205.
Hou et al. (2005) "Protective antibody responses elicited by a meningococcal outer membrane vesicle vaccine with overexpressed genome-derived neisserial antigen 1870," J Infect Dis 192(4):580-90.
Hung et al. (2011). "The Neisseria meningitidis macrophage infectivity potentiator protein induces cross-strain serum bactericidal sctivity and is a potential serogroup B vaccine candidate," Infect Immun 79(9):3784-3791.
Jacobsson et al. (2009). "Prevalence and sequence variations of the genes encoding the five antigens included in the novel 5CVMB vaccine covering group B meningococcal disease" Vaccine. 27:1579-1584.
Jansen et al. (2008). "Bivalent recombinant LP2086 vaccine to provide broad protection against Neiseria meningitidis B disease: immunological correlates of protection and how to assess coverage against invasive MnB strains," 16th International Pathogenic Neisseria Conference 2008, p. 80-81.
Jansen et al. (2009). "Development of a bivalent factor H binding protein vaccine to broadly protect against invasive Neisseria meningitides serogroup B (MnB) disease," European Society for Paediatric Infectious Disease Symposium 2009, p. 311.
Jansen et al. (2010). "Estimating effectiveness for Neisseria meningitidis serogroup B (MnB) vaccine candidates composed of non-serogroup specific antigens," 17th International Pathogenic Neisseria Conference 2010, p. 37.
Jansen et al. (2011). "Monitoring the Breadth of Coverage of Meningococcal Vaccines: An Overview and Progress Update on the Pfizer Bivalent LP2086 Vaccine Program," 14th Annual Conference on Vaccine Research, 2011, p. 74.
JCVI-CMR website showing Z2491 Sanger sequence (http://cmr.jcvi.org/tigr-scripts/CMR/shared/Genomes.cgi and links). (2010).
Jiang et al. (2003). "Using rate of acid neutralization to characterize aluminum phosphate adjuvant," Pharma Dev Tech 8(4):349-356.
Jiang et al. (2006). "Serum IgG response induced by a bivalent recombinant LP2086 provides broad protection against serogroup B Neisseria meningitidis," 15th International Pathogenic Neisseria Conference 2006, p. 113.
Jiang et al. (2008). "Prediction of broad vaccine coverage for a bivalent rLP2086 based vaccine which elicits serum bactericidal activity against a diverse collection of serogroup B meningococci," 16th International Pathogenic Neisseria Conference 2008, p. 57-58.
Jiang et al., (2010) "Broad vaccine coverage predicted for a bivalent recombinant factor H binding protein based vaccine to prevent serogroup B meningococcal disease" Vaccine 28:6086-6093.
Johnson et al. (1999). "Analysis of the human Ig isotype response to lactoferrin binding protein a from Neisseria meningitidis," FEMS Immun. Med. Microbial. 25(4): 349-354.
Jones et al. (2009). "Generation of human serum complement lots that perform consistently for use in Neisseria meningitidis serogroup B (MnB) vaccine clinical trials," European Society for Paediatric Infectious Disease Symposium 2009, p. 566.
Juncker et al. (2003). "Prediction of lipoprotein signal peptides in gram-negative bacteria," Protein Sci 12:1652-1662.
Koeberling et al. (2007). "Improved immunogenicity of a H44/76 group B outer membrane vesicle vaccine with over-expressed genome-derived Neisserial antigen 1870," Vaccine 25(10):1912-1920.
Koeberling et al. (2009). "Meningococcal outer membrane vesicle vaccines derived from mutant strains engineered to express factor H binding proteins from antigenic variant groups 1 and 2," Clin Vac Immunol, 16(2):156-162.
Liebl et al. (1997). "Properties and gene structure of the *Thermotoga maritima* alpha-amylase AmyA, a putative lipoprotein of a *hyperthermophilic bacterium*," J Bacteriol 179(3):941-948.
Lucidarme et al., (Sep. 16, 2009) "Characterization of fHbp, nhba (gna2132), nadA, porA, sequence type (ST), and genomic presence of IS1301 in group B meningococcal ST269 clonal complex isolates from England and Wales" Journal of Clinical Microbiology, 47(11):3577-85.
Lucidarme et al., 2010 "Characterization of fHbp, nhba (gna2132), nadA, porA, and sequence type in group B meningococcal case isolates collected in England and Wales during Jan. 2008 and

(56) References Cited

OTHER PUBLICATIONS potential coverage of an investigational group B meningococcal vaccine" Clinical and Vaccine Immunology 17(6):919-929.
Marshall et al. (2008). "A randomized, placebo-controlled, double-blind, phase 1 trial of ascending doses of meningococcal group B rLP2086 vaccine in healthy adults," 16th International Pathogenic Neisseria Conference 2008, p. 271-272.
Marshall et al. (2011). "Phase I randomised controlled clinical trial of safety and immunogenicity of a meningococcal B bivalent LP2086 vaccine in healthy toddlers," European Society for Paediatric Infectious Disease Symposium 2011, p. 189.
Marshall et al. (2012) "Safety and immunogenicity of a meningococcal B bivalent rLP2086 vaccine in healthy toddlers aged 18-36 months: A phase 1 randomized-controlled clinical trial," Ped Infect Dis J 31:1061-8.
Marshall et al. (2013) "A phase 2 open-label safety and immunogenicity study of a meningococcal B bivalent rLP2086 vaccine in healthy adults," Vaccine 31:1569-75.
Mascioni et al. (2008). "Determination of the domain and solution structure of rLP2086, a meningococcal vaccine candidate and human factor H binding protein," 16th International Pathogenic Neisseria Conference 2008, p. 77-78.
Mascioni et al. (2009) "Structural basis for the immunogenic properties of the meningococcal vaccine candidate LP2086," J Biol Chem 284:8738-46.
Mascioni et al. (2010) "NMR dynamics and antibody recognition of the meningococcal lipidated outer membrane protein LP2086 in micellar solution," Biochim Biophys Acta 1798:87-93.
Masignani V. (Mar. 17. 2003). "Vaccination against Neisseria meningitidis using three variants of the lipoprotein GNA1870," J. Exp. Med. 197(6):789-799.
McNeil et al. (2009) "Detection of LP2086 on the cell surface of Neisseria meningitidis and its accessibility in the presence of serogroup B capsular polysaccharide," Vaccine 27:3417-21.
McNeil et al. (2010). "Anti-fHBP antibodies elicited after immunization with a recombinant fHBP vaccine candidate (rLP2086) can displace human Factor H from the surface of Serogroup B Meningococci," 17th International Pathogenic Neisseria Conference 2010, p. 94.
McNeil et al. (2013) "Role of factor H binding protein in Neisseria meningitidis virulence and its potential as a vaccine candidate to broadly protect against meningococcal disease," Microbiol Mol Biol Rev 77:234.
Milagres et al. (1998). "Specificity of bactericidal antibody response to serogroup B meningococcal strains in Brazilian children after immunization with an outer membrane vaccine," Infection and Immun. 66(10): 4755-4781.
Morley, S. et al. (Dec. 12, 2001). "Vaccine prevention of meningococcal disease, coming soon?"*Vaccine* 20(5-6):666-687.
Munkley, et al. (1991). "Blocking of bactericidal killing of Neisseria meningitidis by antibodies directed against slacc 4 outer membrane proteins," Microbial Pathogenesis 11: 447-452.
Murphy et al. (2008). "Sequence diversity of vaccine candidate LP2086 in Neisseria meningitidis serogroup B strains causing invasive disease," 16th International Pathogenic Neisseria Conference 2008, p. 61.
Murphy et al. (2010). "Prevalence of Factor H Binding Protein (fHBP) Variants in N. meningitidis Carriage Isolates," 17th International Pathogenic Neisseria Conference 2010, p. 96.
Murphy et al., (2009) "Sequence diversity of the factor H binding protein vaccine candidate in epidemiologically relevant strains of serogroup B Neisseria meningitidis" J Infect Dis 379-389, 2009.
Nassif (2000). "A Furtive Pathogen Revealed," Science 287:1767-1768.
Notice of Opposition against European Patent EP 1645631, granted on Oct. 24, 2007. Opposition filed on Jul. 23, 2008. 20 pages.
Novartis (Jan. 22, 2013) "Novartis receives EU approval for Bexsero® , first vaccine to prevent the leading cause of life-threatening meningitis across Europe," Media Release, 3 pages.
Novartis (Oct. 9, 2008) "New Phase II data show Novartis investigational Meningitis B vaccine may also protect infants six months and older," Media Release, 4 pages.
Pajon et al. (2010). "Frequency of factor H-binding protein modular groups and susceptibility to cross-reactive bactericidal activity in invasive meningococcal isolates" Vaccine 28:2122-2129.
Pajon et al. (2012). "Design of meningococcal factor H binding protein mutant vaccines that do not bind human complement factor H," Infect Immun 80:2667-2677.
Parkhill, "Campylobacter jejuni genome sequence at the Sanger Centre," Post on BIOSCI/Bionet of May 8, 1998.
Parkhill, J. et al. (Mar. 2000). "Complete DNA Sequence of a Serogroup A Strain of Neisseria meningitides Z2491,"*Nature* 404(6777):502-506.
Patentees' Response to Opposition against European Patent EP 1645631, granted on Oct. 24, 2007. 13 pages.
Pettersson, et al. (2006). "Vaccine potential of the Neisseria meningitidis lactoferrin-binding proteins LbpA and LbpB," Vaccine 24(17):3545-3557.
Pizza et al. (2000). "Identification of Vaccine Candidates Against Serogroup B Meningococcus by Whole-Genome Sequencing," Science 287(5459):1816-1820.
Pizza et al. (2008) "Factor H-binding protein, a unique meningococcal vaccine antigen" Vaccine 26S:146-8.
Progress through the Sanger Institute FTP server (May 12, 2009), 15 pages.
Prosite, "ScanProsite Results Viewer: USERSEQ1 (280aa)," retrieved on Jun. 21, 2012, 1 page.
PSORT analysis of 200 of the sequences disclosed in PCT/US99/09346 (Jan. 1, 2010), 209 pages.
PSORT analysis of SEQ ID NOs: 4 and 6, and of 'Contig295' 300mer (May 8, 2009), 5 pages.
PSORT prediction result for SEQ ID No: 2 (Mar. 30, 2010), 1 page.
Pugsley (1993). "The complete general secretory pathway in gram-negative bacteria," Microbiological Rev 5(1):50-108.
Response to Appeal filed by Carpmaels & Ransford on Feb. 18, 2013, in relation to EP1645631, 21 pages.
Response to Appeal filed by df-mp on Feb. 18, 2013, in relation to EP1645631, 28 pages.
Response to Communication, filed in EP Application No. 07075161. 5. Oct. 28, 2009.
Richmond et al. (2008). "A randomized, observer-blinded, active control, phase 1 trial of meningococcal serogroup B rLP2086 vaccine in healthy children and adolescents aged 8 to 14 years," 16th International Pathogenic Neisseria Conference 2008, p. 270-271.
Richmond et al. (2010). "Safety & immunogenicity of serogroup B Neisseria meningitidis (MnB) rLP2086 vaccine in adults and adolescent subjects: overview of 3 clinical trials," 17th International Pathogenic Neisseria Conference 2010, p. 37.
Richmond et al. (2011). "Phase II randomised controlled trial of safety and immunogenicity of a meningococcal B bivalent vaccine (rLP2086) in healthy adolescents," European Society for Paediatric Infectious Disease Symposium 2011, p. 192.
Richmond et al. (2012) "A bivalent Neisseria meningitidis recombinant lipidated factor H binding protein vaccine in young adults: Results of a randomized, controlled, dose-escalation phase 1 trial," Vaccine 30(43):6163-74.
Richmond et al. (2012a) "Safety, immunogenicity, and tolerability of meningococcal serogroup B bivalent recombinant lipoprotein 2086 vaccine in healthy adolescents: a randomized, single-blind, placebo-controlled, phase 2 trial," Lancet Infect Dis 12:597-607.
Rinaudo et al. (2009). "Vaccinology in the genome era", The Journal of Clinical Investigation, 119(9):2515-2525.
Sanger Centre's "Projects" website as of Dec. 10, 1997 as retrievable via http://web.archive.org.
Scarselli et al. (Feb. 13, 2009). "Epitope Mapping of a Bactericidal Monoclonal Antibody against the Factor H Binding Protein of Neisseria meningitides," Journal of Molecular Biology 386(1):97-108.
Schneider et al. (Apr. 16, 2009) "Neisseria meningitidis recruits factor H using protein mimicry of host carbohydrates," Nature 458(7240):890-893.

(56) References Cited

OTHER PUBLICATIONS

Seeber et al. (1991). "Predicting the adsorption of proteins by aluminum-containing adjuvants," Vaccine 9(3):201-203.
Seib et al. (2010). "Influence of serogroup B meningococcal vaccine antigens on growth and survival of the mengococcus in vitro and in ex vivo and in vivo models of infection," Vaccine 28(12):2416-2427.
Sequence for "Putative Lipoprotein [*Neisseria Meningitidis* Z2491]," NCBI Reference Sequence: YP_002342062.1, Mar. 30, 2000.
Serruto et al. (2009). "Genome-based approaches to develop vaccines against bacterial pathogens," Vaccine 27:3245-3250.
Sheldon et al. (2011). "Phase 1, Randomized, Open-Label, Study to Assess the Safety and Immunogenicity of Serogroup B Neisseria Meningitidis (Mnb) rLP2086 Vaccine in Healthy Adults," 14th Annual Conference on Vaccine Research, 2011, p. 59-60.
Sheldon et al. (2012) "A phase 1, randomized, open-label, active-controlled trial to assess the safety of a meningococcal serogroup B bivalent rLP2086 vaccine in healthy adults," Hum Vacc Immunotherap 8:1-8.
Shevchik et al. (1996). "Characterization of pectin methylesterase B, an outer membrane lipoprotein of *Erwinia chrysanthemi* 3937," Mole Microbiol 19(3):455-466.
Statement of Grounds of Appeal filed by Carpmaels & Ransford on Oct. 4, 2012, in relation to EP1645631, 9 pages.
Statement of Grounds of Appeal filed by df-mp on Sep. 28, 2012, in relation to EP1645631, 54 pages.
Supplemental Submissions in Opposition against European Patent EP 1645631, granted on Oct. 24, 2007. Opposition filed on May 25, 2010. 28 pages.
Supplementary Declaration by Dr. Julian Parkhill, dated May 10, 2010, submitted in opposition proceedings for EP1645631, 4 pages.
Supplementary declaration by Ellen Murphy dated Sep. 26, 2012, submitted in opposition proceedings for EP1645631, 3 pages.
Supplementary declaration by Prof. Paul Dunman, Ph.D., dated Sep. 25, 2012, submitted in opposition proceedings for EP1645631, 14 pages.
Sutcliffe and Russell (1995). "Lipoproteins of gram-positive bacteria," J Bacteriol 177(5):1123-1128.
Tan et al. (2010). "Advances in the development of vaccines against Neisseria meningitidis," NEJM 362(16):1511-1520.
Telford et al. (2003). "Genomic and Proteomics in Vaccine Design", in *New Bacterial Vaccines*, edited by Ellis et al. Kleweur Academic/Plenum Publishers, USA. Pages 1-11.
Tettelin et al. (Mar. 10, 2000). "Complete Genome Sequence of Neisseria meningitidis Serogroup B Strain MC58," Science 287(5459):1809-1815.
The printed output from the NCBI open reading frame finder (Oct. 20, 2008), 12 pages.
TIGR website as of 1998, 8 pages.
United States Office Action mailed on Feb. 11, 2009, for U. S. Appl. No. 10/181,600 filed on Jan. 17, 2001, 5 pages.
United States Office Action mailed on Jul. 24, 2008, for U. S. Appl. No. 10/181,600 filed on Jan. 17, 2001, 23 pages.
United States Office Action mailed on Jul. 7, 2009, for U. S. Appl. No. 10/181,600 filed on Jan. 17, 2001, 23 pages.
U. S. Appl. No. 60/098,685, "Neisseria Spp, Polypeptide, Gene Sequence and Uses Thereof," filed Sep. 1, 1998.
von Heijne (1989). "The structure of signal peptides from bacterial lipoproteins," Protein Engineering 2(7):531-534.
Wang et al. (2010). "Prevalence and genetic diversity of candidate vaccine antigens among invasive Neisseria meningitidis isolates in the United States," 17th International Pathogenic Neisseria Conference 2010, p. 122.
Welsch et al. (2004). "Protective Activity of Monclonal Antibodies to Genome-Derived Neisserial Antigen 1870, a Neisseria meningitidis Candidate Vaccine,"*The Journal of Immunology* 172: 5606-5615.
Welsch et al. (2007) "A novel mechanism for complement-mediated killing of encapsulated Neisseria meningitidis elicited by monoclonal antibodies to factor H-binding protein (genome-derived Neisserial antigen 1870)" Molecular Immunology 44(1-3):256.
Welsch et al. (Apr. 1, 2008). "Complement-dependent synergistic bactericidal activity of antibodies against factor H-binding protein, a sparsely distributed meningococcal vaccine antigen," J Infect Dis 197(7):1053-1061.
Woods, et al. (1987). "Resistance to meningococcemia apparently conferred by anti-H.8 monoclonal antibody is due to contaminating endotoxin and not to specific immunoprotection," Infection and Immunity 55(8):1927-1928.
Wu et al. (1996). "A protein class database organized with ProSite protein groups and PIR superfamilies," J Comp Biol 3(4):547-561.
York et al. (2010). "fHBP epidemiology of invasive meningococcal B isolates from Spain and Germany: age based," 17th International Pathogenic Neisseria Conference 2010, p. 109.
Zhu et al. (2004). "Evaluation of the purified recombinant lipidated P2086 protein as a vaccine candidate for group B Neisseria meningitidis in a murine nasal challenge model," 14th International Pathogenic Neisseria Conference 2004, p. 199.
Zhu et al. (2005) "Evaluation of recombinant lipidated P2086 protein as a vaccine candidate for group B Neisseria meningitidis in a murine nasal challenge model," Infect Immun 73(10):6838-45.
Zhu et al. (2006) "Intranasal immunization of mice with recombinant lipidated P2086 protein reduces nasal colonization of group B Neisseria meningitidis," Vaccine 24:5420-5.
Zhu et al. (2006). "Effective immunization strategy against group B Neisseria meningitidis using purified recombinant lipidated P2086 protein," 15th International Pathogenic Neisseria Conference 2006, p. 47.
Zlotnick et al. (2009). "Epidemiology of the serogroup B Neisseria meningitidis (MnB) factor H binding protein in strains sampled from Spain and Germany in the years 2001-2006," 10th European Meningococcal Disease Society Congress 2009, p. 81.
Zlotnick et al. (2010). "Biochemical and biophysical analysis indicates conformation plays an important role in the binding of hfH and antibodies to the fHBP of N. meningitidis," 17th International Pathogenic Neisseria Conference 2010, p. 38.
Vermont, et al., "Cross-Reactivity of Antibodies against PorA after Vaccination with a Meningococcal B Outer Membrane Vesicle Vaccine," Infection and Immunity, Apr. 2003, pp. 1650-1655.
Adams (1996). "Should Non-Peer-Reviewed Raw DNA Sequence Data Release Be Forced on the Scientific Community?," Science, 274: 534-536.
Beernink et al. (2011). "A meningococcal factor H binding protein mutant that eliminates factor H binding enhances protective antibody responses to vaccination," J Immunol, 186(6):3606-14.
BenMohamed et al. (2002). "Lipopeptide vaccines-yesterday, today, and tomorrow," Lancet 2(7):425-431.
Biswas et al. (1995). "Characterization of IbpA, the structural gene for a lactoferrin receptor in Neisseria gonorrhoeae," Infection and Immunity, 63(8): 2958-2967.
Blattner et al. (1997). "The complete genome sequence of *Escherichia coli* K-12," Science 277 (5331): 1453-1474.
Clinical Trial No. NCT00500032, (2007). "Blood collection for use in serological assay development from healthy adult volunteers," U.S. National Institutes of Health, retrieved online at <http://clinicaltrials.gov/ct2/show/NCT00500032?term=NCT00500032&rank=1>.
Clinical Trial No. NCT00808028, (2008). "A study evaluating safety and immunogenicity of meningococcal B rIp2086 vaccine in adolescents," U.S. National Institutes of Health, retrieved online at <http://clinicaltrials.gov/ct2/show/NCT00808028?term=NCT00808028&rank=1>.
Cole et al. (1998). "Deciphering the biology of Mycobacterium tuberculosis from the complete genome sequence," Nature 394:651-653.
Database UniProt (Oct. 1, 2000), "SubName: Full=Uncharacterized protein" retrieved from EBI, accession no. Q9JXV4 Database accession no. Q9JXV4.
Decision revoking the European Patent, filed in opposition against EP1976990, dated Nov. 11, 2013, 15 pages.
Decision to refuse a patent application, filed in the Opposition against EP1645631, dated Apr. 28, 2009, 7 pages.

(56) References Cited

OTHER PUBLICATIONS

Declaration by Dr. Julian Parkhill, filed in the Opposition against EP1645631, dated Jul. 10, 2014, 5 pages.
Declaration by Ellen Murphy, filed in the Opposition against EP1645631, dated May 12, 2014, 3 pages.
Donnelly et al. (2010). "Qualitative and quantitative assessment of meningococcal antigens to evaluate the potential strain coverage of protein-based vaccines," Proc Natl Acad Sci U S A, 107(45):19490-5.
Elzanowski et al. (2013). "The Genetic Codes, a compilation," Retrieved from http://www.bioinformatics.org/JaMBW/2/3/TranslationTables.html.
Experimental data: expression of NspA, '287' and '741' on 3 strains of bacteria, filed in opposition against EP1534326, dated Aug. 4, 2010. 2 pages.
Frankel et al. (2000). "Characterization of diphtheria fusion proteins targeted to the human interleukin-3 receptor," Protein Eng, 13(8):575-81.
Gene Browser, Nature Technology Corporation, filed in the Opposition against EP1645631, dated Jun. 26, 2013, 6 pages.
Hoist et al. (2014). "Variability of genes encoding surface proteins used as vaccine antigens in meningococcal endemic and epidemic strain panels from Norway," Vaccine 32:2722-2731.
Interlocutory decision in opposition proceedings, filed in the Opposition against EP1645631, dated May 21, 2012, 82 pages.
Koeberling et al. (2008). "Bactericidal antibody responses elicited by a meningococcal outer membrane vesicle vaccine with overexpressed factor H-binding protein and genetically attenuated endotoxin," J. Infect. Dis., 198(2):262-270.
Kovacs-Simon et al. (2011). "Lipoproteins of Bacterial Pathogens," Infect Immun 79(2):548-561.
Lewis et al. (2010). "The meningococcal vaccine candidate neisserial surface protein a (NspA) binds to factor H and enhances meningococcal resistance to complement," PLoS Pathogens 6(7):e1001027.
Liechti et al. (2012). "Outer membrane biogenesis in *Escherichia coli*, Neisseria meningitidis, and Helicobacter pylori: paradigm deviations in H. pylori," Front Cell and Infect Microbiol 2:article 29.
Lindblad, (2004). "Aluminium compounds for use in vaccines," Immunol Cell Biol.,82(5):497-505.
Madico et al. (2006). "The meningococcal vaccine candidate GNA1870 binds the complement regulatory protein factor H and enhances serum resistance," J Immunol 177(1):501-510.
Meyer et al. (1984). "Pilus genes of Neisseria gonorrheae: Chromosomal organization and DNA sequence," Proc. Natl. Acad. Sci. Usa 81: 6110-6114.
Minutes of the oral proceedings, filed in the Opposition against EP1645631, dated Feb. 11, 2014, 4 pages.
Notice of Opposition against Ep 1562983, filed on Jul. 1, 2014, 23 pages.
Notice of Opposition against EP1645631, filed in the Opposition against EP1645631, dated Jul. 23, 2008, 25 pages.
Notice of Opposition filed May 24, 2012, filed in opposition against EP1976990, 19 pages.
Novartis (Jun. 9, 2011). "Novartis candidate vaccine Bexsero® shows significant potential in providing broad coverage against meningococcal serogroup B infections." Media Release, 6 pages.
Opponent's Further Submission in Preparation of the Oral Proceedings, filed in the Opposition against EP1645631, dated Nov. 3, 2011, 6 pages.
Opponent's Response to the Patentee's Submission dated Feb. 18, 2013, filed in the Opposition against EP1645631, dated Jul. 24 2014, 34 pages.
Opponents Final Written Submission in Preparation of Oral Proceedings, filed in the Opposition against EP1645631, dated Sep. 14, 2011, 28 pages.
ORF Finder (2013). "Bacterial Code," Retrieved from http://www.ncbi.nlm.nih.gov/gorf/gorf.html, 3 pages.

Pakula et al. (1989). "Genetic analysis of protein stability and function," Annu Rev Genet, 23:289-310.
Patentee's Submissions under Rule 116 EPC, filed in the Opposition against EP1645631, dated Sep. 13, 2011, 13 pages.
Plikaytis et al. (2012). "Interlaboratory standardization of the sandwich enzyme-linked immunosorbent assay designed for MATS, a rapid, reproducible method for estimating the strain coverage of investigational vaccines," Clin Vaccine Immunol, (10):1609-17.
Sandbu et al. (2007). "Immunogenicity and safety of a combination of two serogroup B meningococcal outer membrane vesicle vaccines," Clin Vaccine Immunol, 14(9):1062-9.
Seib et al. (2011). "Characterization of Diverse Subvariants of the Meningococcal Factor H (fH) Binding Protein for Their Ability to Bind fH, To Mediate Serum Resistance, and To Induce Bactericidal Antibodies," Infect Immun, 79(2):970-81.
Sprengart et al. (1997). "Functional importance of RNA interactions in selection of translation initiation codons," Molecular Microbiology, 24(1): 19-28.
Submission of the Patentee of Jul. 6, 2012, filed Jun. 24, 2014, in the Opposition against EP1645631, 4 pages.
Summons to oral proceedings pursuant to Rule 115(1) EPC, filed in the Opposition against EP1645631, dated Nov. 11, 2013, 12 pages.
Supplementary Submission to the Grounds of Appeal, filed in the Opposition against EP1645631, dated Sep. 28, 2012, 2 pages.
Swaminathan (1996). "Molecular cloning of the three base restriction endonuclease R.CviJI from eukaryotic Chlorella virus IL-3A," Nucleic Acids Research, 24(13): 2463-2469.
TIGR Microbial Database, filed in the Opposition against EP1645631, dated Jun. 20, 2012, 14 pages.
U.S. Appl. No. 60/647,911, "GNA 1870-based vesicle vaccines for broad spectrum protection against diseases caused by Neisseria meningitidis," filed Jan. 27, 2005.
Vesikari et al. (2013). "Immunogenicity and safety of an investigational multicomponent, recombinant, meningococcal serogroup B vaccine (4CMenB) administered concomitantly with routine infant and child vaccinations: results of two randomized trials," Lancet 381:625-35.
Voulhoux and Tommassen (2002). "Transport of lipoproteins to the cell surface in Neisseria meningitidis," 13th International Pathogenic Neisseria Conference 2002, p. 31.
Written Submission to Oral Proceedings, filed in opposition against EP1976990, dated Jul. 24, 2013, 11 pages.
Zollinger et al. (2010). "Design and evaluation in mice of a broadly protective meningococcal group B native outer membrane vesicle vaccine," Vaccine, 28(31):5057-5067.
Alignment of SEQ ID No: 19 of EP2327719 against SEQ ID Nos: 92, 94, 96, 98, 100, 102, 104, 106, and 108 of WO/2003/063766, filed in opposition against EP2327719, submitted May 20, 2015, 9 pages.
Alignment of SEQ ID No: 42 of EP2258716 against SEQ ID No: 41 of EP2258716, filed in opposition against EP2258716, submitted Apr. 16, 2015, 1 page.
Alignment of SEQ ID No: 42 of EP2258716 against SEQ ID Nos: 50, 52, 54, 56, 58, 60, 62, 64, 66, 68, 70, and 72 of WO/2003/063766, filed in opposition against EP2258716, submitted Apr. 16, 2015, 12 pages.
Amended Defence and Counterclaim, Jul. 24, 2015, Claim No. HP-2015-000022, *Glaxosmithkline UK LTD* v. *Wyeth Holdings LLC*, 4 pages.
Annex 1 to the Amended Defence and Counterclaim, Jun. 24, 2015, Claim No. HP-2015000022, *Glaxosmithkline UK LTD* v. *Wyeth Holdings LLC*, 40 pages.
Brendish and Read. (2015). "Neisseria meningitidis serogroup B bivalent factor H binding protein vaccine," Expert Rev. Vaccines, 14(4):493-503.
CECMED (Dec. 2, 2011), "Resumen de las Caracteristicas del Producto: VA-MENGOC-BC," Ministerio de Salud Publica de Cuba, 4 pages. (3 page English translation included).
Claimants Amended Grounds of Invalidity under CPR 17.1 (2)(a) on Jul. 16, 2015, in respect of European Patent (UK) No. 2,343,308. In the High Court of Justice Chancery Division Patents Court, between GlaxoSmithKline UK Limited and Wyeth Holdings LLC. 9 pages.

(56) References Cited

OTHER PUBLICATIONS de Moraes JC, et al. (1992). Protective efficacy of a serogroup B meningococcal vaccine in Sao Paulo, Brazil. Lancet 340: 1074-1078.
Debbag et al. (1994). "Evaluacion de las reacciones adversas asociadas con la vacuna antimeningococcica BC. Informe perliminar sobre 8,117 vacunados." Rev Hosp Ninos BAires, No. 158/159, 6 pages. (6 page English translation included).
Decision revoking EP1737486, filed in opposition against EP1737486, dated Oct. 28, 2015, 28 pages.
Experimental Report, Submitted on Mar. 23, 2015, filed in relation to EP2411048, 2 page.
Galeano et al. (1995). "Efectividad de una vacuna antimeningococcica en una cohorte de itagui, Colombia, 1995," Epidemiologico de Antioquia 20(2), 8 pages. (9 page English translation included).
Gil et al. (2009). "Proteomic study via a non-gel based approach of meningococcal outer membrane vesicle vaccine obtained from strain CU385," Human Vaccines 5(5):347-356.
Notice of opposition, filed in opposition against EP2258716, dated Apr. 16, 2015, 12 pages.
Notice of opposition, filed in opposition against EP2327719, dated May 20, 2015, 14 pages.
Novartis internal data, filed in relation to EP1902726, submitted on Apr. 13, 2015, 1 page.
Ochoa, Rolando (2008). "Main projects on research, development and manufacturing of human vaccines," excerpt from presentation at BioQatar Symposium 2008, 4 slides.
Patentee's response to notice of opposition, filed in opposition against EP1562983, dated Feb. 16, 2015, 9 pages.
Perez et al. (2010). "Community acquired bacterial meningitis in Cuba: a follow up of a decade," BMC Infectious Diseases 10:130, 9 pages.
Rodriguez et al. (1999). "The epidemiological impact of antimeningococal B vaccination in Cuba," Mem Inst Oswaldo Cruz 94(4):433-440.
Sierra GV, et al. (1991). Vaccine against group B Neisseria meningitidis: protection trial and mass vaccination results in Cuba. NIPH Ann 14: 195-207.
Statement of Grounds of Appeal, dated Mar. 23, 2015, filed in relation to EP2411048, 8 pages.
Statement of grounds of appeal, filed in relation to EP1902726, dated Apr. 13, 2015, 9 pages.
Submission in opposition proceedings by Carpmaels and Ransford filed in EP1737486 on Jun. 12, 2015, 2 pages.
Submission in opposition proceedings by Pfizer Inc. filed against EP1737486 on Jun. 12, 2015, 7 pages.
UniProt accession No. C0JF81, Murphy et al., Last modified on May 5, 2009. 4 pages.
U.S. Appl. No. 60/328,101, "Novel immunogenic compositions for the prevention and treatment of meningococcal disease," filed Oct. 11, 2001. 253 pages.
U.S. Appl. No. 60/406,934, "Novel immunogenic compositions for the prevention and treatment of meningococcal disease," filed Aug. 30, 2002. 190 pages.
Alignment of SEQ ID No: 42 of EP2258716 with NMA0586, submitted Jul. 29, 2016, filed in opposition against EP2258716, 1 page.
Alignment of the sequence of strain Z2491 with sequences coding for subfamily A 2086 proteins disclosed by WO 2003/063,766, filed in opposition against EP1562983 on Sep. 13, 2016, 36 pages.
Amended Defense and Counterclaim, Appendix II, UK High Court proceedings in *GlaxoSmithKline UK Limited* v. *Wyeth Holdings LLC*, dated Aug. 10, 2015, filed in opposition against EP2258716, 4 pages.
Appendix A, comparison of genes predicted within "contig295" by ORFFinder, filed in relation to EP1645631 on Aug. 15, 2016, 1 page.
Approved Judgment, dated May 12, 2016, UK High Court Decision in *GlaxoSmithKline UK Limited* v. *Wyeth Holdings LLC*, filed in opposition against EP2258716 and EP1562983, 66 pages.

Bai et al. (2011) "Recombinant protein meningococcal serogroup B vaccine combined with outer membrane vesicles." Expert Opin Biol Ther. 11:969-85.
Beernink et al. (2009) "Meningococcal factor H-binding protein variants expressed by epidemic capsular group A, W-135, and X strains from Africa." J Infect Dis 199:1360-8.
Bernfield et al. (2002). "Identification of a novel vaccine candidate for group B Neisseria meningitidis," 13th International Pathogenic Neisseria Conference 2002, Poster, 20 pages.
Claimant's Notice of Experiments, UK High Court proceedings in *GlaxoSmithKline UK Limited* v. *Wyeth Holdings LLC*, submitted Jul. 28, 2016 in opposition proceedings against EP2258716 and EP1562983, 8 pages.
Clustal alignment of menA and menB sequences with upstream sequence, performed using Clustal on Genbank NC_003116.1 and NC_003112.2, Submitted in opposition proceedings of EP1645631 on Sep. 28, 2012. 2 pages.
Compton (1990). "Degenerate primers for DNA amplification," in "PCR Protocols: A Guide to Methods and Applications," Innis et al. (Eds.), pp. 39-45, Academic Press, San Diego.
Contig 295 from Sanger nm 'old data' ORF Finder, filed in relation to EP1645631, dated Jul. 1, 2013, 9 pages.
Contig 295 ORF Finder, filed in relation to EP1645631, dated Sep. 21, 2012, 2 pages.
Database UniProt (Feb. 6, 2007). Submitted name: Putative lipoprotein, Uniprot accession No. A1IQ30, PIR No. G81977, retrieved Jan. 20, 2016 from <http://www.uniprot.org/uniprot/A1IQ30>, 7 pages.
Decision of Technical Board of Appeal for EP942983, dated Nov. 14, 2013, filed in relation to EP1645631, 28 pages.
Declaration by Prof. Paul Dunman, Ph.D., dated Sep. 13, 2011, submitted in opposition proceedings for EP1801219, 10 pages.
Declaration of Robert Donald, filed in opposition against EP1562983, dated Sep. 12, 2016, 3 pages.
Don et al. (1991). "'Touchdown' PCR to circumvent spurious priming during gene amplification," Nucleic Acids Res. 19(14):4008.
Extracts from Expert Report of Professor John Heckels, UK High Court proceedings in *GlaxoSmithKline UK Limited* v. *Wyeth Holdings LLC*, dated Jan. 11, 2016, filed in opposition against EP2258716 and EP1562983, 8 pages.
Farley et al. (2002). "Characterization, cloning and expression of different subfamilies of the ORF 2086 gene from Neisseria meningitidis," 13th International Pathogenic Neisseria Conference 2002, Poster, 15 pages.
Fourth declaration of Julian Parkhill, filed in Relation to EP1645631, dated Aug. 25, 2016, 6 pages.
Further submissions by patentee, dated Feb. 3, 2016, filed in relation to EP1645631 appeal, 9 pages.
Further Submissions in the opposition against EP1801219, filed on behalf of Pfizer Inc. dated Jul. 14, 2016. 3 pages.
Gorringe & Pajon (2012) "Bexsero: a multicomponent vaccine for prevention of meningococcal disease." Human Vaccines & Immunotherapeutics 8:1-10.
Great Britain patent application No. 0227346.4, filed Nov. 22, 2003, entitled "741," by applicant Chiron SpA.
Hansjörg et al. (1996). "Peptide Based Vaccines," in "Concepts in Vaccine Development," Kaufmann (Ed.), pp. 303-326, De Gruyter.
Kimura et al. (2011) "Immunogenicity and Safety of a Multicomponent Meningococcal Serogroup B Vaccine and a Quadrivalent Meningococcal CRM197 Conjugate Vaccine against Serogroups A, C, W-135, and Y in Adults Who Are at Increased Risk for Occupational Exposure to Meningococcal Isolates" Clin. Vaccine Immunol. 18(3):483-486.
Lee et al. (1990). "cDNA Cloning Using Degenerate primers," in "PCR Protocols: A Guide to Methods and Applications," Innis et al. (Eds.), pp. 46-53, Academic Press, San Diego.
NMA0586 (D79b), filed in relation to EP1645631 on Sep. 2, 2016, 9 pages.
Notice of Opposition against EP1801219, filed on behalf of Pfizer Inc. dated Jul. 14, 2016. 54 pages.
Notice of opposition against EP2343308, filed in opposition against EP1562983, submitted Jan. 11, 2016, 21 pages.

(56) References Cited

OTHER PUBLICATIONS

Ochman et al. (1990). "Amplification of flanking sequences by inverse PCR," in "PCR Protocols: A Guide to Methods and Applications," Innis et al. (Eds.), pp. 219-227, Academic Press, San Diego.
Opponent's Response to the Patentee's Grounds of Appeal, filed in the Opposition against EP1737486 on Jul. 20, 2016, 19 pages.
ORF Finder result for NMB1870 sequence with upstream sequence, chromosome ASM880v1, accessed Sep. 27, 2012, submitted in the opposition proceedings for EP1801219. 2 pages.
Pfizer observations, filed in opposition against EP1562983, dated Apr. 27, 2012, 7 pages.
Pfizer observations, filed in opposition against EP1562983, dated May 12, 2011, 7 pages.
Pfizer's submissions in opposition against EP2343308, dated May 2, 2016, filed in opposition against EP1562983, 33 pages.
Priority document for U.S. Appl. No. 60/162,616, filed Oct. 29, 1999. 1 page.
PSORT analysis of the sequence related to orf741 from the 'second' ATG, "D5 / D20 / D20A OrfRF", accessed Jun. 21, 2012, submitted in the opposition proceedings for EP1801219. 1 page.
PSORT analysis of the sequence related to orf741 from the 'second' ATG, "MENB 'Second' ATG Start" accessed Sep. 27, 2012, submitted in the opposition proceedings for EP1801219. 1 page.
Response by opponent, filed in opposition against EP1562983, dated Jan. 11, 2016, 12 pages.
Response by patentee, dated Jul. 28, 2016, filed in opposition against EP1562983, 4 pages.
Response to Notice of Opposition by Novartis Vaccines and Diagnostics SRL for EP2327719, dated Jan. 6, 2016. 10 pages.
Result from "Hphob. / Hopp & Woods" using the SEQ ID NO: 4 and SEQ ID N0:6 from WO99/57280, accessed Jul. 13, 2016, submitted in the opposition proceedings for EP1801219. 4 pages.
Sequence NMA0586 from "'741 ORF found using Sanger sequence with ORFFinder", with upstream sequence from Bacterial Emsembl, Submitted in the opposition proceedings of EP1801219 on Jul. 14, 2016. 2 pages.
Statement of grounds of appeal, dated Mar. 7, 2016, filed in relation to EP1737486, 9 pages.
Submissions by opponent, Wyeth LLC, filed in relation to EP1645631, dated Sep. 1, 2016, 19 pages.
Response to Notice of Opposition, filed in opposition against EP2258716, dated Dec. 3, 2015, 8 pages.
Submissions by patentee, GlaxoSmithKline Biologicals SA, filed in relation to EP1645631 on Aug. 15, 2016, 16 pages.
Supplementary material Table and Figure for "NM0586" of Parkhill et al., 2000, Nature. 28 pages.
Statement of Grounds of Appeal, filed in relation to EP2353608, dated Jul. 22, 2015, 8 pages.
Sworn Statement in EP1645631 from Isabel Delany, signed Feb. 1, 2016.2 pages.
Written Submissions from the Patentee, GlaxoSmithKline Biologicals SA for EP1645631, dated Feb. 3, 2016, 10 pages.
U.S. Appl. No. 61/358,816, "Combinations of Meningococcal Factor H Binding Proteins," filed Jun. 25, 2010. 48 pages.
Zhou et al. (2000). "Universal TA cloning," Curr Issues Mol Biol. 2(1):1-7.

* cited by examiner

MENINGOCOCCAL FHBP POLYPEPTIDES

RELATED APPLICATIONS

This application is the U.S. National Phase of International Application No. PCT/M2009/005038, filed Feb. 20, 2009 and published in English, which claims priority to U.S. Provisional Application No. 61/066,711 filed Feb. 21, 2008. The teachings of the above applications are incorporated in their entirety by reference.

INCORPORATION BY REFERENCE OF MATERIAL IN THE TEXT FILE This application incorporates by reference the Sequence Listing contained in the text fife, containing the following file:

File name: 52506_Seqlist.TXT: created Sep. 29, 2010; 171 KB in size.

TECHNICAL FIELD

This invention is in the field of immunisation and, in particular, immunisation against diseases caused by pathogenic bacteria in the genus Neisseria, such as *N. meningitidis* (meningococcus).

BACKGROUND ART

*Neisseria meningitidis* is a Gram-negative encapsulated bacterium which colonises the upper respiratory tract of approximately 10% of human population. Although polysaccharide and conjugate vaccines are available against serogroups A, C, W135 and Y, this approach cannot be applied to serogroup B because the capsular polysaccharide is a polymer of polysialic acid, which is a self antigen in humans. To develop a vaccine against serogroup B, surface-exposed proteins contained in outer membrane vesicles (OMVs) have been used. These vaccines elicit serum bactericidal antibody responses and protect against disease, but they fail to induce cross-strain protection [1]. Some workers are therefore focusing on specific meningococcal antigens for use in vaccines [2].

One such antigen is the meningococcal factor H binding protein (fHBP), also known as protein '741' [SEQ IDs 2535 & 2536 in ref. 3; SEQ ID 1 herein], 'NMB1870', 'GNA1870' [refs. 4-6, following ref. 2], T2086', 'LP2086' or 'ORF2086' [7-9]. This lipoprotein is expressed across all meningococcal serogroups and has been found in multiple meningococcal strains. fHBP sequences have been grouped into three families [4] (referred to herein as families I, II & III), and it has been found that serum raised against a given family is bactericidal within the same family, but is not active against strains which express one of the other two families i.e. there is intra-family cross-protection, but not inter-family cross-protection.

To achieve cross-strain protection using fHBP, therefore, more than one family is used. To avoid the need to express and purify separate proteins, it has been proposed to express different families as hybrid proteins [10-12], including two or three of the families in a single polypeptide chain. References 13 and 14 describe various mutagenesis-based approaches for modifying fHBP sequences to increase their coverage across families I, II and III.

It is an object of the invention to provide further and improved approaches for overcoming the family specificity of protection afforded by fHBP, and to use these approaches for providing immunity against meningococcal disease and/or infection, particularly for serogroup B.

DISCLOSURE OF THE INVENTION

Full-length fHBP has the following amino acid sequence (SEQ ID NO: 1) in strain MC58:

MNRTAFCCLSLTTALILTACSSGGGGVAADIGAGLADALTAPLDHKD
KGLQSLTLDQSVRKNEKLKLAAQGAEKTYGNGDSLNTGKLKNDKVSR
FDFIRQIEVDGQLITLESGEFQVYKQSHSALTAFQTEQIQDSEHSGK
MVAKRQFRIGDIAGEHTSFDKLPEGGRATYRGTAFGSDDAGGKLTYT
IDFAAKQGNGKIEHLKSPELNVDLAAADIKPDGKRHAVISGSVLYNQ
AEKGSYSLGIFGGKAQEVAGSAEVKTVNGIRHIGLAAKQ

The mature lipoprotein lacks the first 19 amino acids of SEQ ID NO: 1, and the ΔG form of fHBP lacks the first 26 amino acids.

The MC58 sequence (SEQ ID NO: 1) is in fHBP family I. Antibodies elicited using the MC58 sequence have high bactericidal activity against the MC58 strain, but much lower activity against strains that express a family II or III fHBP. In some embodiments the invention relates to modified forms of fHBP, wherein the modification(s) improve the ability of the protein to elicit cross-family bactericidal antibodies. In other embodiments the invention relates to forms of fHBP which naturally elicit cross-family bactericidal antibodies.

Thus the invention provides a polypeptide comprising an amino acid sequence selected from the group consisting of SEQ ID NOs 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76 & 77. These amino acid sequences start at the residue which matches Val-27 of the MC58 sequence but include various amino acid modifications at downstream sites.

Two preferred sequences are SEQ ID NOs 20 and 23. SEQ ID NO: 76 is also preferred.

The polypeptides have the ability to induce bactericidal anti-meningococcal antibodies after administration to a host animal, and in preferred embodiments can induce antibodies that are bactericidal against strains in each of the three fHBP families I to III. Further information on bactericidal responses is given below.

The invention also provides a polypeptide comprising an amino acid sequence which has at least k % identity to SEQ ID NO: 76. The value of k may be selected from 90, 91, 92, 93, 94, 95, 96, 97, 98, 99 or more.

The invention also provides a polypeptide comprising an amino acid sequence comprising a first fragment and a second fragment of SEQ ID NO: 76, wherein said first fragment includes an epitope from within amino acids 89-154 of SEQ ID NO: 76, and said second fragment includes an epitope from within amino acids 187-248 of SEQ ID NO: 76. Typically, the first and second fragments are, independently, at least 7 amino acids long e.g. 8, 10, 12, 14, 16, 18, 20, 22, 24, 26, 28, 30, 32, 24, 26, 28, 40, 45, 50, 55, 60 amino acids or more.

The invention also provides a polypeptide comprising an amino acid sequence which (i) has at least k % identity to SEQ ID NO: 76 and (ii) comprises said first and second fragments of SEQ ID NO: 76.

The invention also provides a polypeptide comprising amino acid sequence SEQ ID NO: 83, but wherein one or more of residues 127, 128, 133, 135, 136, 139, 140, 142, 144, 146, 148, 155, 156, 158, 160, 162, 166, 167, 171, 173, 179, 182, 185, 188, 190, 193, 197, 202, 204, 206, 208, 209, 210, 223, 235, 236 and/or 237 therein has been either substituted with a different amino acid or deleted. A substitution may be with the amino acid from the corresponding position in SEQ ID NO: 2. The polypeptide can elicit antibodies that can bind to both SEQ ID NO: 1 and SEQ ID NO: 2.

The invention also provides a polypeptide comprising amino acid sequence SEQ ID NO: 83, but wherein one or more of residues 146, 148, 155, 156, 158, 160, 162, 171, 173, 179, 182, 235, 236 and/or 237 therein has been either substituted with a different amino acid. A substitution may be with the amino acid from the corresponding position in SEQ ID NO: 2. The polypeptide can elicit antibodies that can bind to both SEQ ID NO: 1 and SEQ ID NO: 2.

The invention also provides a polypeptide comprising amino acid sequence SEQ ID NO: 83, but wherein one or more of residues 127, 128, 133, 135, 136, 139, 140, 141, 142, 144, 166, 167, 185, 188, 190, 193, 197, 202, 204, 206, 208, 209, 210 and/or 223 therein has been either substituted with a different amino acid or deleted. A substitution may be with the amino acid from the corresponding position in SEQ ID NO: 2. The polypeptide can elicit antibodies that can bind to both SEQ ID NO: 1 and SEQ ID NO: 2.

Polypeptides

Polypeptides of the invention can be prepared by various means e.g. by chemical synthesis (at least in part), by digesting longer polypeptides using proteases, by translation from RNA, by purification from cell culture (e.g. from recombinant expression or from *N. meningitidis* culture). etc. Heterologous expression in an *E. coli* host is a preferred expression route.

fHBP is naturally a lipoprotein in *N. meningitidis*. It has also been found to be lipidated when expressed in *E. coli* with its native leader sequence. Polypeptides of the invention may have a N-terminus cysteine residue, which may be lipidated e.g. comprising a palmitoyl group, usually forming tripalmitoyl-S-glyceryl-cysteine. In other embodiments the polypeptides are not lipidated.

A characteristic of preferred polypeptides of the invention is the ability to induce bactericidal anti-meningococcal antibodies after administration to a host animal.

Polypeptides are preferably prepared in substantially pure or substantially isolated form (i.e. substantially free from other Neisserial or host cell polypeptides) or substantially isolated form. In general, the polypeptides are provided in a non-naturally occurring environment e.g. they are separated from their naturally-occurring environment. In certain embodiments, the subject polypeptide is present in a composition that is enriched for the polypeptide as compared to a control. As such, purified polypeptide is provided, whereby purified is meant that the polypeptide is present in a composition that is substantially free of other expressed polypeptides, where by substantially free is meant that less than 90%, usually less than 60% and more usually less than 50% of the composition is made up of other expressed polypeptides.

Polypeptides can take various forms (e.g. native, fusions, glycosylated, non-glycosylated, lipidated, disulfide bridges, etc.).

SEQ ID NOs 4 to 76 do not include a N-terminus methionine. If a polypeptide of the invention is produced by translation in a biological host then a start codon is required, which will provide a N-terminus methionine in most hosts. Thus a polypeptide of the invention will, at least at a nascent stage, include a methionine residue upstream of said SEQ ID NO sequence.

In some embodiments the polypeptide has a single methionine at the N-terminus immediately followed by the SEQ ID NO sequence; in other embodiments a longer upstream sequence may be used. Such an upstream sequence may be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. His$_n$ where n=3, 4, 5, 6, 7, 8, 9, 10 or more). Other suitable N-terminal amino acid sequences will be apparent to those skilled in the art.

A polypeptide of the invention may also include amino acids downstream of the final amino acid of the SEQ ID NO sequences. Such C-terminal extensions may be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. His$_n$ where n=3, 4, 5, 6, 7, 8, 9, 10 or more), or sequences which enhance polypeptide stability. Other suitable C-terminal amino acid sequences will be apparent to those skilled in the art.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains.

Polypeptides of the invention may be attached or immobilised to a solid support.

Polypeptides of the invention may comprise a detectable label e.g. a radioactive label, a fluorescent label, or a biotin label. This is particularly useful in immunoassay techniques.

As disclosed in reference 13, fHBP can be split into three domains, referred to as A, B and C. Taking SEQ ID NO: 1, the three domains are (A) 1-119, (B) 120-183 and (C) 184-274:

MNRTAFCCLSLTTALILTACSSGGGGVAADIGAGLADALTAPLDHKD

KGLQSLTLDQSVRKNEKLKLAAQGAEKTYGNGDSLNTGKLKNDKVSR

FDFIRQIEVDGQLITLESGEFQVYKQSHSALTAFQTEQIQDSEHSGK

MVAKRQFRIGDIAGEHTSFDKLPEGGRATYRGTAFGSDDAGGKLTYT

IDFAAKQGNGKIEHLKSPELNVDLAAADIKPDGKRHAVISGSVLYNQ

AEKGSYSLGIFGGKAQEVAGSAEVKTVNGIRHIGLAAKQ

The mature form of domain 'A', from Cys-20 at its N-terminus to Lys-119, is called 'A$_{mature}$'.

Multiple fHBP sequences are known and these can readily be aligned using standard methods. By such alignments the skilled person can identify (a) domains 'A' (and 'A$_{mature}$'), 'B' and 'C' in any given fHBP sequence by comparison to the coordinates in the MC58 sequence, and (b) single residues in multiple fHBP sequences e.g. for identifying substitutions. For ease of reference, however, the domains are defined below:

Domain 'A' in a given fHBP sequence is the fragment of that sequence which, when aligned to SEQ ID NO: 1 using a pairwise alignment algorithm, starts with the amino acid aligned to Met-1 of SEQ ID NO: 1 and ends with the amino acid aligned to Lys-119 of SEQ ID NO: 1.

Domain 'A$_{mature}$' in a given fHBP sequence is the fragment of that sequence which, when aligned to SEQ ID NO: 1 using a pairwise alignment algorithm, starts with the amino acid aligned to Cys-20 of SEQ ID NO: 1 and ends with the amino acid aligned to Lys-119 of SEQ ID NO: 1.

Domain 'B' in a given fHBP sequence is the fragment of that sequence which, when aligned to SEQ ID NO: 1 using a pairwise alignment algorithm, starts with the amino acid aligned to Gln-120 of SEQ ID NO: 1 and ends with the amino acid aligned to Gly-183 of SEQ ID NO: 1.

Domain 'C' in a given fHBP sequence is the fragment of that sequence which, when aligned to SEQ ID NO: 1 using a pairwise alignment algorithm, starts with the amino acid aligned to Lys-184 of SEQ ID NO: 1 and ends with the amino acid aligned to Gln-274 of SEQ ID NO: 1.

The preferred pairwise alignment algorithm for defining the domains is the Needleman-Wunsch global alignment algorithm [15], using default parameters (e.g. with Gap opening penalty=10.0, and with Gap extension penalty=0.5, using the EBLOSUM62 scoring matrix). This algorithm is conveniently implemented in the needle tool in the EMBOSS package [16].

In some embodiments, a polypeptide of the invention is truncated to remove its domain A i.e. domain A is omitted from a SEQ ID.

In some embodiments, a polypeptide comprises an amino acid sequence as described above, except that up to 10 amino acids (i.e. 1, 2, 3, 4, 5, 6, 7, 8, 9 or 10) at the N-terminus and/or up to 10 amino acids (i.e. 1, 2, 3, 4, 5, 6, 7, 8, 9 or 10) at the C-terminus are deleted. Thus the invention provides a polypeptide comprising an amino acid sequence comprising a fragment of an amino acid sequence selected from the group consisting of SEQ ID NOs 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76 & 77, wherein said fragment is amino acids a to b of said SEQ ID, wherein a is 1, 2, 3, 4, 5, 6, 7, 8, 9, 10 or 11, and wherein b is j, j-1, j-2, j-3, j-4, j-5, j-6, j-7, j-8, j-9 or j-10 where j is the length of said SEQ ID. Longer truncations (e.g. up to 15 amino acids, up to 20 amino acids, etc.) may also be used.

Nucleic Acids

The invention provides nucleic acid encoding a polypeptide of the invention as defined above.

Nucleic acids of the invention may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

Nucleic acids of the invention can take various forms e.g. single-stranded, double-stranded, vectors, primers, probes, labelled, unlabelled, etc.

Nucleic acids of the invention are preferably in isolated or substantially isolated form.

The term "nucleic acid" includes DNA and RNA, and also their analogues, such as those containing modified backbones, and also peptide nucleic acids (PNA), etc.

Nucleic acid according to the invention may be labelled e.g. with a radioactive or fluorescent label.

The invention also provides vectors (such as plasmids) comprising nucleotide sequences of the invention (e.g. cloning or expression vectors, such as those suitable for nucleic acid immunisation) and host cells transformed with such vectors.

Bactericidal Responses

Preferred polypeptides of the invention can elicit antibody responses that are bactericidal against meningococci. Bactericidal antibody responses are conveniently measured in mice and are a standard indicator of vaccine efficacy [e.g. see end-note 14 of reference 2]. Polypeptides of the invention can preferably elicit an antibody response which is bactericidal against at least one *N. meningitidis* strain from each of at least two of the following three groups of strains:

(I) MC58, gb185 (=M01-240185), m4030, m2197, m2937, iss1001, NZ394/98, 67/00, 93/114, bz198, m1390, nge28, lnp17592, 00-241341, f6124, 205900, m198/172, bz133, gb149 (=M01-240149), nm008, nm092, 30/00, 39/99, 72/00, 95330, bz169, bz83, cu385, h44/76, m1590, m2934, m2969, m3370, m4215, m4318, n44/89, 14847.

(II) 961-5945, 2996, 96217, 312294, 11327, a22, gb013 (=M01-240013), e32, m1090, m4287, 860800, 599, 95N477, 90-18311, c11, m986, m2671, 1000, m1096, m3279, bz232, dk353, m3697, ngh38, L93/4286.

(III) M1239, 16889, gb355 (=M01-240355), m3369, m3813, ngp165.

For example, a polypeptide may elicit a bactericidal response effective against two or three of serogroup B *N. meningitidis* strains MC58, 961-5945 and M1239.

The polypeptide can preferably elicit an antibody response which is bactericidal against at least 50% of clinically-relevant meningococcal serogroup B strains (e.g. 60%, 70%, 80%, 90%, 95% or more). The polypeptide may elicit an antibody response which is bactericidal against strains of serogroup B *N. meningitidis* and strains of at least one (e.g. 1, 2, 3, 4) of serogroups A, C, W135 and Y. The polypeptide may elicit an antibody response which is bactericidal against strains of *N. gonorrhoeae* and/or *N. cinerea*. The polypeptide may elicit a response which is bactericidal against strains from at least two of the three main branches of the dendrogram shown in FIG. 5 of reference 4.

The polypeptide may elicit an antibody response which is bactericidal against *N. meningitidis* strains in at least 2 (e.g. 2, 3, 4, 5, 6, 7) of hypervirulent lineages ET-37, ET-5, cluster A4, lineage 3, subgroup I, subgroup III, and subgroup IV-1 [17,18]. Polypeptides may additionally induce bactericidal antibody responses against one or more hyperinvasive lineages.

Polypeptides may elicit an antibody response which is bactericidal against *N. meningitidis* strains in at least at least 2 (e.g. 2, 3, 4, 5, 6, 7) of the following multilocus sequence types: ST1, ST4, ST5, ST8, ST11, ST32 and ST41 [19]. The polypeptide may also elicit an antibody response which is bactericidal against ST44 strains.

The polypeptide need not induce bactericidal antibodies against each and every MenB strain within the specified lineages or MLST; rather, for any given group of four or more strains of serogroup B meningococcus within a particular hypervirulent lineage or MLST, the antibodies induced by the composition are preferably bactericidal against at least 50% (e.g. 60%, 70%, 80%, 90% or more) of the group. Preferred groups of strains will include strains isolated in at least four of the following countries: GB, AU, CA, NO, IT, US, NZ, NL, BR, and CU. The serum preferably has a bactericidal titre of at least 1024e. $2^{10}$, $2^{11}$, $2^{13}$, $2^{14}$, $2^{15}$, $2^{16}$, $2^{17}$, $2^{18}$ or higher, preferably at least 2) i.e. the serum is able to kill at least 50% of test bacteria of a particular strain when diluted 1:1024 e.g. as described in end-note 14 of reference 2. Preferred chimeric polypeptides can elicit an antibody response in mice that remains bactericidal even when the serum is diluted 1:4096 or further.

Immunisation

Polypeptides of the invention may be used as the active ingredient of immunogenic compositions, and so the invention provides an immunogenic composition comprising a polypeptide of the invention.

The invention also provides a method for raising an antibody response in a mammal, comprising administering an immunogenic composition of the invention to the mammal. The antibody response is preferably a protective and/or bactericidal antibody response. The invention also provides polypeptides of the invention for use in such methods.

The invention also provides a method for protecting a mammal against a Neisserial (e.g. meningococcal) infection, comprising administering to the mammal an immunogenic composition of the invention.

The invention provides polypeptides of the invention for use as medicaments (e.g. as immunogenic compositions or as vaccines) or as diagnostic reagents. It also provides the use of nucleic acid, polypeptide, or antibody of the invention in the manufacture of a medicament for preventing Neisserial (e.g. meningococcal) infection in a mammal.

The mammal is preferably a human. The human may be an adult or, preferably, a child. Where the vaccine is for prophylactic use, the human is preferably a child (e.g. a toddler or infant); where the vaccine is for therapeutic use, the human is preferably an adult. A vaccine intended for children may also be administered to adults e.g. to assess safety, dosage, immunogenicity, etc.

The uses and methods are particularly useful for preventing/treating diseases including, but not limited to, meningitis (particularly bacterial, such as meningococcal, meningitis) and bacteremia.

Efficacy of therapeutic treatment can be tested by monitoring Neisserial infection after administration of the composition of the invention. Efficacy of prophylactic treatment can be tested by monitoring immune responses against fHBP after administration of the composition. Immunogenicity of compositions of the invention can be determined by administering them to test subjects (e.g. children 12-16 months age, or animal models [20]) and then determining standard parameters including serum bactericidal antibodies (SBA) and ELISA titres (GMT). These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is about 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

The immunogenic composition of the invention will generally include a pharmaceutically acceptable carrier, which can be any substance that does not itself induce the production of antibodies harmful to the patient receiving the composition, and which can be administered without undue toxicity. Pharmaceutically acceptable carriers can include liquids such as water, saline, glycerol and ethanol. Auxiliary substances, such as wetting or emulsifying agents, pH buffering substances, and the like, can also be present in such vehicles. A thorough discussion of suitable carriers is available in ref. 21.

Neisserial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops.

The composition is preferably sterile. It is preferably pyrogen-free. It is preferably buffered e.g. at between pH 6 and pH 8, generally around pH 7. Where a composition comprises an aluminium hydroxide salt, it is preferred to use a histidine buffer [22]. Compositions of the invention may be isotonic with respect to humans.

Immunogenic compositions comprise an immunologically effective amount of immunogen, as well as any other of other specified components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses). The composition may be administered in conjunction with other immunoregulatory agents.

Adjuvants which may be used in compositions of the invention include, but are not limited to:

A. Mineral-containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref 23], or mixtures of different mineral compounds, with the compounds taking any suitable form (e.g. gel, crystalline, amorphous, etc.), and with adsorption being preferred. The mineral containing compositions may also be formulated as a particle of metal salt [24].

A useful aluminium phosphate adjuvant is amorphous aluminium hydroxyphosphate with $PO_4/Al$ molar ratio between 0.84 and 0.92, included at 0.6 mg $Al^{3+}$/ml.

B. Oil Emulsions

Oil emulsion compositions suitable for use as adjuvants in the invention include squalene-in-water emulsions, such as MF59 [Chapter 10 of ref. 23; see also ref 25] (5% Squalene, 0.5% TWEEN 80™, and 0.5% SPAN 85™, formulated into submicron particles using a microfluidizer). Complete Freund's adjuvant (CFA) and incomplete Freund's adjuvant (IFA) may also be used.

Useful oil-in-water emulsions typically include at least one oil and at least one surfactant, with the oil(s) and surfactant(s) being biodegradable (metabolisable) and biocompatible. The oil droplets in the emulsion are generally less than 1 μm in diameter, with these small sizes being achieved with a microfluidiser to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the TWEENS™), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (TRITON X-100™, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the TERGITOL™ NP series; polyoxyethylene fatty ethers derived from lauryl, cetyl, stearyl and oleyl alcohols (known as BRIJ™ surfactants), such as triethyleneglycol monolauryl ether (BRIJ 30™); and sorbitan esters (commonly known as the SPANs™), such as sorbitan trioleate (SPAN 85™) and sorbitan monolaurate. Non-ionic surfactants are preferred. Preferred surfactants for including in the emulsion are TWEEN 80™ (polyoxyethylene sorbitan monooleate), SPAN 85™(sorbitan trioleate), lecithin and TRITON X-100™.

Mixtures of surfactants can be used e.g. TWEEN 80™/SPAN 85™ mixtures. A combination of a polyoxyethylene sorbitan ester such as polyoxyethylene sorbitan monooleate (TWEEN 80™) and an octoxynol such as t-octylphenoxypolyethoxyethanol ( TRITON X-100™) is also suitable. Another useful combination comprises laureth 9 plus a polyoxyethylene sorbitan ester and/or an octoxynol.

Preferred amounts of surfactants (% by weight) are: polyoxyethylene sorbitan esters (such as TWEEN 80™) 0.01 to 1%, in particular about 0.1%; octyl- or nonylphenoxy polyoxyethanols (such as TRITON X-100™, or other detergents in the TRITON™ series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Preferably, substantially all (e.g. at least 90% by number) of the oil droplets have a diameter of less than 1 μm, e.g. ≤750 nm, ≤500 nm, ≤400 nm, ≤300 nm, ≤250 nm, ≤220 nm, ≤200 nm, or smaller.

One specific useful submicron emulsion of squalene, TWEEN 80™, and SPAN 85™. The composition of the emulsion by volume can be about 5% squalene, about 0.5% polysorbate 80and about 0.5% SPAN 85™. In weight terms, these ratios become 4.3% squalene, 0.5% polysorbate 80 and 0.48% SPAN 85™. This adjuvant is known as 'MF59™' [26-28], as described in more detail in Chapter 10 of ref. 29 and chapter 12 of ref. 30. The MF59™ emulsion advantageously includes citrate ions e.g. 10 mM sodium citrate buffer.

C. Saponin Formulations [Chapter 22 of Ref. 23]

Saponin formulations may also be used as adjuvants in the invention. Saponins are a heterogeneous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 31. Saponin formulations may also comprise a sterol, such as cholesterol [32].

Combinations of saponins and cholesterols can be used to form unique particles called immunostimulating complexs (ISCOMs) [chapter 23 of ref. 23]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 32-34. Optionally, the ISCOMS may be devoid of additional detergent [35].

A review of the development of saponin based adjuvants can be found in refs. 36 & 37.

D. Virosomes and Virus-like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 38-43. Virosomes are discussed further in, for example, ref. 44

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 45. Such "small particles" of 3dMPL are small enough to be sterile filtered through a 0.22 µm membrane [45]. Other non-toxic LPS derivatives include monophosphoryl lipid A mimics, such as aminoalkyl glucosaminide phosphate derivatives e.g. RC-529 [46,47].

Lipid A derivatives include derivatives of lipid A from *Escherichia coli* such as OM-174. OM-174 is described for example in refs. 48 & 49.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 50, 51 and 52 disclose possible analog substitutions e.g. replacement of guanosine with 2'-deoxy-7-deazaguanosine. The adjuvant effect of CpG oligonucleotides is further discussed in refs. 53-58.

The CpG sequence may be directed to TLR9, such as the motif GTCGTT or TTCGTT [59]. The CpG sequence may be specific for inducing a Th 1 immune response, such as a CpG-A ODN, or it may be more specific for inducing a B cell response, such a CpG-B ODN. CpG-A and CpG-B ODNs are discussed in refs. 60-62. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 59 & 63-65.

A particularly useful adjuvant based around immunostimulatory oligonucleotides is known as IC31™ [66]. Thus an adjuvant used with the invention may comprise a mixture of (i) an oligonucleotide (e.g. between 15-40 nucleotides) including at least one (and preferably multiple) CpI motifs (i.e. a cytosine linked to an inosine to form a dinucleotide), and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-(IC)$_{13}$-3' (SEQ ID NO: 81). The polycationic polymer may be a peptide comprising 11-mer amino acid sequence KLKLLLLLKLK (SEQ ID NO: 82).

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 67 and as parenteral adjuvants in ref. 68. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K$_{63}$, LT-R72, and LT-G192. The use of ADP-ribosylating toxins and detoxified derivatives thereof, particularly LT-K63 and LT-R72, as adjuvants can be found in refs. 69-76. A useful CT mutant is or CT-E29H [77]. Numerical reference for amino acid substitutions is preferably based on the alignments of the A and B subunits of ADP-ribosylating toxins set forth in ref. 78, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [79], etc.) [80], interferons (e.g. interferon-γ), macrophage colony stimulating factor, and tumor necrosis factor. A preferred immunomodulator is IL-12.

G. Bioadhesives and Mucoadhesives

Bioadhesives and mucoadhesives may also be used as adjuvants in the invention. Suitable bioadhesives include esterified hyaluronic acid microspheres [81] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [82].

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref. 23)

Examples of liposome formulations suitable for use as adjuvants are described in refs. 83-85.

J. Polyoxyethylene Ether and Polyoxyethylene Ester Formulations

Adjuvants suitable for use in the invention include polyoxyethylene ethers and polyoxyethylene esters [86]. Such formulations further include polyoxyethylene sorbitan ester surfactants in combination with an octoxynol [87] as well as polyoxyethylene alkyl ethers or ester surfactants in combination with at least one additional non-ionic surfactant such as an octoxynol [88]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 89 and 90.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 91 and 92.

The invention may also comprise combinations of aspects of one or more of the adjuvants identified above. For example, the following adjuvant compositions may be used in the invention: (1) a saponin and an oil-in-water emulsion [93]; (2) a saponin (e.g. QS21) +a non-toxic LPS derivative (e.g. 3dMPL) [94]; (3) a saponin (e.g. QS21) +a non-toxic LPS derivative (e.g. 3dMPL) +a cholesterol; (4) a saponin (e.g. QS21) +3dMPL +IL-12 (optionally +a sterol) [95]; (5) combinations of 3dMPL with, for example, QS21 and/or oil-in-water emulsions [96]; (6) SAF, containing 10% squalane, 0.4% TWEEN 80™, 5% PLURONIC™-block polymer L121, and thr-MDP, either microfluidized into a submicron emulsion or vortexed to generate a larger particle size emulsion. (7) RIBI™ adjuvant system (RAS), (Ribi Immunochem) containing 2% squalene, 0.2% TWEEN 80™, and one or more bacterial cell wall components from the group consisting of monophosphorylipid A (MPL), trehalose dimycolate (TDM), and cell wall skeleton (CWS), preferably MPL +CWS (DETOX™); and (8) one or more mineral salts (such as an aluminum salt) +a non-toxic derivative of LPS (such as 3dMPL).

Other substances that act as immunostimulating agents are disclosed in chapter 7 of ref. 23.

The use of an aluminium hydroxide and/or aluminium phosphate adjuvant is particularly preferred, and antigens are generally adsorbed to these salts. Other preferred adjuvant combinations include combinations of Th1 and Th2 adjuvants such as CpG & alum or resiquimod & alum. A combination of aluminium phosphate and 3dMPL may be used.

Further Antigenic Components

Compositions of the invention include modified fHBP sequences. It is useful if the composition should not include complex or undefined mixtures of antigens e.g. it is preferred not to include outer membrane vesicles in the composition. Polypeptides of the invention are preferably expressed recombinantly in a heterologous host and then purified.

As well as including a fHBP sequence, a composition of the invention may also include one or more further neisserial antigen(s), as a vaccine which targets more than one antigen per bacterium decreases the possibility of selecting escape mutants. Thus a composition can include a second polypeptide that, when administered to a mammal, elicits an antibody response that is bactericidal against meningococcus. The second polypeptide will not be a meningococcal fHBP, but it may be e.g. a 287 sequence, a NadA sequence, a 953 sequence, a 936 sequence, etc.

Antigens for inclusion in the compositions include polypeptides comprising one or more of:

(a) the 446 even SEQ IDs (i.e. 2, 4, 6, . . . , 890, 892) disclosed in reference 97.

(b) the 45 even SEQ IDs (i.e. 2, 4, 6, . . . , 88, 90) disclosed in reference 98;

(c) the 1674 even SEQ IDs 2-3020, even SEQ IDs 3040-3114, and all SEQ IDs 3115-3241, disclosed in reference 3;

(d) the 2160 amino acid sequences NMB0001 to NMB2160 from reference 2;

(e) a meningococcal PorA protein, of any subtype, preferably recombinantly expressed;

(f) a variant, homolog, ortholog, paralog, mutant etc. of (a) to (e); or (g) an outer membrane vesicle preparation from *N. meningitidis* [e.g. see ref 160].

In addition to Neisserial polypeptide antigens, the composition may include antigens for immunising against other diseases or infections. For example, the composition may include one or more of the following further antigens:

a saccharide antigen from *N. meningitidis* serogroup A, C, W135 and/or Y, such as the saccharide disclosed in ref 99 from serogroup C [see also ref. 100] or in ref. 101.

a saccharide antigen from *Streptococcus pneumoniae* [e.g. 102, 103, 104].

an antigen from hepatitis A virus, such as inactivated virus [e.g. 105, 106].

an antigen from hepatitis B virus, such as the surface and/or core antigens [e.g. 106, 107].

a diphtheria antigen, such as a diphtheria toxoid [e.g. chapter 3 of ref 108] e.g. the CRM$_{197}$ mutant [e.g. 109].

a tetanus antigen, such as a tetanus toxoid [e.g. chapter 4 of ref 108].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 110 & 111].

a saccharide antigen from *Haemophilus influenzae* B [e.g. 100].

polio antigen(s) [e.g. 112, 113] such as IPV.

measles, mumps and/or rubella antigens [e.g. chapters 9, 10 & 11 of ref 108].

influenza antigen(s) [e.g. chapter 19 of ref. 108], such as the haemagglutinin and/or neuraminidase surface proteins.

an antigen from *Moraxella catarrhalis* [e.g. 114].

an protein antigen from *Streptococcus agalactiae* (group B *streptococcus*) [e.g. 115, 116].

a saccharide antigen from *Streptococcus agalactiae* (group B *streptococcus*).

an antigen from *Streptococcus pyogenes* (group A *streptococcus*) [e.g. 116, 117, 118].

an antigen from *Staphylococcus aureus* [e.g. 119].

The composition may comprise one or more of these further antigens.

Toxic protein antigens may be detoxified where necessary (e.g. detoxification of pertussis toxin by chemical and/or genetic means [111]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Saccharide antigens are preferably in the form of conjugates. Carrier proteins for the conjugates are discussed in more detail below.

Antigens in the composition will typically be present at a concentration of at least 1 µg/ml each. In general, the concentration of any given antigen will be sufficient to elicit an immune response against that antigen.

Immunogenic compositions of the invention may be used therapeutically (i.e. to treat an existing infection) or prophylactically (i.e. to prevent future infection).

As an alternative to using proteins antigens in the immunogenic compositions of the invention, nucleic acid (preferably DNA e.g. in the form of a plasmid) encoding the antigen may be used.

In some embodiments a composition of the invention comprises in addition to the fHBP sequence, conjugated capsular saccharide antigens from 1, 2, 3 or 4 of meningococcus serogroups A, C, W135 and Y. In other embodiments a composition of the invention comprises in addition to the fHBP sequence, at least one conjugated pneumococcal capsular saccharide antigen.

Meningococcus Serogroups Y, W135, C and A

Current serogroup C vaccines (Menjugate™ [120,99], Meningitec™ and NeisVac-C™) include conjugated saccharides. Menjugate™ and Meningitec™ have oligosaccharide antigens conjugated to a CRM$_{197}$ carrier, whereas NeisVac-C™ uses the complete polysaccharide (de-O-acetylated) conjugated to a tetanus toxoid carrier. The Menactra™ vaccine contains conjugated capsular saccharide antigens from each of serogroups Y, W135, C and A.

Compositions of the present invention may include capsular saccharide antigens from one or more of meningococcus serogroups Y, W135, C and A, wherein the antigens are conjugated to carrier protein(s) and/or are oligosaccharides. For example, the composition may include a capsular saccharide antigen from: serogroup C; serogroups A and C; serogroups A, C and W135; serogroups A, C and Y; serogroups C, W135 and Y; or from all four of serogroups A, C, W135 and Y.

A typical quantity of each meningococcal saccharide antigen per dose is between 1 µg and 20 µg e.g. about 2.5 µg, about 4 µg, about 5 µg, or about 10 µg (expressed as saccharide).

Where a mixture comprises capsular saccharides from both serogroups A and C, the ratio (w/w) of MenA saccharide:MenC saccharide may be greater than 1 (e.g. 2:1, 3:1, 4:1, 5:1, 10:1 or higher). Where a mixture comprises capsular saccharides from serogroup Y and one or both of serogroups C and W135, the ratio (w/w) of MenY saccharide:MenW135 saccharide may be greater than 1 (e.g. 2:1, 3:1, 4:1, 5:1, 10:1 or higher) and/or that the ratio (w/w) of MenY saccharide:MenC saccharide may be less than 1 (e.g. 1:2, 1:3, 1:4, 1:5, or lower). Preferred ratios (w/w) for saccharides from serogroups A:C:W135:Y are: 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1. Preferred ratios (w/w) for saccharides from serogroups C:W135:Y are: 1:1:1; 1:1:2; 1:1:1; 2:1:1; 4:2:1; 2:1:2; 4:1:2; 2:2:1; and 2:1:1. Using a substantially equal mass of each saccharide is preferred.

Capsular saccharides may be used in the form of oligosaccharides. These are conveniently formed by fragmentation of purified capsular polysaccharide (e.g. by hydrolysis), which will usually be followed by purification of the fragments of the desired size.

Fragmentation of polysaccharides is preferably performed to give a final average degree of polymerisation (DP) in the oligosaccharide of less than 30 (e.g. between 10 and 20, preferably around 10 for serogroup A; between 15 and 25 for serogroups W135 and Y, preferably around 15-20; between 12 and 22 for serogroup C; etc.). DP can conveniently be measured by ion exchange chromatography or by colorimetric assays [121].

If hydrolysis is performed, the hydrolysate will generally be sized in order to remove short-length oligosaccharides [100]. This can be achieved in various ways, such as ultrafiltration followed by ion-exchange chromatography. Oligosaccharides with a degree of polymerisation of less than or equal to about 6 are preferably removed for serogroup A, and those less than around 4 are preferably removed for serogroups W135 and Y.

Preferred MenC saccharide antigens are disclosed in reference 120, as used in Menjugate™.

The saccharide antigen may be chemically modified. This is particularly useful for reducing hydrolysis for serogroup A [122; see below]. De-O-acetylation of meningococcal saccharides can be performed. For oligosaccharides, modification may take place before or after depolymerisation.

Where a composition of the invention includes a MenA saccharide antigen, the antigen is preferably a modified saccharide in which one or more of the hydroxyl groups on the native saccharide has/have been replaced by a blocking group [122]. This modification improves resistance to hydrolysis.

Covalent Conjugation

Capsular saccharides in compositions of the invention will usually be conjugated to carrier protein(s). In general, conjugation enhances the immunogenicity of saccharides as it converts them from T-independent antigens to T-dependent antigens, thus allowing priming for immunological memory. Conjugation is particularly useful for paediatric vaccines and is a well known technique.

Typical carrier proteins are bacterial toxins, such as diphtheria or tetanus toxins, or toxoids or mutants thereof. The CRM$_{197}$ diphtheria toxin mutant [123] is useful, and is the carrier in the PREVNAR™ product. Other suitable carrier proteins include the *N. meningitidis* outer membrane protein complex [124], synthetic peptides [125,126], heat shock proteins [127,128], pertussis proteins [129,130], cytokines [131], lymphokines [131], hormones [131], growth factors [131], artificial proteins comprising multiple human CD4$^+$T cell epitopes from various pathogen-derived antigens such as N19 [133], protein D from *H. influenzae* [134-136], pneumolysin [137] or its non-toxic derivatives [138], pneumococcal surface protein PspA [139], iron-uptake proteins [140], toxin A or B from *C. difficile* [141], recombinant *P. aeruginosa* exoprotein A (rEPA) [142], etc.

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [143,144, etc.]). Other suitable techniques use carbodiimides, hydrazides, active esters, norborane, p-nitrobenzoic acid, N-hydroxysuccinimide, S-NHS, EDC, TSTU, etc.

Linkages via a linker group may be made using any known procedure, for example, the procedures described in references 145 and 146. One type of linkage involves reductive amination of the polysaccharide, coupling the resulting amino group with one end of an adipic acid linker group, and then coupling a protein to the other end of the adipic acid linker group [147,148]. Other linkers include B-propionamido [149], nitrophenyl-ethylamine [150], haloacyl halides [151], glycosidic linkages [152], 6-aminocaproic acid [153], ADH [154], $C_4$ to $C_{12}$ moieties [155] etc. As an alternative to using a linker, direct linkage can be used. Direct linkages to the protein may comprise oxidation of the polysaccharide followed by reductive amination with the protein, as described in, for example, references 156 and 157.

A process involving the introduction of amino groups into the saccharide (e.g. by replacing terminal =O groups with —NH)) followed by derivatisation with an adipic diester (e.g. adipic acid N-hydroxysuccinimido diester) and reaction with carrier protein is preferred. Another preferred reaction uses CDAP activation with a protein D carrier e.g. for MenA or MenC.

Outer Membrane Vesicles

It is preferred that compositions of the invention should not include complex or undefined mixtures of antigens, which are typical characteristics of OMVs. However, the invention can be used in conjunction with OMVs, as fHBP has been found to enhance their efficacy [6], in particular by over-expressing the polypeptides of the invention in the strains used for OMV preparation.

This approach may be used in general to improve preparations of *N. meningitidis* serogroup B microvesicles [158], 'native OMVs' [159], blebs or outer membrane vesicles [e.g. refs. 160 to 165, etc.]. These may be prepared from bacteria which have been genetically manipulated [166-169] e.g. to increase immunogenicity (e.g. hyper-express immunogens), to reduce toxicity, to inhibit capsular polysaccharide synthesis, to down-regulate PorA expression, etc. They may be prepared from hyperblebbing strains [170-173]. Vesicles from a non-pathogenic *Neisseria* may be included [174]. OMVs may be prepared without the use of detergents [175,176]. They may express non-Neisserial proteins on their surface [177]. They may be LPS-depleted. They may be mixed with recombinant antigens [160,178]. Vesicles from bacteria with different class I outer membrane protein subtypes may be used e.g. six different subtypes [179,180] using two different genetically-engineered vesicle populations each displaying three subtypes, or nine different subtypes using three different genetically-engineered vesicle populations each displaying three subtypes, etc. Useful subtypes include: P1.7,16; P1.5-1, 2-2; P1,19,15-1; P1.5-2, 10; P1.12-1,13; P1.7-2,4; P1.22,14; P1.7-1,1; P1.18-1,3,6.

Further details are given below.

Protein Expression

Bacterial expression techniques are known in the art. A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) Nature 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EP-A-0036776 and EP-A-0121775]. The β-lactamase (bla) promoter system [Weissmann (1981) "The cloning of interferon and other mistakes." In *Interferon* 3 (ed. I. Gresser)], bacteriophage lambda PL [Shimatake et al. (1981) *Nature* 292:128] and T5 [U.S. Pat. No. 4,689,406] promoter systems also provide useful promoter sequences. Another promoter of interest is an inducible arabinose promoter (pBAD).

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551, 433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad.*

*Sci.* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *Proc Natl. Acad. Sci.* 82:1074]. In addition, a hybrid promoter can also be comprised of a bacteriophage promoter and an *E. coli* operator region (EP-A-0 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli*." In *Molecular Cloning: A Laboratory Manual]*.

A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EP-A-0219237).

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (e.g. plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (EP-A-0127328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia, the following bacteria: *Bacillus subtilis* [Palva et al. (1982) *Proc. Natl. Acad. Sci. USA* 79:5582; EP-A-0036259 and EP-A-0063953; WO84/04541], *Escherichia coli* [Shimatake et al. (1981) *Nature* 292:128; Amann et al. (1985) *Gene* 40:183; Studier et al. (1986) *J. Mol. Biol.* 189:113; EP-A-0 036 776, EP-A-0 136 829 and EP-A-0 136 907], *Streptococcus cremoris* [Powell et al. (1988) Appl. Environ. Microbiol. 54:655]; *Streptococcus lividans* [Powell et al. (1988) *Appl. Environ. Microbiol.* 54:655], *Streptomyces lividans* [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g. [Masson et al. (1989) *FEMS Microbiol. Lett.* 60:273; Palva et al. (1982) *Proc. Natl. Acad. Sci. USA* 79:5582; EP-A-0036259 and EP-A-0063953; WO84/04541, *Bacillus*], [Miller et al. (1988) *Proc. Natl. Acad. Sci.* 85:856; Wang et al. (1990) *J. Bacteriol.* 172:949, *Campylobacter*], [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering Proceedings of the International Symposium on Genetic Engineering* (eds. H. W. Boyer and S, Nicosia); Mandel et al. (1970) *J. Mol. Biol.* 53:159; Taketo (1988) *Biochim. Biophys. Acta* 949:318; *Escherichia*], [Chassy et al. (1987) *FEMS Microbiol. Lett.* 44:173 *Lactobacillus*]; [Fiedler et al. (1988) *Anal. Biochem* 170:38, *Pseudomonas*]; [Augustin et al. (1990) *FEMS Microbiol. Lett.* 66:203, *Staphylococcus*], [Barany et al. (1980) *J. Bacteriol.* 144:698; Harlander (1987) "Transformation of *Streptococcus* lactic by electroporation, in: *Streptococcal Genetics* (ed. J. Ferretti and R. Curtiss III); Perry et al. (1981) *Infect. Immun.* 32:1295; Powell et al. (1988) *Appl. Environ. Microbiol.*

54:655; Somkuti et al. (1987) *Proc.* 4th Evr. Cong. Biotechnology 1:412, *Streptococcus].*

Host Cells

The invention provides a bacterium which expresses a polypeptide of the invention. The bacterium may be a meningococcus. The bacterium may constitutively express the polypeptide, but in some embodiments expression may be under the control of an inducible promoter. The bacterium may hyper-express the polypeptide (cf. ref. 181). Expression of the polypeptide may not be phase variable.

The invention also provides outer membrane vesicles prepared from a bacterium of the invention. It also provides a process for producing vesicles from a bacterium of the invention. Vesicles prepared from these strains preferably include the polypeptide of the invention, which should be in an immunoaccessible form in the vesicles i.e. an antibody which can bind to purified polypeptide of the invention should also be able to bind to the polypeptide which is present in the vesicles.

These outer membrane vesicles include any proteoliposomic vesicle obtained by disruption of or blebbling from a meningococcal outer membrane to form vesicles therefrom that include protein components of the outer membrane. Thus the term includes OMVs (sometimes referred to as 'blebs'), microvesicles (MVs [182]) and 'native OMVs' ('NOMVs' [183]).

MVs and NOMVs are naturally-occurring membrane vesicles that form spontaneously during bacterial growth and are released into culture medium. MVs can be obtained by culturing *Neisseria* in broth culture medium, separating whole cells from the smaller MVs in the broth culture medium (e.g. by filtration or by low-speed centrifugation to pellet only the cells and not the smaller vesicles), and then collecting the MVs from the cell-depleted medium (e.g. by filtration, by differential precipitation or aggregation of MVs, by high-speed centrifugation to pellet the MVs). Strains for use in production of MVs can generally be selected on the basis of the amount of MVs produced in culture e.g. refs. 184 & 185 describe *Neisseria* with high MV production.

OMVs are prepared artificially from bacteria, and may be prepared using detergent treatment (e.g. with deoxycholate), or by non-detergent means (e.g. see reference 186). Techniques for forming OMVs include treating bacteria with a bile acid salt detergent (e.g. salts of lithocholic acid, chenodeoxycholic acid, ursodeoxycholic acid, deoxycholic acid, cholic acid, ursocholic acid, etc., with sodium deoxycholate [187 & 188] being preferred for treating *Neisseria*) at a pH sufficiently high not to precipitate the detergent [189]. Other techniques may be performed substantially in the absence of detergent [186] using techniques such as sonication, homogenisation, microfluidisation, cavitation, osmotic shock, grinding, French press, blending, etc. Methods using no or low detergent can retain useful antigens such as NspA [186]. Thus a method may use an OMV extraction buffer with about 0.5% deoxycholate or lower e.g. about 0.2%, about 0.1%, <0.05% or zero.

A useful process for OMV preparation is described in reference 190 and involves ultrafiltration on crude OMVs, rather than instead of high speed centrifugation. The process may involve a step of ultracentrifugation after the ultrafiltration takes place.

Vesicles for use with the invention can be prepared from any meningococcal strain. The vesicles will usually be from a serogroup B strain, but it is possible to prepare them from serogroups other than B (e.g. reference 189 discloses a process for serogroup A), such as A, C, W135 or Y. The strain may be of any serotype (e.g. 1, 2a, 2b, 4, 14, 15, 16, etc.), any serosubtype, and any immunotype (e.g. L1; L2; L3; L3,3,7; L10; etc.). The meningococci may be from any suitable lineage, including hyperinvasive and hypervirulent lineages e.g. any of the following seven hypervirulent lineages: subgroup I; subgroup III; subgroup IV-1; ET-5 complex; ET-37 complex; A4 cluster; lineage 3.

Bacteria of the invention may, in addition to encoding a polypeptide of the invention, have one or more further modifications. For instance, they may have a modified fur gene [191]. Reference 199 teaches that nspA expression should be up-regulated with concomitant porA and cps knockout, and these modificationa msy be used. Further knockout mutants of *N. meningitidis* for OMV production are disclosed in references 199 to 201. Reference 192 discloses the construction of vesicles from strains modified to express six different PorA subtypes. Mutant *Neisseria* with low endotoxin levels, achieved by knockout of enzymes involved in LPS biosynthesis, may also be used [193,194]. These or others mutants can all be used with the invention.

Thus a strain used with the invention may in some embodiments express more than one PorA subtype. 6-valent and 9-valent PorA strains have previously been constructed. The strain may express 2, 3, 4, 5, 6, 7, 8 or 9 of PorA subtypes: P1.7,16; P1.5-1, 2-2; P1,19,15-1; P1.5-2,10; P1.12-1,13; P1.7-2,4; P1.22,14; P1.7-1,1 and/or P1.18-1,3,6. In other embodiments a strain may have been down-regulated for PorA expression e.g. in which the amount of PorA has been reduced by at least 20% (e.g. ≥30%, ≥40%, ≥50%, ≥60%, ≥70%, ≥80%, ≥90%, ≥95%, etc.), or even knocked out, relative to wild-type levels (e.g. relative to strain H44/76).

In some embodiments a strain may hyper-express (relative to the corresponding wild-type strain) certain proteins. For instance, strains may hyper-express NspA, protein 287 [195], fHBP [181], TbpA and/or TbpB [196], Cu,Zn-superoxide dismutase [196], HmbR, etc.

A gene encoding a polypeptide of the invention may be integrated into the bacterial chromosome or may be present in episomal form e.g. within a plasmid.

Advantageously for vesicle production, a meningococcus may be genetically engineered to ensure that expression of the polypeptide is not subject to phase variation. Methods for reducing or eliminating phase variability of gene expression in meningococcus are disclosed in reference 197. For example, a gene may be placed under the control of a constitutive or inducible promoter, or by removing or replacing the DNA motif which is responsible for its phase variability.

In some embodiments a strain may include one or more of the knockout and/or hyper-expression mutations disclosed in references 198 to 201. Preferred genes for down-regulation and/or knockout include: (a) Cps, CtrA, CtrB, CtrC, CtrD, FrpB, GalE, HtrB/MsbB, LbpA, LbpB, LpxK, Opa, Opc, PilC, PorB, SiaA, SiaB, SiaC, SiaD, TbpA, and/or TbpB [198]; (b) CtrA, CtrB, CtrC, CtrD, FrpB, GalE, HtrB/MsbB, LbpA, LbpB, LpxK, Opa, Opc, PhoP, PilC, PmrE, PmrF, SiaA, SiaB, SiaC, SiaD, TbpA, and/or TbpB [199]; (c) ExbB, ExbD, rmpM, CtrA, CtrB, CtrD, GalE, LbpA, LpbB, Opa, Opc, PilC, PorB, SiaA, SiaB, SiaC, SiaD, TbpA, and/or TbpB [200]; and (d) CtrA, CtrB, CtrD, FrpB, OpA, OpC, PilC, PorB, SiaD, SynA, SynB, and/or SynC [201].

Where a mutant strain is used, in some embodiments it may have one or more, or all, of the following characteristics: (i) down-regulated or knocked-out LgtB and/or GalE to truncate the meningococcal LOS; (ii) up-regulated TbpA; (iii) up-regulated NhhA; (iv) up-regulated Omp85; (v) up-regulated LbpA; (vi) up-regulated NspA; (vii) knocked-out PorA; (viii) down-regulated or knocked-out FrpB; (ix) down-regulated or knocked-out Opa; (x) down-regulated or knocked-out Opc; (xii) deleted cps gene complex. A truncated LOS can be one that does not include a sialyl-lacto-N-neotetraose epitope e.g. it might be a galactose-deficient LOS. The LOS may have no a chain.

Depending on the meningococcal strain used for preparing the vesicles, they may or may not include the strain's native fHBP antigen [202].

If LOS is present in a vesicle it is possible to treat the vesicle so as to link its LOS and protein components ("intra-bleb" conjugation [201]).

General

The term "comprising" encompasses "including" as well as "consisting" e.g. a composition "comprising" X may consist exclusively of X or may include something additional e.g. X+Y.

The term "about" in relation to a numerical value x means, for example, x+10%.

The word "substantially" does not exclude "completely" e.g. a composition which is "substantially free" from Y may be completely free from Y. Where necessary, the word "substantially" may be omitted from the definition of the invention.

"Sequence identity" is preferably determined by the Smith-Waterman homology search algorithm as implemented in the MPSRCH program (Oxford Molecular), using an affine gap search with parameters gap open penalty=12 and gap extension penalty=1.

After serogroup, meningococcal classification includes serotype, serosubtype and then immunotype, and the standard nomenclature lists serogroup, serotype, serosubtype, and immunotype, each separated by a colon e.g. B:4:P1.15:L3,7,9. Within serogroup B, some lineages cause disease often (hyperinvasive), some lineages cause more severe forms of disease than others (hypervirulent), and others rarely cause disease at all. Seven hypervirulent lineages are recognised, namely subgroups I, III and IV-1, ET-5 complex, ET-37 complex, A4 cluster and lineage 3. These have been defined by multilocus enzyme electrophoresis (MLEE), but multilocus sequence typing (MLST) has also been used to classify meningococci [ref. 19]. The four main hypervirulent clusters are ST32, ST44, ST8 and ST11 complexes.

In general, the invention does not encompass the various fHBP sequences specifically disclosed in references 4, 5, 7, 8, 9, 10, 11, 12, 13, 14 and 203.

MODES FOR CARRYING OUT THE INVENTION

With the wild-type MC58 sequence (SEQ ID NO: 1) as a baseline, 72 modified fHBP sequences have been prepared. These are shown in the sequence listing as SEQ ID NOs: 4 to 75.

Polypeptides have been expressed in E. coli with a N-terminus methionine followed immediately by a SEQ ID NO amino acid sequence. The polypeptides have been combined with Freund's complete adjuvant, MF59 or an aluminium hydroxide adjuvant and then used to immunise mice. Antisera from the mice have been tested in a bactericidal assay against a panel of ten meningococcal strains. The panel included strains from each of the three fHBP families. Wild-type MC58 polypeptide was also prepared.

Two of the polypeptides which were expressed and purified are SEQ ID NOs 79 ('PATCH_9C') and 80 ('PATCH_10A'), comprising SEQ ID NOs: 20 and 23, respectively. All of the tested polypeptides elicited sera which displayed bactericidal activity (SBA titre≥128) against at least two strains in the panel (and usually more), but the 9C and 10A polypeptides were noteworthy because their sera showed good bactericidal activity across the whole panel, including usefully against the M1239 strain. SBA titres with 9C and 10A were as follows:

| Strain | fHBP family | SEQ ID NO: 1 | | SEQ ID NO: 79 | | SEQ ID NO: 80 | |
| --- | --- | --- | --- | --- | --- | --- | --- |
| | | FCA | Al—H | MF59 | Al—H | MF59 | Al—H |
| MC58 | 1 | >32768 | 32768 | 16384 | >32768 | 2048 | 16384 |
| NM008 | 1 | 4096 | <16 | 1024 | 4096 | 64 | 128 |
| M4030 | 1 | 2048 | 256 | 4096 | 32768 | 64 | 1024 |
| GB185 | 1 | 2048 | 32 | 256 | >8192 | 512 | 2048 |
| NZ | 1 | 4096 | 128 | 256 | >8192 | 16 | 256 |
| 961-5945 | 2 | 128 | <16 | 1024 | 4096 | 4096 | 2048 |
| M3153 | 2 | 128 | <16 | 1024 | 2048 | 4096 | 4096 |
| C11 | 2 | 32 | <16 | 64 | 512 | 512 | 128 |
| M2552 | 2 | <16 | <16 | 4096 | 2048 | >8192 | 2048 |
| M1239 | 3 | 64 | <16 | <16 | 512 | 2048 | 1024 |

Thus anti-fHBP antibodies elicited by the wild-type MC58 sequence are effective against strains that express a family I fHBP, but are relatively ineffective against strains in fHBP family 2 or 3. In contrast, sera elicited by the two modified sequences are effective against a panel of strains including all three fHBP families. SEQ ID NO: 79 ('PATCH_9C') is particularly effective in this regard. In particular, in many cases the sera obtained against this polypeptide were at least as effective against the ten strains, as control sera raised against the strain's own fHBP (when using an aluminium hydroxide adjuvant). In all but one case there was no more than one dilution's decrease:

| Strain | fHBP family | Homologous fHBP | SEQ ID NO: 79 |
| --- | --- | --- | --- |
| MC58 | 1 | 32768 | >32768 |
| NM008 | 1 | no data | 4096 |
| M4030 | 1 | 256 | 32768 |
| GB185 | 1 | 2048 | >8192 |
| NZ | 1 | 2048 | >8192 |
| 961-5945 | 2 | 2048 | 4096 |
| M3153 | 2 | 2048 | 2048 |
| C11 | 2 | 1024 | 512 |

-continued

| Strain | fHBP family | Homologous fHBP | SEQ ID NO: 79 |
|---|---|---|---|
| M2552 | 2 | >8192 | 2048 |
| M1239 | 3 | 1024 | 512 |

Activity of the PATCH_9C mutant was confirmed after formulation with Freund's Complete Adjuvant (FCA) or a mixture of IC31™ with alum:

| Strain | fHBP family | FCA adjuvant | IC31 + Alum |
|---|---|---|---|
| MC58 | 1 | 8192 | >32768 |
| NM008 | 1 | 1024 | 1024 |
| M4030 | 1 | 8192 | 2048 |
| GB185 | 1 | 8192 | 4096 |
| NZ | 1 | 2048 | 4096 |
| 961-5945 | 2 | 8192 | 4096 |
| M3153 | 2 | 2048 | 4096 |
| C11 | 2 | 2048 | 1024 |
| M2552 | 2 | 2048 | 4096 |
| M1239 | 3 | 512 | 1024 |

SEQ ID NO: 77 is a fHBP sequence found in a wild-type strain ('NL096'). It is encoded by SEQ ID NO: 78. Although this is a natural sequence it does not fit well into the variants which have previously been reported. Instead, it appears to be an intermediate between families I and II. Sera raised using a ΔG form of the NL096 sequence, using two different adjuvants (FCA or aluminium hydroxide), were tested against a panel of eight strains and bactericidal titres were as follows:

| Strain | fHBP family | FCA | Al—H |
|---|---|---|---|
| NL096 | — | 8192 | 1024 |
| MC58 | 1 | ≥32768 | 2048 |
| NM008 | 1 | 4096 | 1024 |
| GB185 | 1 | ≥16384 | 2048 |
| NZ98/254 | 1 | 1024 | 256 |
| 961-5945 | 2 | >32768 | 8192 |
| M3153 | 2 | >32768 | 8192 |
| M1239 | 3 | 4096 | 256 |

Thus the NL096 polypeptide elicits antibodies that display a broad spectrum of bactericidal activity. For all of the heterologous strains except NZ98/254 the titres obtained using FCA were at least as high as the titres obtained using IC31™+alum with the PATCH_9C mutant.

It will be understood that the invention is described above by way of example only and modifications may be made whilst remaining within the scope and spirit of the invention.

References

[1] Jodar et al. (2002) *Lancet* 359(9316):1499-1508.
[2] Pizza et al. (2000) *Science* 287:1816-1820.
[3] WO99/57280.
[4] Masignani et al. (2003) *J Exp Med* 197:789-799.
[5] Welsch et al. (2004) *J Immunol* 172:5605-15.
[6] Hou et al. (2005) *J Infect Dis* 192(4):580-90.
[7] WO03/063766.
[8] Fletcher et al. (2004) *Infect Immun* 72:2088-2100.
[9] Zhu et al. (2005) *Infect Immun* 73(10):6838-45.
[10] WO01/64920.
[11] WO03/020756.
[12] WO2004/048404.
[13] WO2006/024954.
[14] WO2007/060548.
[15] Needleman & Wunsch (1970) *J. Mol. Biol.* 48, 443-453.
[16] Rice et al. (2000) *Trends Genet.* 16:276-277.
[17] Achtman (1995) *Global epidemiology of meningococcal disease*. Pages 159-175 of *Meningococcal disease* (ed. Cartwight). ISBN: 0-471-95259-1.
[18] Caugant (1998) *APMIS* 106:505-525.
[19] Maiden et al. (1998) *Proc. Natl. Acad. Sci. USA* 95:3140-3145.
[20] WO01/30390.
[21] Gennaro (2000) *Remington: The Science and Practice of Pharmacy.* 20th edition, ISBN: 0683306472.
[22] WO03/009869.
[23] *Vaccine Design* . . . (1995) eds. Powell & Newman. ISBN: 030644867X. Plenum.
[24] WO00/23105.
[25] WO90/14837.
[26] WO90/14837.
[27] Podda & Del Giudice (2003) *Expert Rev Vaccines* 2:197-203.
[28] Podda (2001) *Vaccine* 19: 2673-2680.
[29] *Vaccine Design: The Subunit and Adjuvant Approach* (eds. Powell & Newman) Plenum Press 1995 (ISBN 0-306-44867-X).
[30] *Vaccine Adjuvants: Preparation Methods and Research Protocols* (Volume 42 of *Methods in Molecular Medicine* series). ISBN: 1-59259-083-7. Ed. O'Hagan.
[31] U.S. Pat. No. 5,057,540.
[32] WO96/33739.
[33] EP-A-0109942.
[34] WO96/11711.
[35] WO00/07621.
[36] Barr et al. (1998) *Advanced Drug Delivery Reviews* 32:247-271.
[37] Sjolanderet et al. (1998) *Advanced Drug Delivery Reviews* 32:321-338.
[38] Niikura et al. (2002) *Virology* 293:273-280.
[39] Lenz et al. (2001) *J Immunol* 166:5346-5355.
[40] Pinto et al. (2003) *J Infect Dis* 188:327-338.
[41] Gerber et al. (2001) *J Virol* 75:4752-4760.
[42] WO03/024480.
[43] WO03/024481.
[44] Gluck et al. (2002) *Vaccine* 20:B10-B16.
[45] EP-A-0689454.
[46] Johnson et al. (1999) *Bioorg Med Chem Lett* 9:2273-2278.
[47] Evans et al. (2003) *Expert Rev Vaccines* 2:219-229.
[48] Meraldi et al. (2003) *Vaccine* 21:2485-2491.
[49] Pajak et al. (2003) *Vaccine* 21:836-842.
[50] Kandimalla et al. (2003) *Nucleic Acids Research* 31:2393-2400.
[51] WO02/26757.
[52] WO99/62923.
[53] Krieg (2003) *Nature Medicine* 9:831-835.
[54] McCluskie et al. (2002) *FEMS Immunology and Medical Microbiology* 32:179-185.
[55] WO98/40100.
[56] U.S. Pat. No. 6,207,646.
[57] U.S. Pat. No. 6,239,116.
[58] U.S. Pat. No. 6,429,199.
[59] Kandimalla et al. (2003) *Biochemical Society Transactions* 31 (part 3):654-658.
[60] Blackwell et al. (2003) *J Immunol* 170:4061-4068.
[61] Krieg (2002) *Trends Immunol* 23:64-65.
[62] WO01/95935.
[63] Kandimalla et al. (2003) *BBRC* 306:948-953.
[64] Bhagat et al. (2003) *BBRC* 300:853-861.
[65] WO03/035836.

[66] Schellack et al. (2006) *Vaccine* 24:5461-72.
[67] WO95/17211.
[68] WO98/42375.
[69] Beignon et al. (2002) *Infect Immun* 70:3012-3019.
[70] Pizza et al. (2001) *Vaccine* 19:2534-2541.
[71] Pizza et al. (2000) *Int J Med Microbiol* 290:455-461.
[72] Scharton-Kersten et al. (2000) *Infect Immun* 68:5306-5313.
[73] Ryan et al. (1999) *Infect Immun* 67:6270-6280.
[74] Partidos et al. (1999) *Immunol Lett* 67:209-216.
[75] Peppoloni et al. (2003) *Expert Rev Vaccines* 2:285-293.
[76] Pine et al. (2002) *J Control Release* 85:263-270.
[77] Tebbey et al. (2000) *Vaccine* 18:2723-34.
[78] Domenighini et al. (1995) *Mol Microbiol* 15:1165-1167.
[79] WO99/40936.
[80] WO99/44636.
[81] Singh et all (2001) *J Cont Release* 70:267-276.
[82] WO99/27960.
[83] U.S. Pat. No. 6,090,406.
[84] U.S. Pat. No. 5,916,588.
[85] EP-A-0626169.
[86] WO99/52549.
[87] WO01/21207.
[88] WO01/21152.
[89] Andrianov et al. (1998) *Biomaterials* 19:109-115.
[90] Payne et al. (1998) *Adv Drug Delivery Review* 31:185-196.
[91] Stanley (2002) *Clin Exp Dermatol* 27:571-577.
[92] Jones (2003) *Curr Opin Investig Drugs* 4:214-218.
[93] WO99/11241.
[94] WO94/00153.
[95] WO98/57659.
[96] European patent applications 0835318, 0735898 and 0761231.
[97] WO99/24578.
[98] WO99/36544.
[99] Costantino et al. (1992) *Vaccine* 10:691-698.
[100] Costantino et al. (1999) *Vaccine* 17:1251-1263.
[101] WO03/007985.
[102] Watson (2000) *Pediatr Infect Dis J* 19:331-332.
[103] Rubin (2000) *Pediatr Clin North Am* 47:269-285, v.
[104] Jedrzejas (2001) *Microbiol Mol Biol Rev* 65:187-207.
[105] Bell (2000) *Pediatr Infect Dis J*19:1187-1188.
[106] Iwarson (1995) *APMIS*103:321-326.
[107] Gerlich et al. (1990) *Vaccine* 8 Suppl:S63-68 & 79-80.
[108] Vaccines (1988) eds. Plotkin & Mortimer. ISBN 0-7216-1946-0.
[109] Del Guidice et al. (1998) *Molecular Aspects of Medicine* 19:1-70.
[110] Gustafsson et al. (1996) *N Engl. J. Med.* 334:349-355.
[111] Rappuoli et al. (1991) *TIBTECH* 9:232-238.
[112] Sutter et al. (2000) *Pediatr Clin North Am* 47:287-308.
[113] Zimmerman & Spann (1999) *Am Fam Physician* 59:113-118, 125-126.
[114] McMichael (2000) *Vaccine* 19 Suppl 1:S101-107.
[115] Schuchat (1999) *Lancet* 353(9146):51-6.
[116] WO02/34771.
[117] Dale (1999) *Infect Dis Clin North Am* 13:227-43, viii.
[118] Ferretti et al. (2001) *PNAS USA* 98: 4658-4663.
[119] Kuroda et al. (2001) *Lancet* 357(9264):1225-1240; see also pages 1218-1219.
[120] Jones (2001) *Curr Opin Investig Drugs* 2:47-49.
[121] Ravenscroft et al. (1999) *Vaccine* 17:2802-2816.
[122] WO03/080678.
[123] Research Disclosure, 453077 (January 2002).
[124] EP-A-0372501.
[125] EP-A-0378881.
[126] EP-A-0427347.
[127] WO93/17712.
[128] WO94/03208.
[129] WO98/58668.
[130] EP-A-0471177.
[131] WO91/01146.
[132] Falugi et al. (2001) *Eur J Immunol* 31:3816-3824.
[133] Baraldo et al. (2004) *Infect Immun* 72(8):4884-7.
[134] EP-A-0594610.
[135] Ruan et al. (1990) *J Immunol* 145:3379-3384.
[136] WO00/56360.
[137] Kuo et al. (1995) *Infect Immun* 63:2706-13.
[138] Michon et al. (1998) *Vaccine.* 16:1732-41.
[139] WO02/091998.
[140] WO01/72337.
[141] WO00/61761.
[142] WO00/33882
[143] Lees et al. (1996) *Vaccine* 14:190-198.
[144] WO95/08348.
[145] U.S. Pat. No. 4,882,317
[146] U.S. Pat. No. 4,695,624
[147] Porro et al. (1985) *Mol Immunol* 22:907-919.s
[148] EP-A-0208375
[149] WO00/10599
[150] Geyer et al. Med. Microbiol. Immunol, 165: 171-288 (1979).
[151] U.S. Pat. No. 4,057,685.
[152] U.S. Pat. Nos. 4,673,574; 4,761,283; 4,808,700.
[153] U.S. Pat. No. 4,459,286.
[154] U.S. Pat. No. 4,965,338
[155] U.S. Pat. No. 4,663,160.
[156] U.S. Pat. No. 4,761,283
[157] U.S. Pat. No. 4,356,170
[158] WO02/09643.
[159] Katial et al. (2002) *Infect Immun* 70:702-707.
[160] WO01/52885.
[161] European patent 0301992.
[162] Bjune et al. (1991) *Lancet* 338(8775):1093-1096.
[163] Fukasawa et al. (1999) *Vaccine* 17:2951-2958.
[164] WO02/09746.
[165] Rosenqvist et al. (1998) *Dev. Biol. Stand.* 92:323-333.
[166] WO01/09350.
[167] European patent 0449958.
[168] EP-A-0996712.
[169] EP-A-0680512.
[170] WO02/062378.
[171] WO99/59625.
[172] U.S. Pat. No. 6,180,111.
[173] WO01/34642.
[174] WO03/051379.
[175] U.S. Pat. No. 6,558,677.
[176] WO2004/019977.
[177] WO02/062380.
[178] WO00/25811.
[179] Peeters et al. (1996) *Vaccine* 14:1008-1015.
[180] Vermont et al. (2003) *Infect Immun* 71:1650-1655.
[181] WO2006/081259.
[182] WO02/09643.
[183] Katial et al. (2002) *Infect. Immun.* 70:702-707.
[184] U.S. Pat. No. 6,180,111.
[185] WO01/34642.
[186] WO2004/019977.
[187] European patent 0011243.
[188] Fredriksen et al. (1991) *NIPH Ann.* 14(2):67-80.
[189] WO01/91788.
[190] WO2005/004908.

[191] WO98/56901.
[192] Claassen et al. (1996) 14(10):1001-8.
[193] WO99/10497.
[194] Steeghs et al. (2001) *The EMBO Journal* 20:6937-6945.
[195] WO01/52885.
[196] WO00/25811.
[197] WO2004/015099.
[198] WO01/09350.
[199] WO02/09746.
[200] WO02/062378.
[201] WO2004/014417.
[202] WO2004/046177.
[203] WO2004/094596

Alternative Names for Sequences in the Sequence Listing

| SEQ ID NO: | Description |
|---|---|
| 1 | fHBP, strain MC58 - family I |
| 2 | fHBP, strain 961-5945 & 2996 - family II |
| 3 | fHBP, strain M1239 -family III |
| 4 | LOOP2 |
| 5 | PATCH_1 |
| 6 | PATCH_2 |
| 7 | PATCH_2S |
| 8 | PATCH_2T |
| 9 | PATCH_2FAT |
| 10 | PATCH_3 |
| 11 | PATCH_5 |
| 12 | PATCH_5bis |
| 13 | PATCH_5tris |
| 14 | PATCH_5tetra |
| 15 | PATCH_5penta |
| 16 | PATCH_8 |
| 17 | PATCH_8B |
| 18 | PATCH_9 |
| 19 | PATCH_9B |
| 20 | PATCH_9C |
| 21 | PATCH_9D |
| 22 | PATCH_9E |
| 23 | PATCH_10A |
| 24 | PATCH_10B |
| 25 | PATCH_10C |
| 26 | PATCH_10D |
| 27 | PATCH_10E |
| 28 | PATCH_10F |
| 29 | PATCH_10G |
| 30 | PATCH_10H |
| 31 | PATCH_11 |
| 32 | PATCH_11B |
| 33 | PATCH_11C |
| 34 | PATCH_11D |
| 35 | PATCH_11E |
| 36 | PATCH_11F |
| 37 | PATCH_11G |
| 38 | PATCH_11H |
| 39 | PATCH_11I |
| 40 | PATCH_11L |
| 41 | PATCH_12 |
| 42 | PATCH_12B |
| 43 | PATCH_12C |
| 44 | PATCH_12D |
| 45 | PATCH_12E |
| 46 | PATCH_12F |
| 47 | PATCH_12G |
| 48 | PATCH_12H |
| 49 | PATCH_12I |
| 50 | PATCH_12L |
| 51 | PATCH_12M |
| 52 | PATCH_12N |
| 53 | PATCH_13 |
| 54 | PATCH_13B |
| 55 | PATCH_13C |
| 56 | PATCH_14 |
| 57 | PATCH_14B |
| 58 | PATCH_14C |
| 59 | PATCH_14D |
| 60 | PATCH_15A |
| 61 | PATCH_15B |
| 62 | PATCH_16A |
| 63 | PATCH_16B |
| 64 | PATCH_16C |
| 65 | PATCH_16D |
| 66 | PATCH_16E |
| 67 | PATCH_16F |
| 68 | PATCH_16G |
| 69 | PATCH_17A |
| 70 | PATCH_17B |
| 71 | PATCH_17C |
| 72 | PATCH_18A |
| 73 | PATCH_18B |
| 74 | PATCH_18C |
| 75 | PATCH_18D |
| 76 | NL096 |
| 77 & 78 | NL096_FULL |
| 79 | Met-PATCH_9C |
| 80 | Met-PATCH_10A |
| 81 | IC31 |
| 82 | IC31 |
| 83 | aa 27-274 of SEQ 1 |

The invention claimed is:

1. An immunogenic composition comprising (a) an isolated polypeptide comprising an amino acid sequence (i) which has at least 94% sequence identity to SEQ ID NO: 76 and/or (ii) comprises a first fragment and a second fragment of SEQ ID NO: 76, wherein said first fragment includes at least 28 contiguous amino acids from within amino acids 89-154 of SEQ ID NO: 76, and said second fragment includes at least 28 contiguous amino acids from within amino acids 187-248 of SEQ ID NO: 76, and (b) an immunostimulatory amount of an aluminium salt adjuvant.

2. A plasmid comprising an isolated nucleic acid encoding a polypeptide comprising an amino acid sequence (i) which has at least 94% sequence identity to SEQ ID NO: 76 and/or (ii) comprises a first fragment and a second fragment of SEQ ID NO: 76, wherein said first fragment includes at least 28 contiguous amino acids from within amino acids 89-154 of SEQ ID NO: 76, and said second fragment includes at least 28 contiguous amino acids from within amino acids 187-248 of SEQ ID NO: 76.

3. An isolated host cell transformed with the plasmid of claim 2.

4. The host cell of claim 3, wherein the cell is a meningococcal bacterium.

5. An immunogenic composition comprising: (a) isolated membrane vesicles, wherein the vesicles include a polypeptide comprising an amino acid sequence (i) which has at least 94% sequence identity to SEQ ID NO: 76 and/or (ii) comprises a first fragment and a second fragment of SEQ ID NO: 76, wherein said first fragment includes at least 28 contiguous amino acids from within amino acids 89-154 of SEQ ID NO: 76, and said second fragment includes at least 28 contiguous amino acids from within amino acids 187-248 of SEQ ID NO: 76, and (b) an immunostimulatory amount of an aluminium salt adjuvant.

6. The immunogenic composition of claim 1 or claim 5, further comprising a second polypeptide that, when administered to a mammal, elicits an antibody response that is bactericidal against meningococcus, provided that the second polypeptide is not a meningococcal factor H binding protein (fHBP).

7. The immunogenic composition of claim 1 or claim 5, further comprising a conjugated capsular saccharide from N. meningitidis serogroup A, C, W135 and/or Y.

8. The immunogenic composition of claim 1 or claim 5, further comprising a conjugated pneumococcal capsular saccharide.

9. A method for raising an antibody response against meningococcus in a mammal, comprising administering the immunogenic composition of claim 1.

10. A method for raising an antibody response against meningococcus in a mammal, comprising administering the immunogenic composition of claim 5.

11. The immunogenic composition of claim 1, wherein the aluminium salt adjuvant is aluminium hydroxide.

12. The immunogenic composition of claim 5, wherein the aluminium salt adjuvant is aluminium hydroxide.

* * * * *

SEQUENCE LISTING

<160> NUMBER OF SEQ ID NOS: 83

<210> SEQ ID NO 1
<211> LENGTH: 274
<212> TYPE: PRT
<213> ORGANISM: Neisseria meningitidis

<400> SEQUENCE: 1

Met Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
            115                 120                 125

Gln Thr Glu Gln Ile Gln Asp Ser Glu His Ser Gly Lys Met Val Ala
            130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu
            195                 200                 205

Asn Val Asp Leu Ala Ala Ala Asp Ile Lys Pro Asp Gly Lys Arg His
210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
            260                 265                 270

Lys Gln

<210> SEQ ID NO 2
<211> LENGTH: 273
<212> TYPE: PRT
<213> ORGANISM: Neisseria meningitidis

<400> SEQUENCE: 2

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
                20                  25                  30

Ala Gly Leu Ala Asp Ala Leu Thr Ala Pro Leu Asp His Lys Asp Lys
            35                  40                  45

Ser Leu Gln Ser Leu Thr Leu Asp Gln Ser Val Arg Lys Asn Glu Lys
        50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
            130                 135                 140

Gln Arg Ser Phe Leu Val Ser Gly Leu Gly Gly Glu His Thr Ala Phe
145                 150                 155                 160

-continued

```
Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 3
<211> LENGTH: 281
<212> TYPE: PRT
<213> ORGANISM: Neisseria meningitidis

<400> SEQUENCE: 3

Met Asn Arg Thr Ala Phe Cys Cys Leu Ser Leu Thr Thr Ala Leu Ile
1               5                   10                  15

Leu Thr Ala Cys Ser Ser Gly Gly Gly Ser Gly Gly Gly Gly Gly Val
            20                  25                  30

Ala Ala Asp Ile Gly Thr Gly Leu Ala Asp Ala Leu Thr Ala Pro Leu
        35                  40                  45

Asp His Lys Asp Lys Gly Leu Lys Ser Leu Thr Leu Glu Asp Ser Ile
    50                  55                  60

Pro Gln Asn Gly Thr Leu Thr Leu Ser Ala Gln Gly Ala Glu Lys Thr
65                  70                  75                  80

Phe Lys Ala Gly Asp Lys Asp Asn Ser Leu Asn Thr Gly Lys Leu Lys
                85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
        115                 120                 125

Asn His Ser Ala Val Val Ala Leu Gln Ile Glu Lys Ile Asn Asn Pro
    130                 135                 140

Asp Lys Thr Asp Ser Leu Ile Asn Gln Arg Ser Phe Leu Val Ser Gly
145                 150                 155                 160

Leu Gly Gly Glu His Thr Ala Phe Asn Gln Leu Pro Gly Gly Lys Ala
                165                 170                 175

Glu Tyr His Gly Lys Ala Phe Ser Ser Asp Pro Asn Gly Arg Leu
            180                 185                 190

His Tyr Ser Ile Asp Phe Thr Lys Lys Gln Gly Tyr Gly Arg Ile Glu
        195                 200                 205

His Leu Lys Thr Leu Glu Gln Asn Val Glu Leu Ala Ala Ala Glu Leu
    210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255
```

Ala Gln Glu Ile Ala Gly Ser Ala Thr Val Lys Ile Gly Glu Lys Val
            260                 265                 270

His Glu Ile Gly Ile Ala Gly Lys Gln
        275                 280

<210> SEQ ID NO 4
<211> LENGTH: 250
<212> TYPE: PRT
<213> ORGANISM: Neisseria meningitidis

<400> SEQUENCE: 4

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Asn Asn Pro Asp Lys
            100                 105                 110

Ile Asp Ser Met Val Ala Lys Arg Gln Phe Arg Ile Gly Asp Ile Ala
        115                 120                 125

Gly Glu His Thr Ser Phe Asp Gln Leu Pro Asp Gly Lys Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln Leu Glu
                245                 250

<210> SEQ ID NO 5
<211> LENGTH: 248
<212> TYPE: PRT
<213> ORGANISM: Neisseria meningitidis

<400> SEQUENCE: 5

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

```
Thr Tyr Gly Asn Gly Asp Ser Leu Asn Thr Gly Lys Leu Lys Asn Asp
         50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Ile Ala
            115                 120                 125

Gly Glu His Thr Ser Phe Asp Gln Leu Pro Asp Gly Lys Arg Ala Thr
130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
            180                 185                 190

Pro Asp Gly Lys Arg His Ala Val Ile Ser Gly Ser Val Leu Tyr Asn
195                 200                 205

Gln Ala Glu Lys Gly Ser Tyr Ser Leu Gly Ile Phe Gly Gly Lys Ala
210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 6
<211> LENGTH: 248
<212> TYPE: PRT
<213> ORGANISM: Neisseria meningitidis

<400> SEQUENCE: 6

Val Ala Ala Asp Ile Gly Ala Gly Leu Ala Asp Ala Leu Thr Ala Pro
1               5                  10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Ile Ala
            115                 120                 125

Gly Glu His Thr Ser Phe Asp Lys Leu Pro Glu Gly Gly Arg Ala Thr
130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Arg Ile Glu His
```

165                 170                 175
Leu Lys Ser Pro Glu Leu Asn Val Glu Leu Ala Ala Asp Ile Lys
                180                 185                 190

Pro Asp Gly Lys Arg His Ala Val Ile Ser Gly Asp Val Arg Tyr Gly
            195                 200                 205

Gly Glu Glu Lys Gly Ser Tyr Ser Leu Gly Ile Phe Gly Gly Lys Ala
        210                 215                 220

Gln Glu Val Ala Gly Ser Ala Glu Val Lys Ile Arg Asn Gly Ile Arg
225                 230                 235                 240

His Ile Gly Leu Ala Ala Lys Gln
                245

<210> SEQ ID NO 7
<211> LENGTH: 250
<212> TYPE: PRT
<213> ORGANISM: Neisseria meningitidis

<400> SEQUENCE: 7

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Arg Ile Glu His
                165                 170                 175

Leu Lys Ser Pro Glu Leu Asn Val Glu Leu Ala Ser Ala Asp Ile Lys
            180                 185                 190

Pro Asp Gly Lys Arg His Ala Val Ile Ser Gly Asp Val Arg Tyr Gly
        195                 200                 205

Gly Glu Glu Lys Gly Ser Tyr Ser Leu Gly Ile Phe Gly Gly Lys Ala
    210                 215                 220

Gln Glu Val Ala Gly Ser Ala Glu Val Lys Ile Arg Asn Gly Ile Arg
225                 230                 235                 240

His Ile Gly Leu Ala Ala Lys Gln Leu Glu
                245                 250

<210> SEQ ID NO 8
<211> LENGTH: 248
<212> TYPE: PRT
<213> ORGANISM: Neisseria meningitidis

```
<400> SEQUENCE: 8

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Arg Ile Glu His
                165                 170                 175

Leu Lys Ser Pro Glu Leu Asn Val Glu Leu Ala Thr Ala Asp Ile Lys
            180                 185                 190

Pro Asp Gly Lys Arg His Ala Val Ile Ser Gly Asp Val Arg Tyr Gly
        195                 200                 205

Gly Glu Glu Lys Gly Ser Tyr Ser Leu Gly Ile Phe Gly Gly Lys Ala
    210                 215                 220

Gln Glu Val Ala Gly Ser Ala Glu Val Lys Ile Arg Asn Gly Ile Arg
225                 230                 235                 240

His Ile Gly Leu Ala Ala Lys Gln
                245

<210> SEQ ID NO 9
<211> LENGTH: 248
<212> TYPE: PRT
<213> ORGANISM: Neisseria meningitidis

<400> SEQUENCE: 9

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110
```

```
Ser Gly Lys Met Val Ala Lys Arg Gln Phe Arg Ile Gly Asp Ile Ala
            115                 120                 125

Gly Glu His Thr Ser Phe Asp Lys Leu Pro Glu Gly Gly Arg Ala Thr
        130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Arg Ile Glu His
                165                 170                 175

Leu Lys Ser Pro Glu Leu Asn Val Glu Leu Ala Ser Ala Asp Ile Lys
            180                 185                 190

Pro Asp Gly Lys Arg His Ala Val Ile Ser Gly Asp Val Arg Tyr Gly
        195                 200                 205

Gly Glu Glu Lys Gly Thr Tyr Ser Leu Gly Ile Phe Gly Gly Lys Ala
    210                 215                 220

Gln Glu Val Ala Gly Ser Ala Thr Val Lys Ile Arg Asn Gly Ile His
225                 230                 235                 240

Glu Ile Gly Leu Ala Ala Lys Gln
                245

<210> SEQ ID NO 10
<211> LENGTH: 248
<212> TYPE: PRT
<213> ORGANISM: Neisseria meningitidis

<400> SEQUENCE: 10

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Asn Asn Pro Asp Lys
            100                 105                 110

Ile Asp Ser Met Val Ala Lys Arg Gln Phe Arg Ile Gly Asp Ile Ala
        115                 120                 125

Gly Glu His Thr Ser Phe Asp Gln Leu Pro Asp Gly Lys Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Arg Ile Glu His
                165                 170                 175

Leu Lys Ser Pro Glu Leu Asn Val Glu Leu Ala Ser Ala Asp Ile Lys
            180                 185                 190

Pro Asp Gly Lys Arg His Ala Val Ile Ser Gly Asp Val Arg Tyr Gly
        195                 200                 205

Gly Glu Glu Lys Gly Thr Tyr Ser Leu Gly Ile Phe Gly Gly Lys Ala
    210                 215                 220

Gln Glu Val Ala Gly Ser Ala Thr Val Lys Ile Arg Asn Gly Ile Arg
225                 230                 235                 240
```

```
His Ile Gly Leu Ala Ala Lys Gln
            245
```

<210> SEQ ID NO 11
<211> LENGTH: 248
<212> TYPE: PRT
<213> ORGANISM: Neisseria meningitidis

<400> SEQUENCE: 11

```
Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ile Asp Lys Met Val Ala Lys Arg Gln Phe Arg Ile Ser Gly Ile Ala
        115                 120                 125

Gly Glu His Thr Ser Phe Asp Lys Leu Pro Glu Gly Gly Lys Ala Glu
    130                 135                 140

Tyr His Gly Lys Ala Phe Gly Ser Asp Asp Pro Asn Gly Arg Leu His
145                 150                 155                 160

Tyr Ser Ile Asp Phe Ala Ala Lys Gln Gly Asn Gly Arg Ile Glu His
                165                 170                 175

Leu Lys Ser Pro Glu Leu Asn Val Glu Leu Ala Ser Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
            245
```

<210> SEQ ID NO 12
<211> LENGTH: 248
<212> TYPE: PRT
<213> ORGANISM: Neisseria meningitidis

<400> SEQUENCE: 12

```
Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60
```

```
Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95

Ser Ala Leu Thr Ala Phe Gln Thr Glu Gln Ile Gln Asp Ser Glu His
            100                 105                 110

Thr Asp Lys Met Val Ala Lys Arg Gln Phe Arg Ile Ser Gly Ile Ala
        115                 120                 125

Gly Glu His Thr Ser Phe Asp Lys Leu Pro Glu Gly Lys Ala Glu
    130                 135                 140

Tyr His Gly Lys Ala Phe Gly Ser Asp Pro Asn Gly Arg Leu His
145                 150                 155                 160

Tyr Thr Ile Asp Phe Ala Ala Lys Gln Gly Asn Gly Arg Ile Glu His
                165                 170                 175

Leu Lys Ser Pro Glu Leu Asn Val Glu Leu Ala Ser Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 13
<211> LENGTH: 248
<212> TYPE: PRT
<213> ORGANISM: Neisseria meningitidis

<400> SEQUENCE: 13

Val Ala Ala Asp Ile Gly Ala Gly Leu Ala Asp Ala Leu Thr Ala Pro
  1               5                  10                  15

Leu Asp His Lys Asp Lys Gly Leu Gln Ser Leu Thr Leu Asp Gln Ser
             20                  25                  30

Val Arg Lys Asn Glu Lys Leu Lys Leu Ala Ala Gln Gly Ala Glu Lys
         35                  40                  45

Thr Tyr Gly Asn Gly Asp Ser Leu Asn Thr Gly Lys Leu Lys Asn Asp
     50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95

Ser Ala Leu Thr Ala Phe Gln Thr Glu Gln Ile Gln Asp Ser Glu His
            100                 105                 110

Thr Asp Lys Met Val Ala Lys Arg Gln Phe Arg Ile Ser Gly Ile Ala
        115                 120                 125

Gly Glu His Thr Ser Phe Asp Lys Leu Pro Glu Gly Lys Ala Glu
    130                 135                 140

Tyr His Gly Lys Ala Phe Gly Ser Asp Pro Asn Gly Arg Leu His
145                 150                 155                 160

Tyr Thr Ile Asp Phe Ala Ala Lys Gln Gly Tyr Gly Arg Ile Glu His
                165                 170                 175

Leu Lys Ser Pro Glu Leu Asn Val Glu Leu Ala Ser Ala Asp Ile Lys
```

```
                        180                 185                 190
Pro Asp Gly Lys Arg His Ala Val Ile Ser Gly Ser Val Leu Tyr Asn
            195                 200                 205

Gln Ala Glu Lys Gly Ser Tyr Ser Leu Gly Ile Phe Gly Gly Lys Ala
        210                 215                 220

Gln Glu Val Ala Gly Ser Ala Glu Val Lys Thr Val Asn Gly Ile Arg
225                 230                 235                 240

His Ile Gly Leu Ala Ala Lys Gln
            245

<210> SEQ ID NO 14
<211> LENGTH: 248
<212> TYPE: PRT
<213> ORGANISM: Neisseria meningitidis

<400> SEQUENCE: 14

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ile Asp Lys Met Val Ala Lys Arg Gln Phe Arg Ile Ser Gly Ile Ala
        115                 120                 125

Gly Glu His Thr Ser Phe Asp Lys Leu Pro Glu Gly Gly Lys Ala Glu
    130                 135                 140

Tyr His Gly Lys Ala Phe Gly Ser Asp Pro Asn Gly Arg Leu His Tyr
145                 150                 155                 160

Tyr Ser Ile Asp Phe Ala Ala Lys Gln Gly Tyr Gly Arg Ile Glu His
                165                 170                 175

Leu Lys Ser Pro Glu Leu Asn Val Glu Leu Ala Ser Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
            245

<210> SEQ ID NO 15
<211> LENGTH: 248
<212> TYPE: PRT
<213> ORGANISM: Neisseria meningitidis

<400> SEQUENCE: 15

Val Ala Ala Asp Ile Gly Ala Gly Leu Ala Asp Ala Leu Thr Ala Pro
```

```
            1               5                  10                 15
          Leu Asp His Lys Asp Lys Gly Leu Gln Ser Leu Thr Leu Asp Gln Ser
                          20                  25                 30

Val Arg Lys Asn Glu Lys Leu Lys Leu Ala Ala Gln Gly Ala Glu Lys
                          35                  40                  45

Thr Tyr Gly Asn Gly Asp Ser Leu Asn Thr Gly Lys Leu Lys Asn Asp
                          50                  55                  60

Lys Val Ser Arg Phe Asp Phe Ile Arg Gln Ile Glu Val Asp Gly Gln
           65                  70                  75                  80

Leu Ile Thr Leu Glu Ser Gly Glu Phe Gln Val Tyr Lys Gln Ser His
                          85                  90                  95

Ser Ala Leu Thr Ala Phe Gln Thr Glu Gln Ile Gln Asp Ser Glu His
                          100                 105                 110

Ile Asp Lys Met Val Ala Lys Arg Gln Phe Arg Ile Ser Gly Ile Ala
                          115                 120                 125

Gly Glu His Thr Ser Phe Asp Lys Leu Pro Glu Gly Gly Lys Ala Glu
                          130                 135                 140

Tyr His Gly Lys Ala Phe Gly Ser Asp Asp Ala Gly Gly Lys Leu Thr
           145                 150                 155                 160

Tyr Thr Ile Asp Phe Ala Ala Lys Gln Gly His Gly Arg Ile Glu His
                          165                 170                 175

Leu Lys Ser Pro Glu Leu Asn Val Glu Leu Ala Ala Ala Asp Ile Lys
                          180                 185                 190

Pro Asp Gly Lys Arg His Ala Val Ile Ser Gly Ser Val Leu Tyr Asn
                          195                 200                 205

Gln Ala Glu Lys Gly Ser Tyr Ser Leu Gly Ile Phe Gly Gly Lys Ala
                          210                 215                 220

Gln Glu Val Ala Gly Ser Ala Glu Val Lys Thr Val Asn Gly Ile Arg
           225                 230                 235                 240

His Ile Gly Leu Ala Ala Lys Gln
                          245

<210> SEQ ID NO 16
<211> LENGTH: 248
<212> TYPE: PRT
<213> ORGANISM: Neisseria meningitidis

<400> SEQUENCE: 16

Val Ala Ala Asp Ile Gly Ala Gly Leu Ala Asp Ala Leu Thr Ala Pro
 1               5                  10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
                35                  40                  45

Thr Tyr Gly Asn Gly Asp Ser Leu Asn Thr Gly Lys Leu Lys Asn Asp
                50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Leu Gly
                115                 120                 125
```

```
Gly Glu His Thr Ser Phe Asp Lys Leu Pro Glu Gly Gly Arg Ala Thr
        130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ser Ala Glu Ile Lys
            180                 185                 190

Ala Asp Glu Lys Ser His Ala Val Ile Leu Gly Asp Val Arg Tyr Asn
        195                 200                 205

Gln Ala Glu Lys Gly Thr Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 17
<211> LENGTH: 248
<212> TYPE: PRT
<213> ORGANISM: Neisseria meningitidis

<400> SEQUENCE: 17

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Leu Gly
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Glu Ile Lys
            180                 185                 190

Ala Asp Glu Lys Ser His Ala Val Ile Leu Gly Asp Val Arg Tyr Asn
        195                 200                 205

Gln Ala Glu Lys Gly Thr Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245
```

<210> SEQ ID NO 18
<211> LENGTH: 248
<212> TYPE: PRT
<213> ORGANISM: Neisseria meningitidis

<400> SEQUENCE: 18

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
130                 135                 140

Tyr His Gly Lys Ala Phe Gly Ser Asp Asp Pro Asn Gly Arg Leu His
145                 150                 155                 160

Tyr Ser Ile Asp Phe Ala Ala Lys Gln Gly Tyr Gly Arg Ile Glu His
                165                 170                 175

Leu Lys Thr Pro Glu Gln Asn Val Asp Leu Ala Ala Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Ile Arg Glu Gly Ile Arg
225                 230                 235                 240

His Ile Gly Leu Ala Ala Lys Gln
                245

<210> SEQ ID NO 19
<211> LENGTH: 248
<212> TYPE: PRT
<213> ORGANISM: Neisseria meningitidis

<400> SEQUENCE: 19

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val Ser Arg Phe Asp Phe Ile Arg Gln Ile Glu Val Asp Gly Gln
65                  70                  75                  80

```
Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr His Gly Lys Ala Phe Gly Ser Asp Asp Ala Gly Gly Lys Leu Thr
145                 150                 155                 160

Tyr Thr Ile Asp Phe Ala Ala Lys Gln Gly His Gly Arg Ile Glu His
                165                 170                 175

Leu Lys Thr Pro Glu Gln Asn Val Asp Leu Ala Ala Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Ile Gly Glu Gly Ile Arg
225                 230                 235                 240

His Ile Gly Leu Ala Ala Lys Gln
            245

<210> SEQ ID NO 20
<211> LENGTH: 248
<212> TYPE: PRT
<213> ORGANISM: Neisseria meningitidis

<400> SEQUENCE: 20

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr His Gly Lys Ala Phe Gly Ser Asp Asp Pro Asn Gly Arg Leu His
145                 150                 155                 160

Tyr Thr Ile Asp Phe Ala Ala Lys Gln Gly Tyr Gly Arg Ile Glu His
                165                 170                 175

Leu Lys Thr Pro Glu Gln Asn Val Asp Leu Ala Ala Ala Asp Ile Lys
            180                 185                 190

Pro Asp Gly Lys Arg His Ala Val Ile Ser Gly Ser Val Leu Tyr Asn
```

195                 200                 205
Gln Ala Glu Lys Gly Ser Tyr Ser Leu Gly Ile Phe Gly Gly Lys Ala
    210                 215                 220

Gln Glu Val Ala Gly Ser Ala Glu Val Lys Ile Gly Glu Gly Ile Arg
225                 230                 235                 240

His Ile Gly Leu Ala Ala Lys Gln
                245

<210> SEQ ID NO 21
<211> LENGTH: 248
<212> TYPE: PRT
<213> ORGANISM: Neisseria meningitidis

<400> SEQUENCE: 21

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr His Gly Lys Ala Phe Gly Ser Asp Asp Ala Gly Gly Lys Leu Thr
145                 150                 155                 160

Tyr Thr Ile Asp Phe Ala Ala Lys Gln Gly His Gly Lys Ile Glu His
                165                 170                 175

Leu Lys Thr Pro Glu Gln Asn Val Asp Leu Ala Ala Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Ile Arg Glu Gly Ile Arg
225                 230                 235                 240

His Ile Gly Leu Ala Ala Lys Gln
                245

<210> SEQ ID NO 22
<211> LENGTH: 248
<212> TYPE: PRT
<213> ORGANISM: Neisseria meningitidis

<400> SEQUENCE: 22

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser

```
                20                  25                  30
Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
               100                 105                 110

Ser Gly Lys Met Val Ala Lys Arg Gln Phe Arg Ile Gly Asp Ile Ala
               115                 120                 125

Gly Glu His Thr Ser Phe Asp Lys Leu Pro Glu Gly Gly Arg Ala Thr
               130                 135                 140

Tyr His Gly Lys Ala Phe Gly Ser Asp Asp Pro Asn Gly Arg Leu His
145                 150                 155                 160

Tyr Thr Ile Asp Phe Ala Ala Lys Gln Gly Tyr Gly Arg Ile Glu His
                165                 170                 175

Leu Lys Thr Pro Glu Gln Asn Val Asp Leu Ala Ala Ala Asp Ile Lys
                180                 185                 190

Pro Asp Gly Lys Arg His Ala Val Ile Ser Gly Ser Val Leu Tyr Asn
                195                 200                 205

Gln Ala Glu Lys Gly Ser Tyr Ser Leu Gly Ile Phe Gly Gly Lys Ala
                210                 215                 220

Gln Glu Val Ala Gly Ser Ala Glu Val Lys Ile Arg Glu Gly Ile Arg
225                 230                 235                 240

His Ile Gly Leu Ala Ala Lys Gln
                245

<210> SEQ ID NO 23
<211> LENGTH: 247
<212> TYPE: PRT
<213> ORGANISM: Neisseria meningitidis

<400> SEQUENCE: 23

Val Ala Ala Asp Ile Gly Ala Gly Leu Ala Asp Ala Leu Thr Ala Pro
 1                   5                  10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
               100                 105                 110

Ser Gly Lys Met Val Ala Lys Arg Gln Phe Arg Ile Gly Asp Leu Gly
               115                 120                 125

Gly Glu His Thr Ala Phe Asn Gln Leu Pro Asp Gly Lys Ala Glu Tyr
               130                 135                 140
```

```
Arg Gly Thr Ala Phe Gly Ser Asp Asp Ala Gly Gly Lys Leu Thr Tyr
145                 150                 155                 160

Thr Ile Asp Phe Thr Lys Lys Gln Gly Asn Gly Lys Ile Glu His Leu
            165                 170                 175

Lys Ser Pro Glu Leu Asn Val Glu Leu Ala Ser Ala Glu Ile Lys Ala
        180                 185                 190

Asp Gly Lys Ser His Ala Val Ile Leu Gly Asp Val Arg Tyr Gly Ser
        195                 200                 205

Glu Glu Lys Gly Ser Tyr Ser Leu Gly Ile Phe Gly Gly Arg Ala Gln
        210                 215                 220

Glu Val Ala Gly Ser Ala Glu Val Lys Thr Val Asn Gly Ile Arg His
225                 230                 235                 240

Ile Gly Leu Ala Ala Lys Gln
                245

<210> SEQ ID NO 24
<211> LENGTH: 247
<212> TYPE: PRT
<213> ORGANISM: Neisseria meningitidis

<400> SEQUENCE: 24

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Leu Gly
        115                 120                 125

Gly Glu His Thr Ala Phe Asn Gln Leu Pro Ser Gly Lys Ala Glu Tyr
    130                 135                 140

Arg Gly Thr Ala Phe Gly Ser Asp Asp Ala Gly Gly Lys Leu Thr Tyr
145                 150                 155                 160

Thr Ile Asp Phe Thr Lys Lys Gln Gly Asn Gly Lys Ile Glu His Leu
            165                 170                 175

Lys Ser Pro Glu Leu Asn Val Glu Leu Ala Ser Ala Glu Ile Lys Ala
        180                 185                 190

Asp Gly Lys Ser His Ala Val Ile Leu Gly Asp Val Arg Tyr Gly Gly
        195                 200                 205

Glu Glu Lys Gly Ser Tyr Ser Leu Gly Ile Phe Gly Gly Arg Ala Gln
        210                 215                 220

Glu Val Ala Gly Ser Ala Glu Val Lys Thr Val Asn Gly Ile Arg His
225                 230                 235                 240

Ile Gly Leu Ala Ala Lys Gln
                245

<210> SEQ ID NO 25
```

```
<211> LENGTH: 247
<212> TYPE: PRT
<213> ORGANISM: Neisseria meningitidis

<400> SEQUENCE: 25
```

| Val<br>1 | Ala | Ala | Asp | Ile<br>5 | Gly | Ala | Gly | Leu | Ala<br>10 | Asp | Ala | Leu | Thr | Ala<br>15 | Pro |
|---|---|---|---|---|---|---|---|---|---|---|---|---|---|---|---|
| Leu | Asp | His | Lys<br>20 | Asp | Lys | Gly | Leu | Gln<br>25 | Ser | Leu | Thr | Leu | Asp<br>30 | Gln | Ser |
| Val | Arg | Lys<br>35 | Asn | Glu | Lys | Leu | Lys<br>40 | Leu | Ala | Ala | Gln | Gly<br>45 | Ala | Glu | Lys |
| Thr | Tyr<br>50 | Gly | Asn | Gly | Asp | Ser<br>55 | Leu | Asn | Thr | Gly | Lys<br>60 | Leu | Lys | Asn | Asp |
| Lys<br>65 | Val | Ser | Arg | Phe | Asp<br>70 | Phe | Ile | Arg | Gln | Ile<br>75 | Glu | Val | Asp | Gly | Gln<br>80 |
| Leu | Ile | Thr | Leu | Glu<br>85 | Ser | Gly | Glu | Phe | Gln<br>90 | Val | Tyr | Lys | Gln | Ser<br>95 | His |
| Ser | Ala | Leu | Thr<br>100 | Ala | Phe | Gln | Thr | Glu<br>105 | Gln | Ile | Gln | Asp | Ser<br>110 | Glu | His |
| Ser | Gly | Lys<br>115 | Met | Val | Ala | Lys | Arg<br>120 | Gln | Phe | Arg | Ile | Gly<br>125 | Asp | Leu | Gly |
| Gly | Glu<br>130 | His | Thr | Ala | Phe | Asn<br>135 | Gln | Leu | Pro | Ser | Gly<br>140 | Lys | Ala | Glu | Tyr |
| Arg<br>145 | Gly | Thr | Ala | Phe | Gly<br>150 | Ser | Asp | Asp | Ala | Gly<br>155 | Gly | Lys | Leu | Thr | Tyr<br>160 |
| Thr | Ile | Asp | Phe | Ala<br>165 | Ala | Lys | Gln | Gly | Asn<br>170 | Gly | Lys | Ile | Glu | His<br>175 | Leu |
| Lys | Ser | Pro | Glu<br>180 | Leu | Asn | Val | Glu | Leu<br>185 | Ala | Ser | Ala | Glu | Ile<br>190 | Lys | Ala |
| Asp | Gly<br>195 | Lys | Ser | His | Ala | Val<br>200 | Ile | Leu | Gly | Asp | Val<br>205 | Arg | Tyr | Gly | Gly |
| Glu | Glu<br>210 | Lys | Gly | Ser | Tyr | Ser<br>215 | Leu | Gly | Ile | Phe | Gly<br>220 | Gly | Arg | Ala | Gln |
| Glu<br>225 | Val | Ala | Gly | Ser | Ala<br>230 | Glu | Val | Lys | Thr | Val<br>235 | Asn | Gly | Ile | Arg | His<br>240 |
| Ile | Gly | Leu | Ala | Ala<br>245 | Lys | Gln | | | | | | | | | |

```
<210> SEQ ID NO 26
<211> LENGTH: 247
<212> TYPE: PRT
<213> ORGANISM: Neisseria meningitidis

<400> SEQUENCE: 26
```

| Val<br>1 | Ala | Ala | Asp | Ile<br>5 | Gly | Ala | Gly | Leu | Ala<br>10 | Asp | Ala | Leu | Thr | Ala<br>15 | Pro |
|---|---|---|---|---|---|---|---|---|---|---|---|---|---|---|---|
| Leu | Asp | His | Lys<br>20 | Asp | Lys | Gly | Leu | Gln<br>25 | Ser | Leu | Thr | Leu | Asp<br>30 | Gln | Ser |
| Val | Arg | Lys<br>35 | Asn | Glu | Lys | Leu | Lys<br>40 | Leu | Ala | Ala | Gln | Gly<br>45 | Ala | Glu | Lys |
| Thr | Tyr<br>50 | Gly | Asn | Gly | Asp | Ser<br>55 | Leu | Asn | Thr | Gly | Lys<br>60 | Leu | Lys | Asn | Asp |
| Lys<br>65 | Val | Ser | Arg | Phe | Asp<br>70 | Phe | Ile | Arg | Gln | Ile<br>75 | Glu | Val | Asp | Gly | Gln<br>80 |
| Leu | Ile | Thr | Leu | Glu<br>85 | Ser | Gly | Glu | Phe | Gln<br>90 | Val | Tyr | Lys | Gln | Ser<br>95 | His |

```
Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Leu Gly
        115                 120                 125

Gly Glu His Thr Ala Phe Asn Gln Leu Pro Asp Gly Lys Ala Glu Tyr
    130                 135                 140

Arg Gly Thr Ala Phe Gly Ser Asp Asp Ala Gly Gly Lys Leu Thr Tyr
145                 150                 155                 160

Thr Ile Asp Phe Thr Lys Lys Gln Gly Asn Gly Lys Ile Glu His Leu
                165                 170                 175

Lys Ser Pro Glu Leu Asn Val Glu Leu Ala Ala Ala Glu Ile Lys Ala
            180                 185                 190

Asp Gly Lys Ser His Ala Val Ile Leu Gly Asp Val Arg Tyr Gly Ser
        195                 200                 205

Glu Glu Lys Gly Ser Tyr Ser Leu Gly Ile Phe Gly Gly Arg Ala Gln
    210                 215                 220

Glu Val Ala Gly Ser Ala Glu Val Lys Thr Val Asn Gly Ile Arg His
225                 230                 235                 240

Ile Gly Leu Ala Ala Lys Gln
                245

<210> SEQ ID NO 27
<211> LENGTH: 247
<212> TYPE: PRT
<213> ORGANISM: Neisseria meningitidis

<400> SEQUENCE: 27

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Leu Gly
        115                 120                 125

Gly Glu His Thr Ala Phe Asn Gln Leu Pro Asp Gly Lys Ala Glu Tyr
    130                 135                 140

Arg Gly Thr Ala Phe Gly Ser Asp Asp Ala Gly Gly Lys Leu Thr Tyr
145                 150                 155                 160

Thr Ile Asp Phe Thr Lys Lys Gln Gly Asn Gly Lys Ile Glu His Leu
                165                 170                 175

Lys Ser Pro Glu Leu Asn Val Glu Leu Ala Ser Ala Glu Ile Lys Ala
            180                 185                 190

Asp Gly Lys Ser His Ala Val Ile Leu Gly Asp Val Arg Tyr Gly Gly
        195                 200                 205

Glu Glu Lys Gly Ser Tyr Ser Leu Gly Ile Phe Gly Gly Arg Ala Gln
```

```
                210                 215                 220
Glu Val Ala Gly Ser Ala Glu Val Lys Thr Val Asn Gly Ile Arg His
225                 230                 235                 240

Ile Gly Leu Ala Ala Lys Gln
                245

<210> SEQ ID NO 28
<211> LENGTH: 247
<212> TYPE: PRT
<213> ORGANISM: Neisseria meningitidis

<400> SEQUENCE: 28

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Leu Gly
        115                 120                 125

Gly Glu His Thr Ala Phe Asn Gln Leu Pro Asp Gly Lys Ala Glu Tyr
130                 135                 140

Arg Gly Thr Ala Phe Gly Ser Asp Asp Ala Gly Gly Lys Leu Thr Tyr
145                 150                 155                 160

Thr Ile Asp Phe Thr Asn Lys Gln Gly Asn Gly Lys Ile Glu His Leu
                165                 170                 175

Lys Ser Pro Glu Leu Asn Val Glu Leu Ala Ser Ala Glu Ile Lys Ala
            180                 185                 190

Asp Gly Lys Ser His Ala Val Ile Leu Gly Asp Val Arg Tyr Gly Ser
        195                 200                 205

Glu Glu Lys Gly Ser Tyr Ser Leu Gly Ile Phe Gly Gly Arg Ala Gln
210                 215                 220

Glu Val Ala Gly Ser Ala Glu Val Lys Thr Val Asn Gly Ile Arg His
225                 230                 235                 240

Ile Gly Leu Ala Ala Lys Gln
                245

<210> SEQ ID NO 29
<211> LENGTH: 247
<212> TYPE: PRT
<213> ORGANISM: Neisseria meningitidis

<400> SEQUENCE: 29

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
```

```
                35                  40                  45
Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Leu Gly
                115                 120                 125

Gly Glu His Thr Ala Phe Asn Gln Leu Pro Gly Gly Lys Ala Glu Tyr
                130                 135                 140

Arg Gly Thr Ala Phe Gly Ser Asp Asp Ala Gly Gly Lys Leu Thr Tyr
145                 150                 155                 160

Thr Ile Asp Phe Ala Ala Lys Gln Gly Asn Gly Lys Ile Glu His Leu
                165                 170                 175

Lys Ser Pro Glu Leu Asn Val Glu Leu Ala Ala Ala Glu Ile Lys Ala
                180                 185                 190

Asp Gly Lys Ser His Ala Val Ile Leu Gly Asp Val Arg Tyr Gly Ser
                195                 200                 205

Glu Glu Lys Gly Ser Tyr Ser Leu Gly Ile Phe Gly Gly Arg Ala Gln
                210                 215                 220

Glu Val Ala Gly Ser Ala Glu Val Lys Thr Val Asn Gly Ile Arg His
225                 230                 235                 240

Ile Gly Leu Ala Ala Lys Gln
                245

<210> SEQ ID NO 30
<211> LENGTH: 247
<212> TYPE: PRT
<213> ORGANISM: Neisseria meningitidis

<400> SEQUENCE: 30

Val Ala Ala Asp Ile Gly Ala Gly Leu Ala Asp Ala Leu Thr Ala Pro
 1               5                  10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
                35                  40                  45

Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Leu Gly
                115                 120                 125

Gly Glu His Thr Ala Phe Asn Gln Leu Pro Gly Gly Lys Ala Glu Tyr
                130                 135                 140

Arg Gly Thr Ala Phe Gly Ser Asp Asp Ala Gly Gly Lys Leu Thr Tyr
145                 150                 155                 160
```

```
Thr Ile Asp Phe Thr Lys Lys Gln Gly Asn Gly Lys Ile Glu His Leu
                165                 170                 175

Lys Ser Pro Glu Leu Asn Val Glu Leu Ala Ser Ala Glu Ile Lys Ala
            180                 185                 190

Asp Gly Lys Ser His Ala Val Ile Leu Gly Asp Val Arg Tyr Gly Ser
        195                 200                 205

Glu Glu Lys Gly Ser Tyr Ser Leu Gly Ile Phe Gly Gly Arg Ala Gln
    210                 215                 220

Glu Val Ala Gly Ser Ala Glu Val Lys Thr Val Asn Gly Ile Arg His
225                 230                 235                 240

Ile Gly Leu Ala Ala Lys Gln
                245

<210> SEQ ID NO 31
<211> LENGTH: 248
<212> TYPE: PRT
<213> ORGANISM: Neisseria meningitidis

<400> SEQUENCE: 31

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Thr Pro Glu Leu Asn Val Asp Leu Ala Ala Ala Asp Ile Lys
            180                 185                 190

Ala Asp Glu Lys Arg His Ala Val Ile Leu Gly Asp Val Leu Tyr Gly
        195                 200                 205

Ser Glu Glu Lys Gly Thr Tyr His Leu Gly Ile Phe Gly Gly Lys Ala
    210                 215                 220

Gln Glu Val Ala Gly Ser Ala Thr Val Lys Ile Gly Glu Lys Val His
225                 230                 235                 240

His Ile Gly Leu Ala Ala Lys Gln
                245

<210> SEQ ID NO 32
<211> LENGTH: 248
<212> TYPE: PRT
<213> ORGANISM: Neisseria meningitidis
```

<400> SEQUENCE: 32

```
Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Thr Pro Glu Leu Asn Val Asp Leu Ala Ala Asp Ile Lys
            180                 185                 190

Ala Asp Glu Lys Arg His Ala Val Ile Leu Gly Asp Val Leu Tyr Gly
        195                 200                 205

Gly Glu Glu Lys Gly Thr Tyr His Leu Gly Ile Phe Gly Gly Lys Ala
    210                 215                 220

Gln Glu Val Ala Gly Ser Ala Thr Val Lys Ile Gly Glu Lys Val His
225                 230                 235                 240

His Ile Gly Leu Ala Ala Lys Gln
                245
```

<210> SEQ ID NO 33
<211> LENGTH: 248
<212> TYPE: PRT
<213> ORGANISM: Neisseria meningitidis

<400> SEQUENCE: 33

```
Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110
```

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
        130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Thr Pro Glu Leu Asn Val Asp Leu Ala Ala Ala Asp Ile Lys
            180                 185                 190

Ala Asp Glu Lys Arg His Ala Val Ile Leu Gly Asp Val Arg Tyr Gly
                195                 200                 205

Gly Glu Glu Lys Gly Thr Tyr His Leu Gly Ile Phe Gly Gly Lys Ala
        210                 215                 220

Gln Glu Val Ala Gly Ser Ala Thr Val Lys Ile Arg Glu Lys Val His
225                 230                 235                 240

His Ile Gly Leu Ala Ala Lys Gln
                245

<210> SEQ ID NO 34
<211> LENGTH: 248
<212> TYPE: PRT
<213> ORGANISM: Neisseria meningitidis

<400> SEQUENCE: 34

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
        130                 135                 140

Tyr Arg Gly Thr Ala Phe Gly Phe Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Thr Pro Glu Leu Asn Val Asp Leu Ala Ala Ala Asp Ile Lys
            180                 185                 190

Ala Asp Glu Lys Arg His Ala Val Ile Leu Gly Asp Val Arg Tyr Gly
                195                 200                 205

Gly Glu Glu Lys Gly Thr Tyr His Leu Gly Ile Phe Gly Gly Lys Ala
        210                 215                 220

Gln Glu Val Ala Gly Ser Ala Thr Val Lys Ile Arg Glu Lys Val His

His Ile Gly Leu Ala Ala Lys Gln
            245

<210> SEQ ID NO 35
<211> LENGTH: 248
<212> TYPE: PRT
<213> ORGANISM: Neisseria meningitidis

<400> SEQUENCE: 35

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Thr Pro Glu Leu Asn Val Asp Leu Ala Ala Ala Asp Ile Lys
            180                 185                 190

Ala Asp Glu Lys Arg His Ala Val Ile Leu Gly Asp Val Arg Tyr Gly
        195                 200                 205

Ser Glu Glu Lys Gly Thr Tyr His Leu Gly Ile Phe Gly Gly Lys Ala
    210                 215                 220

Gln Glu Val Ala Gly Ser Ala Thr Val Lys Ile Arg Glu Lys Val His
225                 230                 235                 240

His Ile Gly Leu Ala Ala Lys Gln
            245

<210> SEQ ID NO 36
<211> LENGTH: 248
<212> TYPE: PRT
<213> ORGANISM: Neisseria meningitidis

<400> SEQUENCE: 36

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp

```
Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95

Ser Ala Leu Thr Ala Phe Gln Thr Glu Gln Ile Asn Asn Pro Asp Lys
            100                 105                 110

Ser Gly Lys Met Val Ala Lys Arg Gln Phe Arg Ile Gly Asp Ile Ala
            115                 120                 125

Gly Glu His Thr Ser Phe Asp Lys Leu Pro Glu Gly Gly Arg Ala Thr
        130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Thr Pro Glu Leu Asn Val Asp Leu Ala Ala Ala Asp Ile Lys
            180                 185                 190

Ala Asp Glu Lys Arg His Ala Val Ile Leu Gly Asp Val Arg Tyr Gly
        195                 200                 205

Ser Glu Glu Lys Gly Thr Tyr His Leu Gly Ile Phe Gly Gly Lys Ala
    210                 215                 220

Gln Glu Val Ala Gly Ser Ala Thr Val Lys Ile Gly Glu Lys Val His
225                 230                 235                 240

His Ile Gly Leu Ala Ala Lys Gln
                245
```

<210> SEQ ID NO 37
<211> LENGTH: 248
<212> TYPE: PRT
<213> ORGANISM: Neisseria meningitidis

<400> SEQUENCE: 37

```
Val Ala Ala Asp Ile Gly Ala Gly Leu Ala Asp Ala Leu Thr Ala Pro
  1               5                  10                  15

Leu Asp His Lys Asp Lys Gly Leu Gln Ser Leu Thr Leu Asp Gln Ser
                 20                  25                  30

Val Arg Lys Asn Glu Lys Leu Lys Leu Ala Ala Gln Gly Ala Glu Lys
             35                  40                  45

Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95

Ser Ala Leu Thr Ala Phe Gln Thr Glu Gln Ile Asn Asn Pro Asp Lys
            100                 105                 110

Ser Gly Lys Met Val Ala Lys Arg Gln Phe Arg Ile Gly Asp Ile Ala
            115                 120                 125

Gly Glu His Thr Ser Phe Asp Lys Leu Pro Glu Gly Gly Arg Ala Thr
        130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175
```

```
Leu Lys Thr Pro Glu Leu Asn Val Asp Leu Ala Ala Asp Ile Lys
            180                 185                 190

Ala Asp Glu Lys Arg His Ala Val Ile Leu Gly Asp Val Arg Tyr Gly
        195                 200                 205

Gly Glu Glu Lys Gly Thr Tyr His Leu Gly Ile Phe Gly Gly Lys Ala
    210                 215                 220

Gln Glu Val Ala Gly Ser Ala Thr Val Lys Ile Gly Glu Lys Val His
225                 230                 235                 240

His Ile Gly Leu Ala Ala Lys Gln
            245
```

<210> SEQ ID NO 38
<211> LENGTH: 248
<212> TYPE: PRT
<213> ORGANISM: Neisseria meningitidis

<400> SEQUENCE: 38

```
Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
            85                  90                  95

Ser Ala Leu Thr Ala Phe Gln Thr Glu Gln Ile Asn Asn Pro Asp Lys
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
            165                 170                 175

Leu Lys Thr Pro Glu Leu Asn Val Asp Leu Ala Ala Ala Asp Ile Lys
            180                 185                 190

Ala Asp Glu Lys Arg His Ala Val Ile Leu Gly Asp Val Arg Tyr Gly
        195                 200                 205

Gly Glu Glu Lys Gly Thr Tyr His Leu Gly Ile Phe Gly Gly Lys Ala
    210                 215                 220

Gln Glu Val Ala Gly Ser Ala Thr Val Lys Ile Arg Glu Lys Val His
225                 230                 235                 240

His Ile Gly Leu Ala Ala Lys Gln
            245
```

<210> SEQ ID NO 39
<211> LENGTH: 248
<212> TYPE: PRT
<213> ORGANISM: Neisseria meningitidis

<400> SEQUENCE: 39

Val Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Asn Asn Pro Asp Lys
                100                 105                 110

Ser Gly Lys Met Val Ala Lys Arg Gln Phe Arg Ile Gly Asp Ile Ala
                115                 120                 125

Gly Glu His Thr Ser Phe Asp Lys Leu Pro Glu Gly Gly Arg Ala Thr
            130                 135                 140

Tyr Arg Gly Thr Ala Phe Gly Phe Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Thr Pro Glu Leu Asn Val Asp Leu Ala Ala Ala Asp Ile Lys
                180                 185                 190

Ala Asp Glu Lys Arg His Ala Val Ile Leu Gly Asp Val Arg Tyr Gly
            195                 200                 205

Gly Glu Glu Lys Gly Thr Tyr His Leu Gly Ile Phe Gly Gly Lys Ala
            210                 215                 220

Gln Glu Val Ala Gly Ser Ala Thr Val Lys Ile Arg Glu Lys Val His
225                 230                 235                 240

His Ile Gly Leu Ala Ala Lys Gln
                245

<210> SEQ ID NO 40
<211> LENGTH: 248
<212> TYPE: PRT
<213> ORGANISM: Neisseria meningitidis

<400> SEQUENCE: 40

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Asn Asn Pro Asp Lys
                100                 105                 110

Ser Gly Lys Met Val Ala Lys Arg Gln Phe Arg Ile Gly Asp Ile Ala
                115                 120                 125

```
Gly Glu His Thr Ser Phe Asp Lys Leu Pro Glu Gly Arg Ala Thr
            130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Thr Pro Glu Leu Asn Val Asp Leu Ala Ala Ala Asp Ile Lys
            180                 185                 190

Ala Asp Glu Lys Arg His Ala Val Ile Leu Gly Asp Val Arg Tyr Gly
        195                 200                 205

Ser Glu Glu Lys Gly Thr Tyr His Leu Gly Ile Phe Gly Gly Lys Ala
    210                 215                 220

Gln Glu Val Ala Gly Ser Ala Thr Val Lys Ile Arg Glu Lys Val His
225                 230                 235                 240

His Ile Gly Leu Ala Ala Lys Gln
                245
```

<210> SEQ ID NO 41
<211> LENGTH: 247
<212> TYPE: PRT
<213> ORGANISM: Neisseria meningitidis

<400> SEQUENCE: 41

```
Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Leu Gly
        115                 120                 125

Gly Glu His Thr Ala Phe Asn Gln Leu Pro Asp Gly Lys Ala Glu Tyr
    130                 135                 140

His Gly Thr Ala Phe Gly Ser Asp Asp Ala Gly Gly Lys Leu Thr Tyr
145                 150                 155                 160

Ser Ile Asp Phe Thr Lys Lys Gln Gly Asn Gly Lys Ile Glu His Leu
                165                 170                 175

Lys Ser Pro Glu Leu Asn Val Asp Leu Ala Ala Ala Glu Ile Lys Ala
            180                 185                 190

Asp Glu Lys Arg His Ala Val Ile Ser Gly Ser Val Leu Tyr Asn Gln
        195                 200                 205

Ala Glu Lys Gly Ser Tyr Ser Leu Gly Ile Phe Gly Gly Arg Ala Gln
    210                 215                 220

Glu Val Ala Gly Ser Ala Glu Val Lys Thr Val Asn Gly Ile Arg His
225                 230                 235                 240

Ile Gly Leu Ala Ala Lys Gln
```

<210> SEQ ID NO 42
<211> LENGTH: 247
<212> TYPE: PRT
<213> ORGANISM: Neisseria meningitidis

<400> SEQUENCE: 42

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Asn Asn Pro Asp Lys
            100                 105                 110

Ile Asp Ser Met Val Ala Lys Arg Gln Phe Arg Ile Gly Asp Leu Gly
        115                 120                 125

Gly Glu His Thr Ala Phe Asn Gln Leu Pro Asp Gly Lys Ala Glu Tyr
    130                 135                 140

His Gly Thr Ala Phe Gly Ser Asp Asp Ala Gly Gly Lys Leu Thr Tyr
145                 150                 155                 160

Ser Ile Asp Phe Thr Lys Lys Gln Gly Asn Gly Lys Ile Glu His Leu
                165                 170                 175

Lys Ser Pro Glu Leu Asn Val Asp Leu Ala Ala Ala Glu Ile Lys Ala
            180                 185                 190

Asp Glu Lys Arg His Ala Val Ile Ser Gly Ser Val Leu Tyr Asn Gln
        195                 200                 205

Ala Glu Lys Gly Ser Tyr Ser Leu Gly Ile Phe Gly Gly Arg Ala Gln
    210                 215                 220

Glu Val Ala Gly Ser Ala Glu Val Lys Thr Val Asn Gly Ile Arg His
225                 230                 235                 240

Ile Gly Leu Ala Ala Lys Gln
                245

<210> SEQ ID NO 43
<211> LENGTH: 247
<212> TYPE: PRT
<213> ORGANISM: Neisseria meningitidis

<400> SEQUENCE: 43

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln

```
                65                  70                  75                  80
Leu Ile Thr Leu Glu Ser Gly Glu Phe Gln Val Tyr Lys Gln Ser His
                    85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Leu Gly
                115                 120                 125

Gly Glu His Thr Ala Phe Asn Gln Leu Pro Gly Gly Lys Ala Glu Tyr
            130                 135                 140

His Gly Thr Ala Phe Gly Ser Asp Asp Ala Gly Gly Lys Leu Thr Tyr
145                 150                 155                 160

Ser Ile Asp Phe Thr Lys Lys Gln Gly Asn Gly Lys Ile Glu His Leu
                165                 170                 175

Lys Ser Pro Glu Leu Asn Val Asp Leu Ala Ala Ala Glu Ile Lys Ala
                180                 185                 190

Asp Glu Lys Arg His Ala Val Ile Ser Gly Ser Val Leu Tyr Asn Gln
                195                 200                 205

Ala Glu Lys Gly Ser Tyr Ser Leu Gly Ile Phe Gly Gly Arg Ala Gln
            210                 215                 220

Glu Val Ala Gly Ser Ala Glu Val Lys Thr Val Asn Gly Ile Arg His
225                 230                 235                 240

Ile Gly Leu Ala Ala Lys Gln
                245

<210> SEQ ID NO 44
<211> LENGTH: 247
<212> TYPE: PRT
<213> ORGANISM: Neisseria meningitidis

<400> SEQUENCE: 44

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                    85                  90                  95

Ser Ala Leu Thr Ala Phe Gln Thr Glu Gln Ile Asn Asn Pro Asp Lys
                100                 105                 110

Ile Asp Ser Met Val Ala Lys Arg Gln Phe Arg Ile Gly Asp Leu Gly
                115                 120                 125

Gly Glu His Thr Ala Phe Asn Gln Leu Pro Gly Gly Lys Ala Glu Tyr
            130                 135                 140

His Gly Thr Ala Phe Gly Ser Asp Asp Ala Gly Gly Lys Leu Thr Tyr
145                 150                 155                 160

Ser Ile Asp Phe Thr Lys Lys Gln Gly Asn Gly Lys Ile Glu His Leu
                165                 170                 175

Lys Ser Pro Glu Leu Asn Val Asp Leu Ala Ala Ala Glu Ile Lys Ala
                180                 185                 190
```

```
Asp Glu Lys Arg His Ala Val Ile Ser Gly Ser Val Leu Tyr Asn Gln
            195                 200                 205
Ala Glu Lys Gly Ser Tyr Ser Leu Gly Ile Phe Gly Gly Arg Ala Gln
        210                 215                 220
Glu Val Ala Gly Ser Ala Glu Val Lys Thr Val Asn Gly Ile Arg His
225                 230                 235                 240
Ile Gly Leu Ala Ala Lys Gln
                245
```

<210> SEQ ID NO 45
<211> LENGTH: 247
<212> TYPE: PRT
<213> ORGANISM: Neisseria meningitidis

<400> SEQUENCE: 45

```
Val Ala Ala Asp Ile Gly Ala Gly Leu Ala Asp Ala Leu Thr Ala Pro
1               5                   10                  15
Leu Asp His Lys Asp Lys Gly Leu Gln Ser Leu Thr Leu Asp Gln Ser
            20                  25                  30
Val Arg Lys Asn Glu Lys Leu Lys Leu Ala Ala Gln Gly Ala Glu Lys
        35                  40                  45
Thr Tyr Gly Asn Gly Asp Ser Leu Asn Thr Gly Lys Leu Lys Asn Asp
    50                  55                  60
Lys Val Ser Arg Phe Asp Phe Ile Arg Gln Ile Glu Val Asp Gly Gln
65                  70                  75                  80
Leu Ile Thr Leu Glu Ser Gly Glu Phe Gln Val Tyr Lys Gln Ser His
                85                  90                  95
Ser Ala Leu Thr Ala Phe Gln Thr Glu Gln Ile Gln Asp Ser Glu His
            100                 105                 110
Ser Gly Lys Met Val Ala Lys Arg Gln Phe Arg Ile Gly Asp Leu Gly
        115                 120                 125
Gly Glu His Thr Ala Phe Asn Gln Leu Pro Gly Gly Lys Ala Glu Tyr
    130                 135                 140
His Gly Thr Ala Phe Gly Ser Asp Asp Ala Gly Gly Lys Leu Thr Tyr
145                 150                 155                 160
Thr Ile Asp Phe Ala Ala Lys Gln Gly Asn Gly Lys Ile Glu His Leu
                165                 170                 175
Lys Ser Pro Glu Leu Asn Val Asp Leu Ala Ala Ala Glu Ile Lys Ala
            180                 185                 190
Asp Glu Lys Arg His Ala Val Ile Ser Gly Ser Val Leu Tyr Asn Gln
        195                 200                 205
Ala Glu Lys Gly Ser Tyr Ser Leu Gly Ile Phe Gly Gly Arg Ala Gln
    210                 215                 220
Glu Val Ala Gly Ser Ala Glu Val Lys Thr Val Asn Gly Ile Arg His
225                 230                 235                 240
Ile Gly Leu Ala Ala Lys Gln
                245
```

<210> SEQ ID NO 46
<211> LENGTH: 247
<212> TYPE: PRT
<213> ORGANISM: Neisseria meningitidis

<400> SEQUENCE: 46

```
Val Ala Ala Asp Ile Gly Ala Gly Leu Ala Asp Ala Leu Thr Ala Pro
1               5                   10                  15
```

```
Leu Asp His Lys Asp Lys Gly Leu Gln Ser Leu Thr Leu Asp Gln Ser
             20                  25                  30

Val Arg Lys Asn Glu Lys Leu Lys Leu Ala Ala Gln Gly Ala Glu Lys
         35                  40                  45

Thr Tyr Gly Asn Gly Asp Ser Leu Asn Thr Gly Lys Leu Lys Asn Asp
     50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95

Ser Ala Leu Thr Ala Phe Gln Thr Glu Gln Ile Asn Asn Pro Asp Lys
            100                 105                 110

Ile Asp Ser Met Val Ala Lys Arg Gln Phe Arg Ile Gly Asp Leu Gly
        115                 120                 125

Gly Glu His Thr Ala Phe Asn Gln Leu Pro Gly Gly Lys Ala Glu Tyr
    130                 135                 140

His Gly Thr Ala Phe Gly Ser Asp Asp Ala Gly Gly Lys Leu Thr Tyr
145                 150                 155                 160

Thr Ile Asp Phe Ala Ala Lys Gln Gly Asn Gly Lys Ile Glu His Leu
                165                 170                 175

Lys Ser Pro Glu Leu Asn Val Asp Leu Ala Ala Ala Glu Ile Lys Ala
            180                 185                 190

Asp Glu Lys Arg His Ala Val Ile Ser Gly Ser Val Leu Tyr Asn Gln
        195                 200                 205

Ala Glu Lys Gly Ser Tyr Ser Leu Gly Ile Phe Gly Gly Arg Ala Gln
    210                 215                 220

Glu Val Ala Gly Ser Ala Glu Val Lys Thr Val Asn Gly Ile Arg His
225                 230                 235                 240

Ile Gly Leu Ala Ala Lys Gln
                245

<210> SEQ ID NO 47
<211> LENGTH: 247
<212> TYPE: PRT
<213> ORGANISM: Neisseria meningitidis

<400> SEQUENCE: 47

Val Ala Ala Asp Ile Gly Ala Gly Leu Ala Asp Ala Leu Thr Ala Pro
 1               5                  10                  15

Leu Asp His Lys Asp Lys Gly Leu Gln Ser Leu Thr Leu Asp Gln Ser
             20                  25                  30

Val Arg Lys Asn Glu Lys Leu Lys Leu Ala Ala Gln Gly Ala Glu Lys
         35                  40                  45

Thr Tyr Gly Asn Gly Asp Ser Leu Asn Thr Gly Lys Leu Lys Asn Asp
     50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Leu Gly
        115                 120                 125

Gly Glu His Thr Ala Phe Asn Gln Leu Pro Ser Gly Lys Ala Glu Tyr
    130                 135                 140
```

His Gly Thr Ala Phe Gly Ser Asp Asp Ala Gly Gly Lys Leu Thr Tyr
145                 150                 155                 160

Ser Ile Asp Phe Thr Lys Lys Gln Gly Asn Gly Lys Ile Glu His Leu
                165                 170                 175

Lys Ser Pro Glu Leu Asn Val Asp Leu Ala Ala Ala Glu Ile Lys Ala
            180                 185                 190

Asp Glu Lys Arg His Ala Val Ile Ser Gly Ser Val Leu Tyr Asn Gln
        195                 200                 205

Ala Glu Lys Gly Ser Tyr Ser Leu Gly Ile Phe Gly Gly Arg Ala Gln
    210                 215                 220

Glu Val Ala Gly Ser Ala Glu Val Lys Thr Val Asn Gly Ile Arg His
225                 230                 235                 240

Ile Gly Leu Ala Ala Lys Gln
                245

<210> SEQ ID NO 48
<211> LENGTH: 247
<212> TYPE: PRT
<213> ORGANISM: Neisseria meningitidis

<400> SEQUENCE: 48

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Asn Asn Pro Asp Lys
                100                 105                 110

Ile Asp Ser Met Val Ala Lys Arg Gln Phe Arg Ile Gly Asp Leu Gly
            115                 120                 125

Gly Glu His Thr Ala Phe Asn Gln Leu Pro Ser Gly Lys Ala Glu Tyr
        130                 135                 140

His Gly Thr Ala Phe Gly Ser Asp Asp Ala Gly Gly Lys Leu Thr Tyr
145                 150                 155                 160

Ser Ile Asp Phe Thr Lys Lys Gln Gly Asn Gly Lys Ile Glu His Leu
                165                 170                 175

Lys Ser Pro Glu Leu Asn Val Asp Leu Ala Ala Ala Glu Ile Lys Ala
            180                 185                 190

Asp Glu Lys Arg His Ala Val Ile Ser Gly Ser Val Leu Tyr Asn Gln
        195                 200                 205

Ala Glu Lys Gly Ser Tyr Ser Leu Gly Ile Phe Gly Gly Arg Ala Gln
    210                 215                 220

Glu Val Ala Gly Ser Ala Glu Val Lys Thr Val Asn Gly Ile Arg His
225                 230                 235                 240

Ile Gly Leu Ala Ala Lys Gln
                245

```
<210> SEQ ID NO 49
<211> LENGTH: 247
<212> TYPE: PRT
<213> ORGANISM: Neisseria meningitidis

<400> SEQUENCE: 49

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Leu Gly
        115                 120                 125

Gly Glu His Thr Ala Phe Asn Gln Leu Pro Ser Gly Lys Ala Glu Tyr
    130                 135                 140

His Gly Thr Ala Phe Gly Ser Asp Asp Ala Gly Gly Lys Leu Thr Tyr
145                 150                 155                 160

Thr Ile Asp Phe Ala Ala Lys Gln Gly Asn Gly Lys Ile Glu His Leu
                165                 170                 175

Lys Ser Pro Glu Leu Asn Val Asp Leu Ala Ala Ala Glu Ile Lys Ala
            180                 185                 190

Asp Glu Lys Arg His Ala Val Ile Ser Gly Ser Val Leu Tyr Asn Gln
        195                 200                 205

Ala Glu Lys Gly Ser Tyr Ser Leu Gly Ile Phe Gly Gly Arg Ala Gln
    210                 215                 220

Glu Val Ala Gly Ser Ala Glu Val Lys Thr Val Asn Gly Ile Arg His
225                 230                 235                 240

Ile Gly Leu Ala Ala Lys Gln
                245

<210> SEQ ID NO 50
<211> LENGTH: 247
<212> TYPE: PRT
<213> ORGANISM: Neisseria meningitidis

<400> SEQUENCE: 50

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
```

```
            85                  90                  95
Ser Ala Leu Thr Ala Phe Gln Thr Glu Gln Ile Asn Asn Pro Asp Lys
            100                 105                 110

Ile Asp Ser Met Val Ala Lys Arg Gln Phe Arg Ile Gly Asp Leu Gly
            115                 120                 125

Gly Glu His Thr Ala Phe Asn Gln Leu Pro Ser Gly Lys Ala Glu Tyr
            130                 135                 140

His Gly Thr Ala Phe Gly Ser Asp Ala Gly Gly Lys Leu Thr Tyr
145                 150                 155                 160

Thr Ile Asp Phe Ala Ala Lys Gln Gly Asn Gly Lys Ile Glu His Leu
                165                 170                 175

Lys Ser Pro Glu Leu Asn Val Asp Leu Ala Ala Ala Glu Ile Lys Ala
            180                 185                 190

Asp Glu Lys Arg His Ala Val Ile Ser Gly Ser Val Leu Tyr Asn Gln
            195                 200                 205

Ala Glu Lys Gly Ser Tyr Ser Leu Gly Ile Phe Gly Gly Arg Ala Gln
            210                 215                 220

Glu Val Ala Gly Ser Ala Glu Val Lys Thr Val Asn Gly Ile Arg His
225                 230                 235                 240

Ile Gly Leu Ala Ala Lys Gln
            245

<210> SEQ ID NO 51
<211> LENGTH: 247
<212> TYPE: PRT
<213> ORGANISM: Neisseria meningitidis

<400> SEQUENCE: 51

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
            50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Asn Asn Pro Asp Lys
            100                 105                 110

Ile Asp Ser Met Val Ala Lys Arg Gln Phe Arg Ile Gly Asp Leu Gly
            115                 120                 125

Gly Glu His Thr Ala Phe Asn Gln Leu Pro Gly Gly Lys Ala Glu Tyr
            130                 135                 140

His Gly Thr Ala Phe Gly Ser Asp Ala Gly Gly Lys Leu Thr Tyr
145                 150                 155                 160

Ser Ile Asp Phe Thr Asn Lys Gln Gly Asn Gly Lys Ile Glu His Leu
                165                 170                 175

Lys Ser Pro Glu Leu Asn Val Asp Leu Ala Ala Ala Glu Ile Lys Ala
            180                 185                 190

Asp Glu Lys Arg His Ala Val Ile Ser Gly Ser Val Leu Tyr Asn Gln
            195                 200                 205
```

```
Ala Glu Lys Gly Ser Tyr Ser Leu Gly Ile Phe Gly Arg Ala Gln
    210                 215                 220

Glu Val Ala Gly Ser Ala Glu Val Lys Thr Val Asn Gly Ile Arg His
225                 230                 235                 240

Ile Gly Leu Ala Ala Lys Gln
                245

<210> SEQ ID NO 52
<211> LENGTH: 247
<212> TYPE: PRT
<213> ORGANISM: Neisseria meningitidis

<400> SEQUENCE: 52

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Leu Gly
        115                 120                 125

Gly Glu His Thr Ala Phe Asn Gln Leu Pro Gly Gly Lys Ala Glu Tyr
    130                 135                 140

His Gly Thr Ala Phe Gly Ser Asp Asp Ala Gly Gly Lys Leu Thr Tyr
145                 150                 155                 160

Ser Ile Asp Phe Thr Asn Lys Gln Gly Asn Gly Lys Ile Glu His Leu
                165                 170                 175

Lys Ser Pro Glu Leu Asn Val Asp Leu Ala Ala Ala Glu Ile Lys Ala
            180                 185                 190

Asp Glu Lys Arg His Ala Val Ile Ser Gly Ser Val Leu Tyr Asn Gln
        195                 200                 205

Ala Glu Lys Gly Ser Tyr Ser Leu Gly Ile Phe Gly Arg Ala Gln
    210                 215                 220

Glu Val Ala Gly Ser Ala Glu Val Lys Thr Val Asn Gly Ile Arg His
225                 230                 235                 240

Ile Gly Leu Ala Ala Lys Gln
                245

<210> SEQ ID NO 53
<211> LENGTH: 248
<212> TYPE: PRT
<213> ORGANISM: Neisseria meningitidis

<400> SEQUENCE: 53

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30
```

```
Val Arg Lys Asn Glu Lys Leu Lys Leu Ala Ala Gln Gly Ala Glu Lys
         35                  40                  45

Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Ile Ala
                115                 120                 125

Gly Glu His Thr Ser Phe Asp Lys Leu Pro Glu Gly Arg Ala Thr
        130                 135                 140

Tyr Arg Gly Thr Ala Phe Gly Ser Asp Asp Ala Gly Gly Lys Leu His
145                 150                 155                 160

Tyr Ser Ile Asp Phe Thr Lys Lys Gln Gly Tyr Gly Arg Ile Glu His
                165                 170                 175

Leu Lys Thr Pro Glu Leu Asn Val Glu Leu Ala Ser Ala Asp Ile Lys
                180                 185                 190

Pro Asp Gly Lys Arg His Ala Val Ile Ser Gly Ser Val Arg Tyr Asn
                195                 200                 205

Gly Ser Glu Lys Gly Ser Tyr Ser Leu Gly Ile Phe Gly Gly Lys Ala
        210                 215                 220

Gln Glu Val Ala Gly Ser Ala Glu Val Lys Thr Gly Glu Gly Ile Arg
225                 230                 235                 240

His Ile Gly Leu Ala Ala Lys Gln
                245

<210> SEQ ID NO 54
<211> LENGTH: 248
<212> TYPE: PRT
<213> ORGANISM: Neisseria meningitidis

<400> SEQUENCE: 54

Val Ala Ala Asp Ile Gly Ala Gly Leu Ala Asp Ala Leu Thr Ala Pro
 1               5                  10                  15

Leu Asp His Lys Asp Lys Gly Leu Gln Ser Leu Thr Leu Asp Gln Ser
                 20                  25                  30

Val Arg Lys Asn Glu Lys Leu Lys Leu Ala Ala Gln Gly Ala Glu Lys
         35                  40                  45

Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Ile Ala
                115                 120                 125

Gly Glu His Thr Ser Phe Asp Lys Leu Pro Glu Gly Arg Ala Thr
        130                 135                 140

Tyr Arg Gly Thr Ala Phe Gly Ser Asp Asp Ala Gly Gly Lys Leu His
145                 150                 155                 160
```

Tyr Ser Ile Asp Phe Ala Ala Lys Gln Gly His Gly Arg Ile Glu His
            165                 170                 175

Leu Lys Thr Pro Glu Leu Asn Val Glu Leu Ala Ser Ala Asp Ile Lys
        180                 185                 190

Pro Asp Gly Lys Arg His Ala Val Ile Ser Gly Ser Val Arg Tyr Asn
    195                 200                 205

Gly Ser Glu Lys Gly Ser Tyr Ser Leu Gly Ile Phe Gly Gly Lys Ala
210                 215                 220

Gln Glu Val Ala Gly Ser Ala Glu Val Lys Thr Gly Glu Gly Ile Arg
225                 230                 235                 240

His Ile Gly Leu Ala Ala Lys Gln
            245

<210> SEQ ID NO 55
<211> LENGTH: 248
<212> TYPE: PRT
<213> ORGANISM: Neisseria meningitidis

<400> SEQUENCE: 55

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
            85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu His
145                 150                 155                 160

Tyr Ser Ile Asp Phe Ala Ala Lys Gln Gly His Gly Arg Ile Glu His
            165                 170                 175

Leu Lys Thr Pro Glu Leu Asn Val Glu Leu Ala Ser Ala Asp Ile Lys
        180                 185                 190

Pro Asp Gly Lys Arg His Ala Val Ile Ser Gly Ser Val Arg Tyr Asn
    195                 200                 205

Gly Gly Glu Lys Gly Ser Tyr Ser Leu Gly Ile Phe Gly Gly Lys Ala
210                 215                 220

Gln Glu Val Ala Gly Ser Ala Glu Val Lys Thr Arg Glu Gly Ile Arg
225                 230                 235                 240

His Ile Gly Leu Ala Ala Lys Gln
            245

<210> SEQ ID NO 56
<211> LENGTH: 248
<212> TYPE: PRT

<213> ORGANISM: Neisseria meningitidis

<400> SEQUENCE: 56

Val Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Leu Gly
            115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Glu Leu Lys
            180                 185                 190

Ala Asp Glu Lys Arg His Ala Val Ile Leu Gly Asp Val Leu Tyr Asn
        195                 200                 205

Gln Glu Glu Lys Gly Thr Tyr Ser Leu Gly Ile Phe Gly Gly Lys Ala
    210                 215                 220

Gln Glu Val Ala Gly Ser Ala Thr Val Lys Thr Val Asn Gly Ile His
225                 230                 235                 240

Glu Ile Gly Leu Ala Ala Lys Gln
                245

<210> SEQ ID NO 57
<211> LENGTH: 250
<212> TYPE: PRT
<213> ORGANISM: Neisseria meningitidis

<400> SEQUENCE: 57

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Asn Asn Pro Asp Lys

```
              100                 105                 110
Ile Asp Ser Met Val Ala Lys Arg Gln Phe Arg Ile Gly Asp Leu Gly
            115                 120                 125

Gly Glu His Thr Ser Phe Asp Lys Leu Pro Glu Gly Gly Arg Ala Thr
        130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Glu Leu Lys
            180                 185                 190

Ala Asp Glu Lys Arg His Ala Val Ile Leu Gly Asp Val Leu Tyr Asn
        195                 200                 205

Gln Glu Glu Lys Gly Thr Tyr Ser Leu Gly Ile Phe Gly Gly Lys Ala
    210                 215                 220

Gln Glu Val Ala Gly Ser Ala Thr Val Lys Thr Val Asn Gly Ile His
225                 230                 235                 240

Glu Ile Gly Leu Ala Ala Lys Gln Leu Glu
            245                 250

<210> SEQ ID NO 58
<211> LENGTH: 248
<212> TYPE: PRT
<213> ORGANISM: Neisseria meningitidis

<400> SEQUENCE: 58

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Leu Gly
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Glu Leu Lys
            180                 185                 190

Ala Asp Glu Lys Ser His Ala Val Ile Leu Gly Asp Val Leu Tyr Asn
        195                 200                 205

Gln Glu Glu Lys Gly Thr Tyr Ser Leu Gly Ile Phe Gly Gly Lys Ala
    210                 215                 220
```

Gln Glu Val Ala Gly Ser Ala Thr Val Lys Thr Val Asn Gly Ile His
225                 230                 235                 240

Glu Ile Gly Leu Ala Ala Lys Gln
                245

<210> SEQ ID NO 59
<211> LENGTH: 248
<212> TYPE: PRT
<213> ORGANISM: Neisseria meningitidis

<400> SEQUENCE: 59

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Asn Asn Pro Asp Lys
            100                 105                 110

Ile Asp Ser Met Val Ala Lys Arg Gln Phe Arg Ile Gly Asp Leu Gly
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Glu Leu Lys
            180                 185                 190

Ala Asp Glu Lys Ser His Ala Val Ile Leu Gly Asp Val Leu Tyr Asn
        195                 200                 205

Gln Glu Glu Lys Gly Thr Tyr Ser Leu Gly Ile Phe Gly Gly Lys Ala
    210                 215                 220

Gln Glu Val Ala Gly Ser Ala Thr Val Lys Thr Val Asn Gly Ile His
225                 230                 235                 240

Glu Ile Gly Leu Ala Ala Lys Gln
                245

<210> SEQ ID NO 60
<211> LENGTH: 248
<212> TYPE: PRT
<213> ORGANISM: Neisseria meningitidis

<400> SEQUENCE: 60

Val Ala Ala Asp Ile Gly Ala Gly Leu Ala Asp Ala Leu Thr Thr Pro
1               5                   10                  15

Leu Asp His Lys Asp Lys Ser Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

```
Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Gln
 65                  70                  75                  80

Thr Ile Thr Leu Ala Ser Gly Glu Phe Gln Ile Tyr Lys Gln Asn His
                 85                  90                  95

Ser Ala Val Val Ala Leu Gln Ile Glu Lys Ile Asn Asn Pro Asp Lys
                100                 105                 110

Ile Asp Ser Leu Ile Asn Gln Arg Ser Phe Leu Val Ser Gly Leu Ala
                115                 120                 125

Gly Glu His Thr Ser Phe Asp Lys Leu Pro Glu Gly Gly Arg Ala Thr
            130                 135                 140

Tyr Arg Gly Thr Ala Phe Ser Ser Asp Asp Pro Asn Gly Arg Leu Thr
145                 150                 155                 160

Tyr Ser Ile Asp Phe Thr Ala Lys Gln Gly Asn Gly Arg Ile Glu His
                165                 170                 175

Leu Lys Thr Pro Glu Gln Asn Val Asp Leu Ala Ser Ala Glu Leu Lys
                180                 185                 190

Pro Asp Gly Lys Arg His Ala Val Ile Ser Gly Ser Val Arg Tyr Gly
            195                 200                 205

Gly Glu Glu Lys Gly Thr Tyr Ser Leu Gly Leu Phe Gly Gly Lys Ala
        210                 215                 220

Gln Glu Ile Ala Gly Ser Ala Thr Val Lys Ile Arg Glu Lys Val His
225                 230                 235                 240

Glu Ile Gly Ile Ala Gly Lys Gln
                245

<210> SEQ ID NO 61
<211> LENGTH: 248
<212> TYPE: PRT
<213> ORGANISM: Neisseria meningitidis

<400> SEQUENCE: 61

Val Ala Ala Asp Ile Gly Ala Gly Leu Ala Asp Ala Leu Thr Thr Pro
 1               5                  10                  15

Leu Asp His Lys Asp Lys Ser Leu Gln Ser Leu Thr Leu Asp Gln Ser
                 20                  25                  30

Val Arg Lys Asn Glu Lys Leu Lys Leu Ala Ala Gln Gly Ala Glu Lys
             35                  40                  45

Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Gln
 65                  70                  75                  80

Thr Ile Thr Leu Ala Ser Gly Glu Phe Gln Ile Tyr Lys Gln Asn His
                 85                  90                  95

Ser Ala Val Val Ala Leu Gln Ile Glu Lys Ile Asn Asn Pro Asp Lys
                100                 105                 110

Ile Asp Ser Leu Ile Asn Gln Arg Ser Phe Leu Val Ser Gly Leu Ala
                115                 120                 125

Gly Glu His Thr Ser Phe Asp Lys Leu Pro Glu Gly Gly Arg Ala Thr
            130                 135                 140

Tyr Arg Gly Thr Ala Phe Ser Ser Asp Asp Pro Asn Gly Arg Leu Thr
145                 150                 155                 160

Tyr Ser Ile Asp Phe Thr Ala Lys Gln Gly His Gly Arg Ile Glu His
                165                 170                 175
```

```
Leu Lys Thr Pro Glu Gln Asn Val Glu Leu Ala Ser Ala Tyr Leu Lys
            180                 185                 190

Pro Asp Glu Lys His His Ala Val Ile Ser Gly Ser Val Arg Tyr Gly
        195                 200                 205

Gly Glu Glu Lys Gly Thr Tyr Ser Leu Gly Leu Phe Gly Gly Lys Ala
    210                 215                 220

Gln Glu Ile Ala Gly Ser Ala Thr Val Lys Ile Arg Glu Lys Val His
225                 230                 235                 240

Glu Ile Gly Ile Ala Gly Lys Gln
                245

<210> SEQ ID NO 62
<211> LENGTH: 248
<212> TYPE: PRT
<213> ORGANISM: Neisseria meningitidis

<400> SEQUENCE: 62

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Glu Leu Ala Ala Ala Asp Ile Lys
            180                 185                 190

Ala Asp Gly Lys Arg His Ala Val Ile Leu Gly Asp Thr Arg Tyr Gly
        195                 200                 205

Ser Glu Glu Lys Gly Thr Tyr Ser Leu Gly Ile Phe Gly Gly Lys Ala
    210                 215                 220

Gln Glu Val Ala Gly Ser Ala Glu Val Lys Thr Gly Asn Gly Ile Arg
225                 230                 235                 240

His Ile Gly Leu Ala Ala Lys Gln
                245

<210> SEQ ID NO 63
<211> LENGTH: 248
<212> TYPE: PRT
<213> ORGANISM: Neisseria meningitidis

<400> SEQUENCE: 63
```

Val Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Glu Leu Ala Ala Ala Asp Ile Lys
            180                 185                 190

Ala Asp Gly Lys Arg His Ala Val Ile Leu Gly Asp Thr Arg Tyr Gly
        195                 200                 205

Gly Glu Glu Lys Gly Thr Tyr Ser Leu Gly Ile Phe Gly Gly Lys Ala
    210                 215                 220

Gln Glu Val Ala Gly Ser Ala Glu Val Lys Thr Arg Asn Gly Ile Arg
225                 230                 235                 240

His Ile Gly Leu Ala Ala Lys Gln
                245

<210> SEQ ID NO 64
<211> LENGTH: 248
<212> TYPE: PRT
<213> ORGANISM: Neisseria meningitidis

<400> SEQUENCE: 64

Val Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala

```
            115                 120                 125
Gly Glu His Thr Ser Phe Asp Lys Leu Pro Glu Gly Gly Arg Ala Thr
            130                 135                 140
Tyr Arg Gly Thr Ala Phe Gly Ser Asp Asp Ala Gly Gly Lys Leu His
145                 150                 155                 160
Tyr Thr Ile Asp Phe Ala Lys Lys Gln Gly Asn Gly Arg Ile Glu His
                165                 170                 175
Leu Lys Ser Pro Glu Leu Asn Val Glu Leu Ala Ala Ala Asp Ile Lys
                180                 185                 190
Ala Asp Gly Lys Arg His Ala Val Ile Leu Gly Asp Thr Arg Tyr Gly
                195                 200                 205
Gly Glu Glu Lys Gly Thr Tyr Ser Leu Gly Ile Phe Gly Gly Lys Ala
            210                 215                 220
Gln Glu Val Ala Gly Ser Ala Glu Val Lys Thr Arg Asn Gly Ile Arg
225                 230                 235                 240
His Ile Gly Leu Ala Ala Lys Gln
                245

<210> SEQ ID NO 65
<211> LENGTH: 248
<212> TYPE: PRT
<213> ORGANISM: Neisseria meningitidis

<400> SEQUENCE: 65

Val Ala Ala Asp Ile Gly Ala Gly Leu Ala Asp Ala Leu Thr Ala Pro
1               5                   10                  15
Leu Asp His Lys Asp Lys Gly Leu Gln Ser Leu Thr Leu Asp Gln Ser
                20                  25                  30
Val Arg Lys Asn Glu Lys Leu Lys Leu Ala Ala Gln Gly Ala Glu Lys
                35                  40                  45
Thr Tyr Gly Asn Gly Asp Ser Leu Asn Thr Gly Lys Leu Lys Asn Asp
            50                  55                  60
Lys Val Ser Arg Phe Asp Phe Ile Arg Gln Ile Glu Val Asp Gly Gln
65                  70                  75                  80
Leu Ile Thr Leu Glu Ser Gly Glu Phe Gln Val Tyr Lys Gln Ser His
                85                  90                  95
Ser Ala Leu Thr Ala Phe Gln Thr Glu Gln Ile Gln Asp Ser Glu His
                100                 105                 110
Ser Gly Lys Met Val Ala Lys Arg Gln Phe Arg Ile Gly Asp Ile Ala
            115                 120                 125
Gly Glu His Thr Ser Phe Asp Lys Leu Pro Glu Gly Gly Arg Ala Thr
            130                 135                 140
Tyr Arg Gly Thr Ala Phe Gly Ser Asp Asp Ala Gly Gly Lys Leu His
145                 150                 155                 160
Tyr Thr Ile Asp Phe Ala Lys Lys Gln Gly Asn Gly Arg Ile Glu His
                165                 170                 175
Leu Lys Ser Pro Glu Leu Asn Val Glu Leu Ala Ala Ala Asp Ile Lys
                180                 185                 190
Ala Asp Gly Lys Arg His Ala Val Ile Leu Gly Asp Thr Arg Tyr Gly
                195                 200                 205
Ser Glu Glu Lys Gly Thr Tyr Ser Leu Gly Ile Phe Gly Gly Lys Ala
            210                 215                 220
Gln Glu Val Ala Gly Ser Ala Glu Val Lys Thr Arg Asn Gly Ile Arg
225                 230                 235                 240
```

His Ile Gly Leu Ala Ala Lys Gln
            245

<210> SEQ ID NO 66
<211> LENGTH: 248
<212> TYPE: PRT
<213> ORGANISM: Neisseria meningitidis

<400> SEQUENCE: 66

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu His
145                 150                 155                 160

Tyr Thr Ile Asp Phe Ala Lys Lys Gln Gly Asn Gly Arg Ile Glu His
                165                 170                 175

Leu Lys Ser Pro Glu Leu Asn Val Glu Leu Ala Ala Ala Asp Ile Lys
            180                 185                 190

Ala Asp Gly Lys Arg His Ala Val Ile Leu Gly Asp Thr Arg Tyr Gly
        195                 200                 205

Gly Glu Glu Lys Gly Thr Tyr Ser Leu Gly Ile Phe Gly Gly Lys Ala
    210                 215                 220

Gln Glu Val Ala Gly Ser Ala Glu Val Lys Thr Gly Asn Gly Ile Arg
225                 230                 235                 240

His Ile Gly Leu Ala Ala Lys Gln
            245

<210> SEQ ID NO 67
<211> LENGTH: 248
<212> TYPE: PRT
<213> ORGANISM: Neisseria meningitidis

<400> SEQUENCE: 67

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

```
Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Ile Ala
                115                 120                 125

Gly Glu His Thr Ser Phe Asp Lys Leu Pro Glu Gly Gly Arg Ala Thr
            130                 135                 140

Tyr Arg Gly Thr Ala Phe Gly Ser Asp Asp Ala Gly Gly Lys Leu His
145                 150                 155                 160

Tyr Thr Ile Asp Phe Ala Lys Lys Gln Gly Asn Gly Arg Ile Glu His
                165                 170                 175

Leu Lys Ser Pro Glu Leu Asn Val Glu Leu Ala Ala Ala Asp Ile Lys
                180                 185                 190

Ala Asp Gly Lys Arg His Ala Val Ile Leu Gly Asp Thr Arg Tyr Gly
            195                 200                 205

Ser Glu Glu Lys Gly Thr Tyr Ser Leu Gly Ile Phe Gly Gly Lys Ala
210                 215                 220

Gln Glu Val Ala Gly Ser Ala Glu Val Lys Thr Gly Asn Gly Ile Arg
225                 230                 235                 240

His Ile Gly Leu Ala Ala Lys Gln
                245

<210> SEQ ID NO 68
<211> LENGTH: 248
<212> TYPE: PRT
<213> ORGANISM: Neisseria meningitidis

<400> SEQUENCE: 68

Val Ala Ala Asp Ile Gly Ala Gly Leu Ala Asp Ala Leu Thr Ala Pro
  1               5                  10                  15

Leu Asp His Lys Asp Lys Gly Leu Gln Ser Leu Thr Leu Asp Gln Ser
                 20                  25                  30

Val Arg Lys Asn Glu Lys Leu Lys Leu Ala Ala Gln Gly Ala Glu Lys
                 35                  40                  45

Thr Tyr Gly Asn Gly Asp Ser Leu Asn Thr Gly Lys Leu Lys Asn Asp
             50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Ile Ala
                115                 120                 125

Gly Glu His Thr Ser Phe Asp Lys Leu Pro Glu Gly Gly Arg Ala Thr
            130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Glu Leu Ala Ala Ala Asp Ile Lys
                180                 185                 190
```

Ala Asp Gly Lys Arg His Ala Val Ile Leu Gly Asp Thr Arg Tyr Gly
        195                 200                 205

Ser Glu Glu Lys Gly Thr Tyr Ser Leu Gly Ile Phe Gly Gly Lys Ala
    210                 215                 220

Gln Glu Val Ala Gly Ser Ala Glu Val Lys Thr Arg Asn Gly Ile Arg
225                 230                 235                 240

His Ile Gly Leu Ala Ala Lys Gln
            245

<210> SEQ ID NO 69
<211> LENGTH: 248
<212> TYPE: PRT
<213> ORGANISM: Neisseria meningitidis

<400> SEQUENCE: 69

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr His Gly Lys Ala Phe Gly Ser Asp Asp Pro Asn Gly Arg Leu His
145                 150                 155                 160

Tyr Thr Ile Asp Phe Ala Ala Lys Gln Gly Tyr Gly Arg Ile Glu His
                165                 170                 175

Leu Lys Thr Pro Glu Gln Asn Val Glu Leu Ala Ser Ala Glu Ile Lys
            180                 185                 190

Pro Asp Gly Lys Arg His Ala Val Ile Leu Gly Asp Val Arg Tyr Gly
        195                 200                 205

Gly Glu Glu Lys Gly Thr Tyr His Leu Gly Ile Phe Gly Gly Lys Ala
    210                 215                 220

Gln Glu Val Ala Gly Ser Ala Glu Val Lys Ile Gly Glu Gly Ile Arg
225                 230                 235                 240

His Ile Gly Leu Ala Ala Lys Gln
            245

<210> SEQ ID NO 70
<211> LENGTH: 248
<212> TYPE: PRT
<213> ORGANISM: Neisseria meningitidis

<400> SEQUENCE: 70

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
130                 135                 140

Tyr His Gly Lys Ala Phe Gly Ser Asp Asp Pro Asn Gly Arg Leu His
145                 150                 155                 160

Tyr Thr Ile Asp Phe Ala Ala Lys Gln Gly Tyr Gly Arg Ile Glu His
                165                 170                 175

Leu Lys Thr Pro Glu Gln Asn Val Glu Leu Ala Ala Ala Glu Ile Lys
            180                 185                 190

Pro Asp Gly Lys Arg His Ala Val Ile Leu Gly Asp Val Arg Tyr Gly
        195                 200                 205

Ser Glu Lys Gly Thr Tyr His Leu Gly Ile Phe Gly Gly Lys Ala
    210                 215                 220

Gln Glu Val Ala Gly Ser Ala Glu Val Lys Ile Gly Glu Gly Ile Arg
225                 230                 235                 240

His Ile Gly Leu Ala Ala Lys Gln
                245

<210> SEQ ID NO 71
<211> LENGTH: 248
<212> TYPE: PRT
<213> ORGANISM: Neisseria meningitidis

<400> SEQUENCE: 71

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr

```
            130                 135                 140
Tyr His Gly Lys Ala Phe Gly Ser Asp Asp Pro Asn Gly Arg Leu His
145                 150                 155                 160

Tyr Thr Ile Asp Phe Ala Ala Lys Gln Gly Tyr Gly Arg Ile Glu His
                165                 170                 175

Leu Lys Thr Pro Glu Gln Asn Val Glu Leu Ala Ser Ala Glu Ile Lys
            180                 185                 190

Pro Asp Gly Lys Arg His Ala Val Ile Leu Gly Asp Val Arg Tyr Gly
                195                 200                 205

Ser Glu Glu Lys Gly Thr Tyr His Leu Gly Ile Phe Gly Gly Lys Ala
            210                 215                 220

Gln Glu Val Ala Gly Ser Ala Glu Val Lys Ile Gly Glu Gly Ile Arg
225                 230                 235                 240

His Ile Gly Leu Ala Ala Lys Gln
                245

<210> SEQ ID NO 72
<211> LENGTH: 248
<212> TYPE: PRT
<213> ORGANISM: Neisseria meningitidis

<400> SEQUENCE: 72

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Leu Gly
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Tyr Gly Arg Ile Glu His
                165                 170                 175

Leu Lys Ser Pro Glu Leu Asn Val Glu Leu Ala Ala Ala Glu Ile Lys
            180                 185                 190

Ala Asp Glu Lys Ser His Ala Val Ile Leu Gly Asp Val Arg Tyr Gly
        195                 200                 205

Ser Glu Glu Lys Gly Thr Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245
```

<210> SEQ ID NO 73
<211> LENGTH: 248
<212> TYPE: PRT
<213> ORGANISM: Neisseria meningitidis

<400> SEQUENCE: 73

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Leu Gly
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Tyr Gly Arg Ile Glu His
                165                 170                 175

Leu Lys Ser Pro Glu Leu Asn Val Glu Leu Ala Ala Ala Glu Ile Lys
            180                 185                 190

Ala Asp Glu Lys Ser His Ala Val Ile Leu Gly Asp Val Arg Tyr Gly
        195                 200                 205

Gly Glu Glu Lys Gly Thr Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 74
<211> LENGTH: 248
<212> TYPE: PRT
<213> ORGANISM: Neisseria meningitidis

<400> SEQUENCE: 74

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

```
Leu Ile Thr Leu Glu Ser Gly Glu Phe Gln Val Tyr Lys Gln Ser His
                 85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Leu Gly
            115                 120                 125

Gly Glu His Thr Ser Phe Asp Lys Leu Pro Glu Gly Gly Arg Ala Thr
            130                 135                 140

Tyr Arg Gly Thr Ala Phe Gly Ser Asp Asp Ala Gly Lys Leu Thr
145                 150                 155                 160

Tyr Thr Ile Asp Phe Ala Ala Lys Gln Gly His Gly Lys Ile Glu His
                165                 170                 175

Leu Lys Ser Pro Glu Leu Asn Val Glu Leu Ala Ala Ala Glu Ile Lys
            180                 185                 190

Ala Asp Glu Lys Ser His Ala Val Ile Leu Gly Asp Val Arg Tyr Gly
            195                 200                 205

Ser Glu Glu Lys Gly Thr Tyr Ser Leu Gly Ile Phe Gly Gly Lys Ala
            210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 75
<211> LENGTH: 248
<212> TYPE: PRT
<213> ORGANISM: Neisseria meningitidis

<400> SEQUENCE: 75

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Leu Gly
            115                 120                 125

Gly Glu His Thr Ser Phe Asp Lys Leu Pro Glu Gly Gly Arg Ala Thr
            130                 135                 140

Tyr Arg Gly Thr Ala Phe Gly Ser Asp Asp Ala Gly Lys Leu Thr
145                 150                 155                 160

Tyr Thr Ile Asp Phe Ala Ala Lys Gln Gly His Gly Lys Ile Glu His
                165                 170                 175

Leu Lys Ser Pro Glu Leu Asn Val Glu Leu Ala Ala Ala Glu Ile Lys
            180                 185                 190

Ala Asp Glu Lys Ser His Ala Val Ile Leu Gly Asp Val Arg Tyr Gly
            195                 200                 205
```

Gly Glu Glu Lys Gly Thr Tyr Ser Leu Gly Ile Phe Gly Gly Lys Ala
        210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 76
<211> LENGTH: 248
<212> TYPE: PRT
<213> ORGANISM: Neisseria meningitidis

<400> SEQUENCE: 76

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Lys
65                  70                  75                  80

Leu Ile Thr Leu Glu Ser Gly Glu Phe Gln Val Tyr Lys Gln Ser His
                85                  90                  95

Ser Ala Leu Thr Ala Leu Gln Thr Glu Gln Val Gln Asp Ser Glu Asp
                100                 105                 110

Ser Gly Lys Met Val Ala Lys Arg Gln Phe Arg Ile Gly Asp Ile Ala
            115                 120                 125

Gly Glu His Thr Ser Phe Asp Lys Leu Pro Lys Gly Gly Ser Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly His Gly Lys Ile Glu His
                165                 170                 175

Leu Lys Ser Pro Glu Leu Asn Val Glu Leu Ala Thr Ala Glu Leu Lys
                180                 185                 190

Ala Asp Glu Lys Ser His Ala Val Ile Leu Gly Asp Thr Arg Tyr Gly
            195                 200                 205

Gly Glu Glu Lys Gly Thr Tyr His Leu Ala Leu Phe Gly Asp Arg Ala
    210                 215                 220

Gln Glu Ile Ala Gly Ser Ala Thr Val Lys Ile Arg Glu Lys Val His
225                 230                 235                 240

Glu Ile Gly Ile Ala Gly Lys Gln
                245

<210> SEQ ID NO 77
<211> LENGTH: 274
<212> TYPE: PRT
<213> ORGANISM: Neisseria meningitidis

<400> SEQUENCE: 77

Met Asn Arg Thr Ala Phe Cys Cys Phe Ser Leu Thr Ala Ala Leu Ile
1               5                   10                  15

Leu Thr Ala Cys Ser Ser Gly Gly Gly Val Ala Ala Asp Ile Gly
                20                  25                  30

Ala Gly Leu Ala Asp Ala Leu Thr Ala Pro Leu Asp His Lys Asp Lys
            35                  40                  45

Gly Leu Gln Ser Leu Thr Leu Asp Gln Ser Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Lys Leu Ile Thr Leu Glu Ser
            100                 105                 110

Gly Glu Phe Gln Val Tyr Lys Gln Ser His Ser Ala Leu Thr Ala Leu
            115                 120                 125

Gln Thr Glu Gln Val Gln Asp Ser Glu Asp Ser Gly Lys Met Val Ala
130                 135                 140

Lys Arg Gln Phe Arg Ile Gly Asp Ile Ala Gly Glu His Thr Ser Phe
145                 150                 155                 160

Asp Lys Leu Pro Lys Gly Gly Ser Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly His Gly Lys Ile Glu His Leu Lys Ser Pro Glu Leu
            195                 200                 205

Asn Val Glu Leu Ala Thr Ala Glu Leu Lys Ala Asp Glu Lys Ser His
            210                 215                 220

Ala Val Ile Leu Gly Asp Thr Arg Tyr Gly Gly Glu Glu Lys Gly Thr
225                 230                 235                 240

Tyr His Leu Ala Leu Phe Gly Asp Arg Ala Gln Glu Ile Ala Gly Ser
                245                 250                 255

Ala Thr Val Lys Ile Arg Glu Lys Val His Glu Ile Gly Ile Ala Gly
            260                 265                 270

Lys Gln

<210> SEQ ID NO 78
<211> LENGTH: 825
<212> TYPE: DNA
<213> ORGANISM: Neisseria meningitidis

<400> SEQUENCE: 78
gtgaaccgaa ctgccttctg ctgcttttct ctgaccgccg ccctgattct gaccgcctgc      60
agcagcggag ggggcggtgt cgccgccgac atcggtgcgg ggcttgccga tgcactaacc     120
gcaccgctcg accataaaga caaaggtttg cagtctttaa cgctggatca gtccgtcagg     180
aaaaacgaga aactgaagct ggcggcacaa ggtgcggaaa aaacttatgg aaacggcgac     240
agccttaata cgggcaaatt gaagaacgac aaggtcagcc gcttcgactt tatccgtcaa     300
atcgaagtgg acgggaagct cattaccttg gagagcggag agttccaagt gtacaaacaa     360
agccattccg ccttaaccgc ccttcagacc gagcaagtac aagactcgga ggattccggg     420
aagatggttg cgaaacgcca gttcagaatc ggcgacatag cgggcgaaca tacatctttt     480
gacaagcttc ccaaaggcgg cagtgcgaca tatcgcggga cggcgttcgg ttcagacgat     540
gctggcggaa aactgaccta tactatagat ttcgccgcca agcagggaca cggcaaaatc     600
gaacatttga aatcgcccga actcaatgtc gagcttgcca ccgccgaact caaagcagat     660
gaaaaatcac acgccgtcat tttgggcgac acgcgctacg gcggcgaaga aaaaggcact     720

```
taccacctcg cccttttcgg cgaccgcgcc caagaaatcg ccggctcggc aaccgtgaag    780
ataagggaaa aggttcacga aatcggcatc gccggcaaac agtaa                   825
```

<210> SEQ ID NO 79
<211> LENGTH: 249
<212> TYPE: PRT
<213> ORGANISM: Neisseria meningitidis

<400> SEQUENCE: 79

```
Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
            20                  25                  30

Ser Val Arg Lys Asn Glu Lys Leu Lys Leu Ala Ala Gln Gly Ala Glu
        35                  40                  45

Lys Thr Tyr Gly Asn Gly Asp Ser Leu Asn Thr Gly Lys Leu Lys Asn
    50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125

Ala Gly Glu His Thr Ser Phe Asp Lys Leu Pro Gly Gly Arg Ala
    130                 135                 140

Thr Tyr His Gly Lys Ala Phe Gly Ser Asp Asp Pro Asn Gly Arg Leu
145                 150                 155                 160

His Tyr Thr Ile Asp Phe Ala Ala Lys Gln Gly Tyr Gly Arg Ile Glu
                165                 170                 175

His Leu Lys Thr Pro Glu Gln Asn Val Asp Leu Ala Ala Ala Asp Ile
            180                 185                 190

Lys Pro Asp Gly Lys Arg His Ala Val Ile Ser Gly Ser Val Leu Tyr
        195                 200                 205

Asn Gln Ala Glu Lys Gly Ser Tyr Ser Leu Gly Ile Phe Gly Gly Lys
    210                 215                 220

Ala Gln Glu Val Ala Gly Ser Ala Glu Val Lys Ile Gly Glu Gly Ile
225                 230                 235                 240

Arg His Ile Gly Leu Ala Ala Lys Gln
                245
```

<210> SEQ ID NO 80
<211> LENGTH: 248
<212> TYPE: PRT
<213> ORGANISM: Neisseria meningitidis

<400> SEQUENCE: 80

```
Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
            20                  25                  30

Ser Val Arg Lys Asn Glu Lys Leu Lys Leu Ala Ala Gln Gly Ala Glu
        35                  40                  45

Lys Thr Tyr Gly Asn Gly Asp Ser Leu Asn Thr Gly Lys Leu Lys Asn
```

```
            50                  55                  60
Asp Lys Val Ser Arg Phe Asp Phe Ile Arg Gln Ile Glu Val Asp Gly
 65                  70                  75                  80

Gln Leu Ile Thr Leu Glu Ser Gly Glu Phe Gln Val Tyr Lys Gln Ser
                 85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Leu
        115                 120                 125

Gly Gly Glu His Thr Ala Phe Asn Gln Leu Pro Asp Gly Lys Ala Glu
    130                 135                 140

Tyr Arg Gly Thr Ala Phe Gly Ser Asp Asp Ala Gly Gly Lys Leu Thr
145                 150                 155                 160

Tyr Thr Ile Asp Phe Thr Lys Lys Gln Gly Asn Gly Lys Ile Glu His
                165                 170                 175

Leu Lys Ser Pro Glu Leu Asn Val Glu Leu Ala Ser Ala Glu Ile Lys
            180                 185                 190

Ala Asp Gly Lys Ser His Ala Val Ile Leu Gly Asp Val Arg Tyr Gly
        195                 200                 205

Ser Glu Glu Lys Gly Ser Tyr Ser Leu Gly Ile Phe Gly Gly Arg Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 81
<211> LENGTH: 26
<212> TYPE: DNA
<213> ORGANISM: Artificial Sequence
<220> FEATURE:
<223> OTHER INFORMATION: IC31 polynucleotide
<220> FEATURE:
<221> NAME/KEY: N
<222> LOCATION: 1,3,5,7,9,11,13,15,17,19,21,23,25
<223> OTHER INFORMATION: N is Inosine

<400> SEQUENCE: 81
ncncncncnc ncncncncnc ncncnc                                      26

<210> SEQ ID NO 82
<211> LENGTH: 11
<212> TYPE: PRT
<213> ORGANISM: Artificial Sequence
<220> FEATURE:
<223> OTHER INFORMATION: IC31 polypeptide

<400> SEQUENCE: 82

Lys Leu Lys Leu Leu Leu Leu Leu Lys Leu Lys
1               5                   10

<210> SEQ ID NO 83
<211> LENGTH: 248
<212> TYPE: PRT
<213> ORGANISM: Neisseria meningitidis

<400> SEQUENCE: 83

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
```

```
                    20                  25                  30
Val Arg Lys Asn Glu Lys Leu Lys Leu Ala Ala Gln Gly Ala Glu Lys
            35                  40                  45
Thr Tyr Gly Asn Gly Asp Ser Leu Asn Thr Gly Lys Leu Lys Asn Asp
    50                  55                  60
Lys Val Ser Arg Phe Asp Phe Ile Arg Gln Ile Glu Val Asp Gly Gln
65                  70                  75                  80
Leu Ile Thr Leu Glu Ser Gly Glu Phe Gln Val Tyr Lys Gln Ser His
                85                  90                  95
Ser Ala Leu Thr Ala Phe Gln Thr Glu Gln Ile Gln Asp Ser Glu His
            100                 105                 110
Ser Gly Lys Met Val Ala Lys Arg Gln Phe Arg Ile Gly Asp Ile Ala
            115                 120                 125
Gly Glu His Thr Ser Phe Asp Lys Leu Pro Glu Gly Gly Arg Ala Thr
        130                 135                 140
Tyr Arg Gly Thr Ala Phe Gly Ser Asp Asp Ala Gly Gly Lys Leu Thr
145                 150                 155                 160
Tyr Thr Ile Asp Phe Ala Ala Lys Gln Gly Asn Gly Lys Ile Glu His
                165                 170                 175
Leu Lys Ser Pro Glu Leu Asn Val Asp Leu Ala Ala Ala Asp Ile Lys
            180                 185                 190
Pro Asp Gly Lys Arg His Ala Val Ile Ser Gly Ser Val Leu Tyr Asn
            195                 200                 205
Gln Ala Glu Lys Gly Ser Tyr Ser Leu Gly Ile Phe Gly Gly Lys Ala
        210                 215                 220
Gln Glu Val Ala Gly Ser Ala Glu Val Lys Thr Val Asn Gly Ile Arg
225                 230                 235                 240
His Ile Gly Leu Ala Ala Lys Gln
                245
```